US006914048B2

(12) United States Patent
Gellman et al.

(10) Patent No.: US 6,914,048 B2
(45) Date of Patent: Jul. 5, 2005

(54) METHOD FOR DELIVERY OF MOLECULES TO INTRACELLULAR TARGETS

(75) Inventors: Samuel H. Gellman, Madison, WI (US); Naoki Umezawa, Nagoya (JP); Michael A. Gelman, Madison, WI (US); Ronald T. Raines, Madison, WI (US); Terra Potocky, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/246,441

(22) Filed: Sep. 18, 2002

(65) Prior Publication Data

US 2003/0119189 A1 Jun. 26, 2003

Related U.S. Application Data

(60) Provisional application No. 60/323,512, filed on Sep. 18, 2001.

(51) Int. Cl.[7] .......................... A61K 38/08; A61K 38/10; C07K 7/02

(52) U.S. Cl. ............................. 514/12; 514/13; 514/14; 514/15; 514/16; 514/17; 530/324; 530/325; 530/326; 530/327; 530/328; 530/329; 530/332; 530/345

(58) Field of Search ............................... 514/2, 12, 13, 514/14, 15, 16, 17; 530/300, 324, 325, 326, 327, 328, 329, 332, 345

(56) References Cited

U.S. PATENT DOCUMENTS

2002/0132766 A1   9/2002   DeGrado et al. ............. 514/12

OTHER PUBLICATIONS

Barron, A. E.; Zuckerman, R. N., Bioinspired polymeric materials: in–between poreins and plastics, *Curr. Opin. Chem. Biol.* 1999, 3, 681–87.
DeGrado, W.F.; Schneider, J. P.; Hamuro, Y., The twists and turns of β–peptides, *J. Pept. Res.* 1999, 54, 206–17.
Derossi, D.; Joliot, A.H.; Chassaing, G.; Prochiantz, A., Trojan peptides; the penetratin system for intracellular delivery, *J. Biol. Chem.* 1994, 269, 10444–47.
Derossi, D.; Calvet, S.; Trembleau, A.; Brunissen, A.; Chassaing, G.; Prochiantz, A., Cell Internalization of the Third Helix of the Antennapedia Homeodomain Is Receptor–independent, *J. Biol. Chem.* 1996, 271, 18188–93.
Fawell, S.; Seery, J.; Kaikh, Y.; Moore, C.; Chen, L. L.; Pepinsky, B.; Barsoum, J., Tat–mediated delivery of heterologous proteins into cells, *Proc. Natl. Acad. Sci. USA* 1994, 91, 664–68.
Frankel, A. D.; Pabo, C. O., Cellular Uptake of the Tat Protein from Human Immunodeficiency Virus, *CEll* 1988, 22, 1189–93.

Futaki, S.; Suzuki, T.; Ohashi, W.; Yagami, T.; Tanaka, S.; Ueda, K.; Sugiura, Y., Arginine–rich Peptides, *J. Biol. Chem.* 2001, 276, 5836–40.
Gademann, K.; Hintermann, T.; Schreiber, J. V., β–Piptides: Twisting and Turning, *Curr. Med. Chem.* 1999, 6, 905–25.
Gellman, S. H., Foldamers: A Maniffesto, *Acc. Chem. Res.* 1998, 31, 173–80.
Green, M.; Loewenstein, P. M., Autonomous Functional Domains of Chemically Synthesized Human Immunodeficiency Virus Tat *Trans*–Actovator Protein, *Cell* 1988, 55, 1179–88.
Guichard, G.; Abele, S.; Seebach, D., Preparatio of N–Fmoc–Protected $\beta^2$– and $\beta^3$– Amino Acids and Their Use as Building Blocks for the Solid–Phase Synthesis of β–Peptides, *Helv. Chim. Acta* 1998, 81, 187–98.
Hamuro, Y.; Schneider, J. P.; DeGrado, W. F., De Novo Design of Antibacterial β– Peptides, *J. Am. Chem. Soc.* 1999, 121, 12200–01.
Hawiger, J., Noninvasive intracellular delivery of functional pepides and proteins, *Curr. Opin. Chem. Biol.* 1999, 3, 89–94.
Kirshenbaum, K.; Zuckermann, R. N.; Dill, K. A., Designing polymers that mimic biomolecules, *Curr. Opin. Struct. Biol.* 1999, 9, 530–535.
Lindgren, M.; Hallbrink, M.; Prochiantz, A.; Langel, Ü., Cell–penetrating peptides, *Trends Pharmacol. Sci.* 2000, 21, 99–103.
Mitchell, D. J.; Kim, D. T.; Steinman, L.; Fathman, C. G.; Rothbard, J. B., Polyarginine enters cells more efficiently than other polcationic homopolymers, *J. Pept. Res.* 2000, 56, 318–25.
Pooga, M.; Soomets, U.; Hällbrink, M.; Valkna, A.; Saar, K.; Rezaei, K.; Kahl, U.; Hao, J.-X.; Xu, X.-J.; Wiesenfeld–Hallin, Z.; Hökfelt, T.; Bartfai, T.; Langel, Ü., Cell penetrating PNA constructs regulate galanin receptor levels and modify pain transmission in vivo, *Nat. Biotechnol.* 1998, 16, 857–61.
Porter, E. A.; Wang, X.; Lee, H.-S.; Weisblum, B.; Gellman, S. H., Non–haemolytic β–amino–acid oligomers, *Nature* 2000, 404, 565.

(Continued)

*Primary Examiner*—Jeffrey Edwin Russel
(74) *Attorney, Agent, or Firm*—Joseph T. Leone, Esq.; DeWitt Ross & Stevens S.C.

(57) ABSTRACT

Disclosed are β-peptides and β-peptide conjugates that are capable of diffusing or otherwise being transported across the cell membranes of living cells. The β-peptides contain at least six β-amino acid residues, at leastsix of which are preferably $\beta^3$-homoarginine residues. It has been found that when pharmacologically-active agents are conjugated to these types of β-peptides, the resulting conjugates (also disclosed herein) are also capable of diffusing or otherwise being transported across the cell membranes of living cells, including mammalian cells.

26 Claims, 4 Drawing Sheets

OTHER PUBLICATIONS

Prochiantz, A., Messenger proteins: homeoproteins, TAT and others, *Curr. Opin. Cell Biol.* 2000, 12, 400–06.

Rothbard, J. B.; Garlington, S.; Lin, Q.; Kirschberg, T.; Kreider, E.; McGrane, P. L.; Wender, P. A.; Khavari, P. A., Conjugation of arginine oligomers to cyclosporin A facilitates topical delivery and inhibition of inflammation, *Nat. Medicine* 2000, 6, 1253–57.

Rouselle, C.; Clair, P.; Lefauconnier, J.–M.; Kaczorek, M.; Scherrmann, J.–M.; Temsamani, J., New Advances in the Transport of Doxorubicin through the Blood–Brain Barrier by a Peptide Vector–Mediated Strategy, *Mol. Pharmacol.* 2000, 57, 679–686.

Rueping, M.; Mahajan, Y.; Sauer, M; and Seebach, D.,Cellular Uptake Studies with β–Peptides, *ChemBioChem* 2002, No. 02–03, 257–259.

Schwarze, S. R.; Ho, A.; Vocero–Akbani, A.; Dowdy, S. F., In Vivo Protein Transduction: Delivery of a Biologically Active Protein into the Mouse, *Science* 1999, 285, 1569–72.

Schwarze, S. R.; Hruska, K. A.; Dowdy, S. F., Protein transduction: unrestricted delivery into all cells!, *Trends Cell Biol.* 2000, 10, 290–95.

Schwarze, S.R. and Dowdy, S.F., In vivo protein transduction: intracellular delivery of biologically active proteins, compounds and DNA, *TiPS*, 2000, 21, 45–48.

Seebach, D.; Matthews, J. L., β–Peptides: a surprise at every turn, *J. Chem. Soc., Chem. Commun.* 1997, 2015–22.

Seebach, D.; Abele, S.; Schreiber, J. V.; Martinoni, B.; Nussbaum, A. K.; Schild, H.; Schulz, H.; Hennecke, H.; Woessner, R; Bitsch, F., Biological and Pharmacokinetic Studies with β–Peptides, *Chimia* 1998, 52, 734–39.

Stigers, K. D.; Soth, M.J.; Nowick, J. S., Designed molecules that fold to mimic protein secondary structures, *Curr. Opin. Chem. Biol.* 1999, 3, 714–23.

Tamilarasu, N.; Huq, I.; Rana, T. M., High Affinity and Specific Binding of HIV–1 TAR RNA by a Tat–Derived Oligourea, *J. Am. Chem. Soc.* 1999, 121, 1597–98.

Umezawa, N.; Gelman, M.A.; Haigis, M.C.; Rainer, R.T.; and Gellman, S.H.,, Translocation of a β–Peptide Across Cell Membranes, *J. Am. Chem.Soc.* 2002, vol. 24, No. 3, 368–369.

Vivés, E.; Brodin, P.; Lebleu, B., A Truncated HIV–1 Tat Protein Basic Domain Rapidly Translocates through the Plasma Membrane and Accumulates in the Cell Nucleus, *J. Biol. Chem.* 1997, 272, 16010–17.

Vivés, E.; Granier, C.; Prevot, P.; Lebleu, B., Structure–activity relationship study of the plasma membrane translocating potential of a short peptide from HIV–1 Tat protein, *Lett. Pept. Sci.* 1997, 4, 429–436.

Wang, X.; Huq, I.; Rana, T. M., HIV–1 TAR RNA Recognition by Unnatural Biopolymer, *J. Am. Chem. Soc.* 1997, 119, 6444–45.

Wender, P.A.; Mitchell, D. J.; Pattabiraman, K.; Pelkey, E. T.; Steinman, L.; Rothbard, J. B., the design , synthesis, and evaluation of molecules that enable or enhance cellular uptake: Peptoid molecular transporters, *Proc. Natl. Acad. Sci. USA* 2000, 97, 13003–08.

Werder, M.; Hausre, H.; Abele, S.; Seebach, D., β–Peptides as Inhibitors of Small–Intestinal Cholesterol and Fat Absorption, *Helv. Chim. Acta* 1999, 82, 1774–83.

Zhang, L.; Torgerson, T. R.; Liu, X.–Y.; Timmons, S.; Colosia, A. D.; Hawiger, J.; Tam, J. P., Preparation of functionality active cell–permeable peptide by sinlge–step ligation of two peptides modules, *Proc. Natl. Acad. Sci. USA* 1998, 95, 9184–89.

Bastiaans, Harold M., A facile conversion of arginine into β–homoarginine dipeptides, *Tetrahedron Letters*, 1994, vol. 35, No. 41, pp. 7659–7660.

METHOD FOR DELIVERY OF MOLECULES TO INTRACELLULAR TARGETS

PRIORITY

Priority is hereby claimed to provisional patent application Ser. No. 60/323,512, filed Sep. 18, 2001, the content of which is incorporated herein.

FEDERAL SUPPORT

This invention was made with United States government support awarded by the following agencies: NIH GM56414. The United States has certain rights in this invention.

FIELD OF THE INVENTION

The invention is directed to a method of using synthetic β-amino acid oligomers (generally referred to herein as "β-peptides") as drug-delivery "vehicles" or stand-alone pharmacologically-active agents. As detailed below, the present inventors have found that certain β-peptides and β-peptide conjugates diffuse across the cell membranes of living mammalian cells. Pharmacologically-active moieties conjugated to the β-peptides are transported across cell membranes along with the β-peptide "vehicle." Thus, the β-peptides and β-peptide conjugates disclosed herein are useful to delivery pharmacologically-active agents to the interior of living cells.

BACKGROUND

Biological membranes are critical for life because these barriers, situated between the cytoplasm and the "outside" world, allow cells to regulate entry of water-soluble molecules from the surrounding environment. The barrier presented by biological membranes, however, is often problematic from a biomedical perspective. Membrane impermeability often inhibits the delivery of polar, pharmacologically-active molecules (peptides, nucleic acids, etc.) to specific intracellular targets. Unable to reach their targets, these polar molecules are subject to degradation and clearance and are thus rendered pharmacologically inactive.

Over the past decade, numerous short α peptides have been found to move rapidly across biological membranes.[1] Initial discoveries involved cationic sequences from natural proteins, e.g., short fragments of the HIV Tat protein[2] and fragments of the homeo-domain of the *Drosophila* transcription factor Antennapedia.[3] Many additional α peptide sequences with similar translocation properties have also been identified, including hydrophobic segments from signal peptides[4] and arginine oligomers.[5] Wender et al. have recently shown that peptoid oligomers (i.e., N-alkyl-glycine) bearing multiple guanidinium-tipped side-chains, also move across the membranes of living cells.[6] Such translocating peptides have the potential to deliver to intracellular targets diverse cargos conjugated to the peptides, including proteins,[7] peptide-nucleic acids[8] and drug molecules.[9]

In 1988 work by Green and Lowenstein and Frankel and Pabo showed that the HIV Tat and related DNA-binding proteins move spontaneously from outside cells through their membrane and into the nuclei.[10] More recent work has demonstrated that the translocation activity depends upon relatively short peptide segments within such proteins.[2,3] HIV Tat 47–57 is among the shortest examples.[11] In the present invention, it has been surprisingly shown that a β-amino acid analog (101) of the HIV Tat 47–57 translocation sequence, and HIV Tat 47–57 itself (102) move with comparable efficiency across the membranes of human cells.

β-Amino acid oligomers ("β-peptides") have received extensive scrutiny in recent years.[12] They can adopt well-defined protein-like secondary structures, and several β-peptides with interesting biological activities have been reported.[13] Importantly, β-peptides are resistant to the action of proteases and other degradative processes.[14]

SUMMARY OF THE INVENTION

In a first embodiment, the invention is directed to a method of translocating a molecule across a membrane of a living cell. The method comprises conjugating the molecule to an oligopeptide, where the oligopeptide comprises at least 11, and preferably at least six, contiguous β-amino acid residues. Regardless of the overall length of the oligopeptide, at least six of the residues must be substituted at the β-carbon position with a guanidino-$C_1$-$C_6$-alkyl group (i.e., —$C_1$-$C_6$—NH—C(=$NH_2^+$)—$NH_2$), with guanidino-$C_2$-$C_4$-alkyl groups being more preferred, and the most preferred substitution being $β^3$-homoarginine residues. The resulting conjugate is then contacted with the living cell, wherein the conjugate is transported across the cell membrane and into the interior of the cell.

A second embodiment of the invention is directed to β-peptides capable of translocating across the membrane of a living cell. The β-peptide of the invention comprises at least 11, and preferably at least six, β-amino acid residues, at least six of which residues are substituted at the β-carbon as noted in the immediately preceding paragraph.

A third embodiment of the invention is directed to a conjugate comprising a β-peptide vehicle conjugated to a molecule of interest, preferably (but not necessarily) a molecule having pharmacological activity. In this embodiment of the invention, the β-peptide vehicle comprises a β-peptide capable of translocating across the membrane of a living cell, as described in the preceding paragraph. The molecule of interest is unlimited and may be any compound (organic, inorganic, organo-metallic, metal, non-metal) or complex capable of being conjugated to the β-peptide vehicle.

In all embodiments of the invention, at least six of the residues of the β-peptide must be substituted at the β-position carbon with a guanidino-$C_1$-$C_6$-alkyl group; most preferably, these six residues are $β^3$-homoarginine residues.

There is no upper limit to the length of the β-peptide vehicle. For purposes of economy, β-peptides 24 residues long and smaller are preferred, with a more preferred overall length ranging from six to 18 residues, and the most preferred overall length ranging from six to 12 residues.

In any of the first, second, or third embodiments of the invention, where the overall length of the β-peptide is greater than six residues, one or more of the residues in excess of six may be a cyclically-constrained β-peptide. Where there are cyclically-constrained β-peptides present, it is preferred that they be selected from the group consisting of:

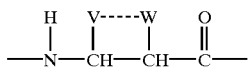

wherein V and W are combined, together with the carbon atoms to which they are bonded, and independently define a substituted or unsubsituted, monocyclic or bicyclic $C_3$-$C_{10}$ cycloalkyl, cycloalkenyl or heterocyclic ring having one or more N, O or S atom(s) as the heteroatom(s);

the substituents on carbon atoms of the rings being independently selected from the group consisting of hydroxy, linear, branched, or cyclic $C_1$–$C_6$-alkyl, alkenyl, alkynyl; hydroxy-$C_1$–$C_6$-alkyl, amino-$C_1$–$C_6$-alkyl, $C_1$–$C_6$-alkyloxy, $C_1$–$C_6$-alkyloxy-$C_1$–$C_6$-alkyl, amino, mono- or di-$C_1$–$C_6$-alkylamino, carboxamido, carboxamido-$C_1$–$C_6$-alkyl, sulfonamido, sulfonamido-$C_1$–$C_6$-alkyl, urea, cyano, fluoro, thio, $C_1$–$C_6$-alkylthio, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, the substituents on nitrogen heteroatoms of the rings being independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl-S(=O)$_2$—$R^1$, —C(=O)—$R^1$, —S(=O)$_2$—(CH$_2$)$_{n+1}$—$R^2$, and —C(=O)—(CH$_2$)$_n$—$R^2$, where n=1 to 6;

wherein $R^1$ is independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^2$ is independently selected from the group consisting of hydroxy, linear, branched, or cyclic $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane; and wherein each cyclically-constrained β-amino acid residue is further selected from the group consisting of:

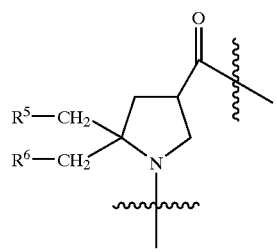

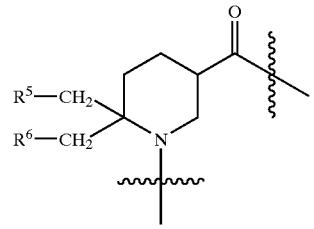

wherein $R^5$ and $R^6$ are independently selected from the group consisting of hydrogen, hydroxy, linear, branched, or cyclic $C_1$–$C_{16}$-alkyl, alkenyl, or alkynyl; mono- or di-$C_1$–$C_{16}$ alkylamino; mono- or bicyclic aryl; mono- or bicyclic heteroaryl having up to 5 heteroatoms selected from N, O, and S; mono- or bicyclic aryl-$C_1$–$C_{16}$-alkyl; mono- or bicyclic heteroaryl-$C_1$–$C_{16}$-alkyl; —(CH$_2$)$_{0-6}$—OR$^7$, —(CH$_2$)$_{0-6}$—SR$^7$, —(CH$_2$)$_{0-6}$—S(=O)—CH$_2$—R$^7$, —(CH$_2$)$_{0-6}$—S(=O)$_2$—CH$_2$—R$^7$, —(CH$_2$)$_{0-6}$—NR$^7$R$^7$, —(CH$_2$)$_{0-6}$—NHC(=O)R$^7$, —(CH$_2$)$_{0-6}$—NHS(=O)$_2$—CH$_2$—R$^7$, —(CH$_2$)$_{0-6}$—C(=O)—OH, —(CH$_2$)$_{0-6}$—C(=O)—OR$^7$, —(CH$_2$)$_{0-6}$—C(=O)—NH$_2$, —(CH$_2$)$_{0-6}$—C(=O)—NHR$^7$, —(CH$_2$)$_{0-6}$—C(=O)—N(R$^7$)$_2$, —(CH$_2$)$_{0-6}$—O—(CH$_2$)$_{2-6}$—R$^8$, —(CH$_2$)$_{0-6}$—S—(CH$_2$)$_{2-6}$—R$^8$, —(CH$_2$)$_{0-6}$—S(=O)—(CH$_2$)$_{2-6}$—R$^8$, —(CH$_2$)$_{0-6}$—S(=O)$_2$—(CH$_2$)$_{2-6}$—R$^8$, —(CH$_2$)$_{0-6}$—NH—(CH$_2$)$_{2-6}$R$_8$, —(CH$_2$)$_{0-6}$—N—{(CH$_2$)$_{2-6}$—R$^8$}$_2$, —(CH$_2$)$_{0-6}$—NHC(=O)—(CH$_2$)$_{2-6}$—R$^8$, and —(CH$_2$)$_{0-6}$—NHS(=O)$_2$—(CH$_2$)$_{2-6}$—R$^8$; wherein $R^7$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^8$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane; and wherein each cyclically-constrained β-amino acid residues is further selected from the group consisting of:

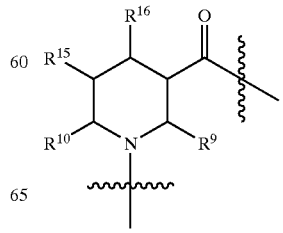

and

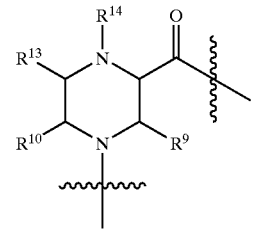

and

-continued

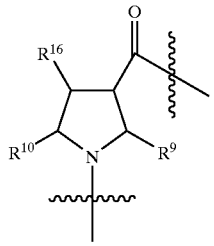

wherein $R^9$, $R^{10}$, and $R^{13}$ are independently selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{1-6}$—$OR^{11}$, —$(CH_2)_{1-6}$—$SR^{11}$, —$(CH_2)_{1-6}$—$S(=O)$—$CH_2$—$R^{11}$, —$(CH_2)_{1-6}$—$S(=O)_2$—$CH_2$—$R^{11}$, —$(CH_2)_{1-6}$—$NR^{11}R^{11}$, —$(CH_2)_{1-6}$—$NHC(=O)R^{11}$, —$(CH_2)_{1-6}$—$NHS(=O)_2$—$CH_2$—$R^{11}$, —$(CH_2)_{0-6}$—$C(=O)$—$OH$, —$(CH_2)_{0-6}$—$C(=O)$—$OR^{11}$, —$(CH_2)_{0-6}$—$C(=O)$—$NH_2$, —$(CH_2)_{0-6}$—$C(=O)$—$NHR^{11}$, —$(CH_2)_{0-6}$—$C(=O)$—$N(R^{11})_2$, —$(CH_2)_{1-6}$—$O$—$(CH_2)_{2-6}$—$R^{12}$, —$(CH_2)_{1-6}$—$S$—$(CH_2)_{2-6}$—$R^{12}$, —$(CH_2)_{1-6}$—$S(=O)$—$(CH_2)_{2-6}$—$R^{12}$, —$(CH_2)_{1-6}$—$S(=O)_2$—$(CH_2)_{2-6}$—$R^{12}$, —$(CH_2)_{1-6}$—$NH$—$(CH_2)_{2-6}$—$R^{12}$, —$(CH_2)_{1-6}$—$N$—$\{(CH_2)_{2-6}$—$R^{12}\}_2$, —$(CH_2)_{1-6}$—$NHC(=O)$—$(CH_2)_{2-6}$—$R^{12}$, and —$(CH_2)_{1-6}$—$NHS(=O)_2$—$(CH_2)_{2-6}$—$R^{12}$; wherein $R^{11}$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^{12}$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane;

$R^{14}$ is selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$S(=O)_2$—$(CH_2)_{1-6}$—$R^{11}$, —$C(=O)R^{11}$, —$S(=O)_2$—$(CH_2)_{2-6}R^{12}$, and —$C(=O)$—$(CH_2)_{1-6}$—$R^{12}$; wherein $R^{11}$ and $R^{12}$ are as defined above;

$R^{15}$ and $R^{16}$ are selected from the group listed above for $R^9$, $R^{10}$, and $R^{13}$, and are further selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, heteroaryl; O-alkylurethane, O-arylurethane, and O-heteroarylurethane.

The preferred β-peptides according to the present invention are the following:

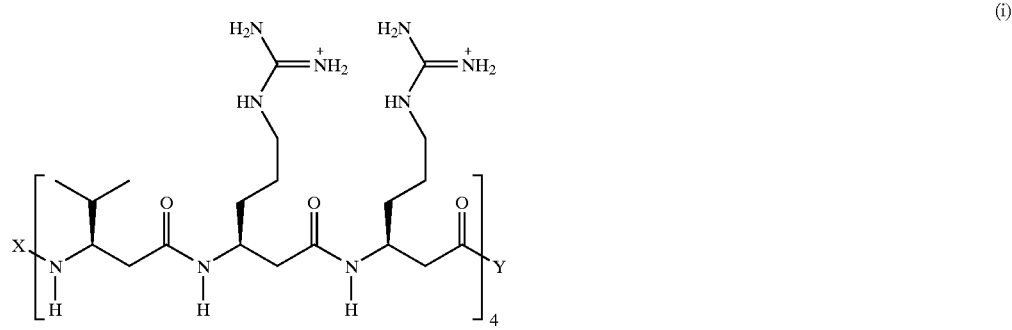

(i)

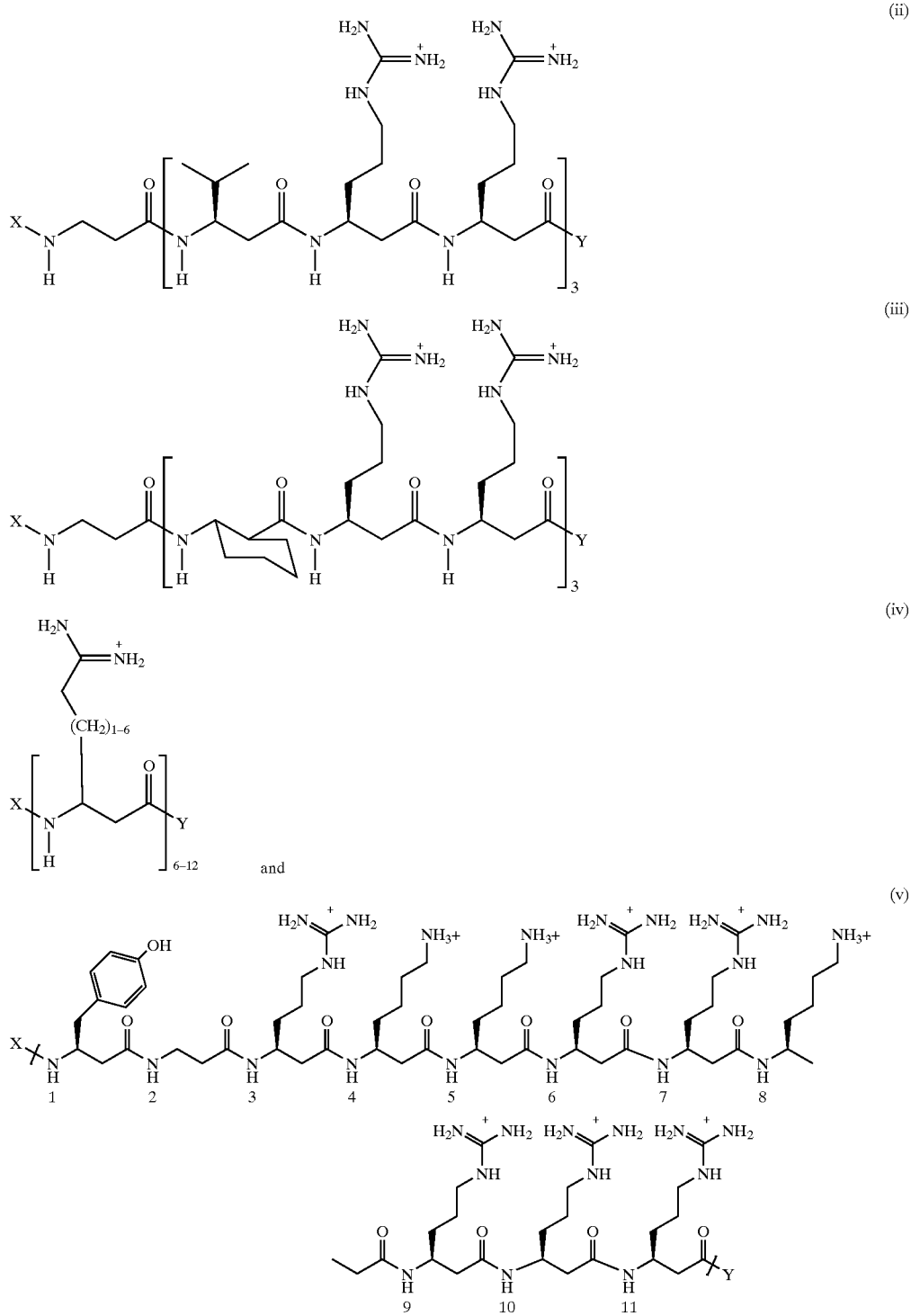

wherein X is hydrogen, an amino-capping group, an amino-protecting group, or a compound of interest; and Y is hydrogen, a carboxy-capping group, a carboxy-protecting group, or a compound of interest. (In compounds (i), (ii), and (iii), the preferred $\beta^3$-homoarginine residues are shown. These guanidino substituent in these residues may also be linked to the backbone with a shorter or longer alkyl chain (i.e., $C_{1,2,4-6}$alkyl, as noted above).

DETAILED DESCRIPTION OF THE INVENTION

Figures 1A, 1B, 1C, 1D, 1E:
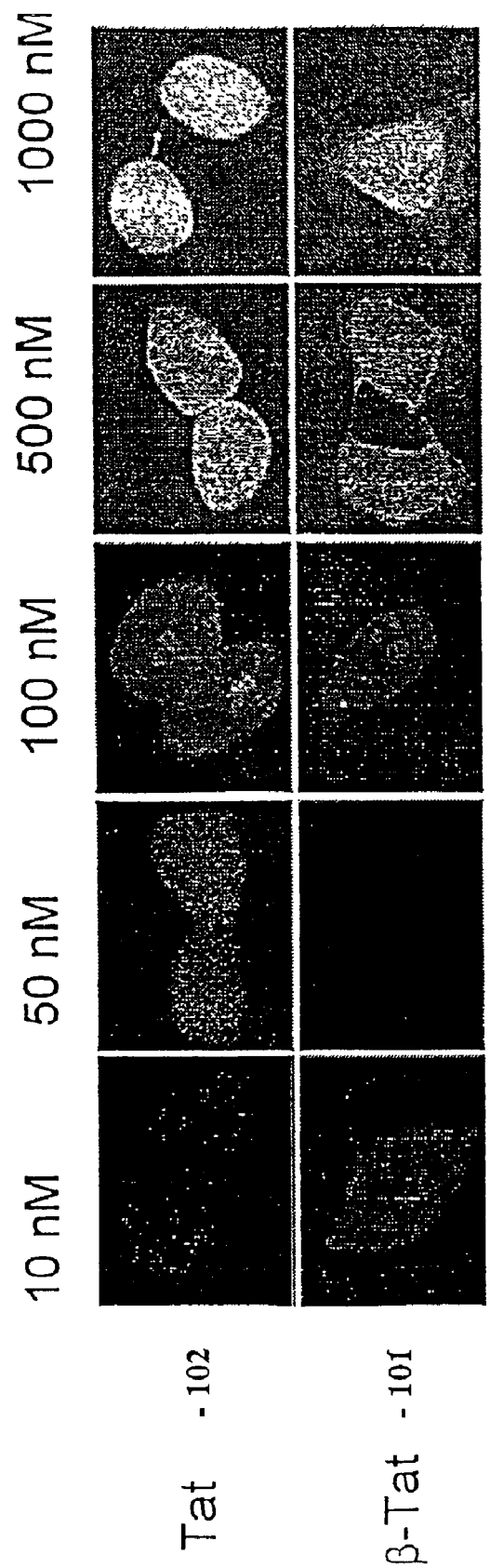
FIGS. 1A, 1B, 1C, 1D, and 1E are representative fluorescence results for compounds 101 and 102 in HeLa cells. 1A=10 nM, 1B=50 nM, 1C=100 nM, 1D=500 nM, and 1E=1,000 nM. HeLa cells were incubated at 37° C. with peptide solutions in DMEM at the given concentration for 10 min, then washed with PBS and fixed in paraformaldehyde (4% w/v in PBS).

Abbreviations and Definitions:

The following abbreviations are used throughout the specification and claims. Unless specifically defined to the contrary, all other terms have their standard accepted meanings. All of the following compounds can be purchased commercially from Aldrich Chemical Company, Milwaukee, Wis., USA, as well as other national and international suppliers:

"alkyl"=$C_1$–$C_6$ straight or branched alkyl
"Bn"=benzyl
"BnBr"=benzyl bromide
"Boc"=tert-butoxycarbonyl
"BopCl"=bis(2-oxo-3-oxazolidinyl)phosphinic chloride
"cis-5-MOM-PCA"=cis-5 methoxymethyl-3-pyrrolidine carboxylic acid
"Cbz"=carbobenzyloxy
"CSA"=10-camphorsulfonic acid
"DIEA"=diisopropyl ethyl amine
"DMAP"=N,N-dimethylaminopyridine
"DMF"=N,N-dimethylformamide
"EDCI"=N,N-dimethylaminopropyl-3-ethylcarbodiimide
"FAB MS"=fast atom bombardment mass spectrometry
"Iso-Cl"=isobutyryl chloride
"MALDI-TOF MS"=matrix-assisted laser desorption ionization, time-of-flight mass spectrometry
"Nip"=nipecotic acid
"PCA"=pyrrolidine carboxylic acid
"PiCA"=piperazine carboxylic acid
"TBAF"=tetrabutylammonium fluoride
"TCMP"=trans-3-carboxy-4-methylpiperidine
"THF"=tetrahydrofuran
"TMSCHN$_2$"=(trimethylsilyl)diazomethane
"Ts-Cl"=p-toluenesulfonyl chloride As used herein, the terms "β-amino acid" and "β-amino acid residue" refer to any and all natural and unnatural β-amino acids and their respective residues (i.e., the form of the amino acid when incorporated into a polypeptide molecule), without limitation. Specifically included are those β-amino acids described in U.S. Pat. No. 6,060,585, issued May 9, 2000, to Gellman et al. and incorporated herein by reference. A "β-peptide" is a polyamide comprising β-amino acid residues.

The term "cyclically-constrained," when applied to β-amino acids and residues, designates that the α and β backbone carbon atoms of each β-amino acid or residue are incorporated into a $C_3$–$C_{10}$ cycloalkyl, cycloalkenyl, aryl, or hetercyclic ring.

All stereochemical configurations (single enantiomers, single diastereomers, mixtures thereof, and racemates thereof) of the compounds described herein are encompassed within the scope of the invention. In the preferred embodiments, all of the residues share the same absolute configuration (either R or S) about the asymmetric ring carbon in the position P to the exocyclic carbonyl carbon, when the conjugate contains residues that are cyclic imino carboxylic acids.

As used in the specification and the claims, the word "independently," when referring to the nature of a variable substituent, explicitly means that each appearance of the defined substituent within a molecule can be different. Thus, for example, in a molecule according to the present invention such as A-$X_3$-$Z_3$-B (wherein A is hydrogen, and B is hydroxy), each appearance of X and each appearance of Z can vary independently within the molecule. Thus, according to this explicit definition, the molecule A-$X_3$-$Z_3$-B explicitly encompasses the molecule A-X'-X''-X'''-Z'-Z''-Z'''-B, where X' may the same as or different from X'', and X'' may be the same as or different from X'''. Likewise, Z' may the same as or different from Z'', and Z'' may be the same as or different from Z'''.

As used herein, the terms "amino-terminus protecting group" and "carboxy-terminus protecting group" refer to any chemical moiety capable of addition to and (optionally) removal from a reactive site (an amino group and a carboxy group, respectively, in this instance) to allow manipulation of a chemical entity at sites other than the reactive site. Protecting groups, and the manner in which they are introduced and removed are described, for example, in "Protective Groups in Organic Chemistry," Plenum Press, London, N.Y. 1973; and in "Methoden der organischen Chemie," Houben-Weyl, 4th edition, Vol. 15/1, Georg-Thieme-Verlag, Stuttgart 1974; and in Theodora W. Greene, "Protective Groups in Organic Synthesis," John Wiley & Sons, New York 1981. A characteristic of many protecting groups is that they can be removed readily, i.e., without the occurrence of undesired secondary reactions, for example by solvolysis, reduction, photolysis or alternatively under physiological conditions.

A host of protecting groups are known in the art. An illustrative, non-limiting list of protecting groups includes methyl, formyl, ethyl, acetyl, t-butyl, benzyl, trifluoroacetyl, t-butoxycarbonyl, benzoyl, 4-methylbenzyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5, 7,8-pentamethyl-chroman-6-sulphonyl. The terms "amino-terminus protecting group" and "carboxy-terminus protecting group" as used herein are explicitly synonymous with such terms as "N-terminal capping group" and "C-terminal capping group," respectively. A host of suitable protecting and capping groups, in addition to those described above, are known in the art. For discussions of various different types of amino- and carboxy-protecting groups, see, for example, U.S. Pat. No. 5,221,736 (issued Jun. 22, 1993); U.S. Pat. No. 5,256,549 (issued Oct. 26, 1993); U.S. Pat. No. 5,049,656 (issued Sep. 17, 1991); and U.S. Pat. No. 5,521, 184 (issued May 28, 1996).

Regarding salts of the subject compounds, compounds having at least one basic group or at least one basic radical, for example a free amino group, a free guanidino group, a pyrazinyl radical, or a pyridyl radical, may form acid addition salts. Thus, the invention encompasses acid addition salts of the subject compounds with (for example)

inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid. When several basic groups are present mono- or poly-acid addition salts may be formed.

As used herein, the terms alkyl, alkenyl, and alkynyl explicitly encompass linear, branched and/or cyclic moieties, including mono- and bicyclic moieties. In the case of disubstituted amine, amide and carboxamide moieties (e.g., a di-$C_1$–$C_6$-alkyl-substituted amine), the disubstitution explicitly encompasses substitution patterns wherein the nitrogen atom defines part of a heterocyclic ring.

When the subject compounds have acidic groups, for example a free carboxy group, the invention encompasses metal and ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethylpiperidine or N,N'-dimethyl-piperazine.

Compounds of the present invention having both acidic and basic groups can form internal salts. The salts may be pharmaceutically-acceptable salts or pharmaceutically-unacceptable salts.

The cyclically-constrained β-amino acid residues that can be utilized in the present invention include those disclosed in U.S. Pat. No. 6,060,585, issued May 9, 2000, to Gellman et al., and incorporated herein by reference. Additionally, β-amino acid residues such as those disclosed in co-pending application Ser. No. 09/502,829, to Gellman et al. (incorporated herein), may also be used in the present invention. Further still, cyclic imino carboxylic acids and gem-di-substituted cyclic imino carboxylic acids (both of which are a type of cyclically-constrained β-amino acid) can also be used in the invention. Preferably, these residues take the form of the individual residues disclosed in co-pending application Ser. No 09/592,769, to Gellman et al., incorporated herein by reference.

Further still, these β-residues may also take the form of the gem-di-substituted cyclic imino acids disclosed in co-pending application Ser. No. 09/883,579, to Gellman & Huck, incorporated herein by reference.

Chemistry:

General: Melting points are uncorrected. $CH_2Cl_2$ was freshly distilled from $CaH_2$ under $N_2$. DMF was distilled under reduced pressure from ninhydrin and stored over 4 Å molecular sieves. Triethylamine was distilled from $CaH_2$ before use. Other solvents and reagents were used as obtained from commercial suppliers. For BOC removal, 4 M HCl in dioxane from was used. Column chromatography was carried out by using low air pressure (typically 6 psi) with 230–400 mesh silica gel 60. Routine $^1$H-NMR spectra were obtained on a Bruker AC-300 and are referenced to residual protonated NMR solvent. Routine $^{13}$C-NMR spectra were obtained on a Bruker AC-300 and are referenced to the NMR solvent. High resolution electron impact mass spectroscopy was performed on a Kratos MS-80RFA spectrometer with DS55/DS90.

Far UV Circular Dichroism (CD): Data were obtained on a Jasco J-715 instrument at 20° C. In all CD plots contained herein, the mean residue ellipticity is presented on the vertical axis. Presenting the mean residue ellipticity is a standard practice in peptide chemistry wherein the intensity of each CD spectrum is normalized for the number of amide chromophores in the peptide backbone. Consequently, when the intensities of the maximum and minimum peaks characteristic of secondary structure formation increase with increasing chain length, this change represents an increase in the population of the secondary structure, rather than simply an increase in the number of chromophores present in each molecule.

Solid-Phase and Solution-Phase Polypeptide Synthesis: Construction of polypeptides using any type of β-amino acid residue can be accomplished using conventional and widely recognized solid-phase or solution-phase synthesis. Very briefly, in solid-phase synthesis, the desired C-terminal amino acid residue is linked to a polystyrene support as a benzyl ester. The amino group of each subsequent amino acid to be added to the N-terminus of the growing peptide chain is protected with Boc, Fmoc, or another suitable protecting group. Likewise, the carboxylic acid group of each subsequent amino acid to be added to the chain is activated with DCC and reacted so that the N-terminus of the growing chain always bears a removable protecting group. The process is repeated (with much rinsing of the beads between each step) until the desired polypeptide is completed. In the classic route, the N-terminus of the growing chain is protected with a Boc group, which is removed using trifluoracetic acid, leaving behind a protonated amino group. Triethylamine is used to remove the proton from the N-terminus of the chain, leaving a free amino group, which is then reacted with the activated carboxylic acid group from a hew protected amino acid. When the desired chain length is reached, a strong acid, such as hydrogen bromide in trifluoracetic acid, is used to both cleave the C-terminus from the polystyrene support and to remove the N-terminus protecting group.

Solid-phase peptide synthesis is widely employed and well known. Consequently, it will not be described in any further detail here. See, for example, "Peptide Synthesis, Structures, and Applications"© 1995 by Academic Press.

Conventional solution-phase peptide synthesis can also be used with equal success.

β-Amino Acid Residues: Cyclically-constrained β-amino acid residues that can be used in the present invention are exemplified by compounds such as 2-aminocyclohexanecarboxylic acid (ACHC) and 2-aminocyclopentanecarboxylic acid (ACPC). These two structures are shown below:

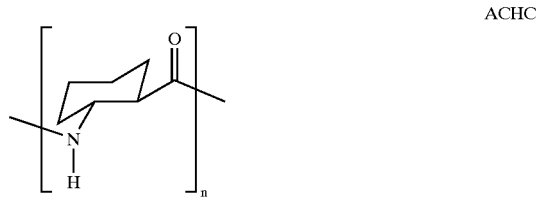

ACHC

ACPC

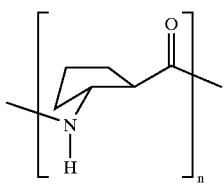

Briefly, for unsubstituted β-amino acids and β-amino acids containing one or two acyclic substituents on the carbon adjacent to the amino group in the product β-peptide, the Arndt-Eistert homologation reaction can be used, see Reaction 1. See also Seebach et al. (1996) *Helv. Chim. Acta* 79:913. A distinct advantage to this route is that the starting materials, α-amino acids, are readily available commercially in enantiomerically pure form. The Arndt-Eistert reaction, however, cannot be used to synthesize β-amino acids having rings in the backbone.

The Arndt-Eistert homologation reaction proceeds via a Wolff rearrangement of a diazoketone, as shown in Reaction 1:

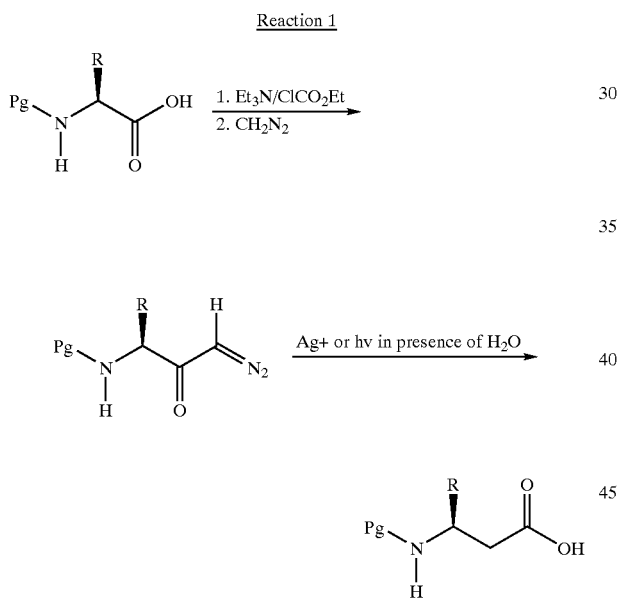

(Pg) designates a protecting group such as (t-butoxy) carbonyl (Boc) or an adjacent β-amino residue, $R^1$ and $R^2$ are aliphatic substituents.

The Arndt-Eistert homologation procedure can also be used to make β-amino acids having an α-position substituent via alkylation of the intermediate α-diazoketone. See Yang et al. (2000), *Org. Lett.* 2:2177:2179.

β-Amino acids containing an unsubstituted cycloalkyl moiety involving the α and β carbons are synthesized using literature methods. See, for example, Nohira et al. (1970) *Bull. Chem. Soc. Jpn.* 43:2230; Herradon and Seebach (1989) *Helv. Chim. Acta* 72:690–714; and Tilley et al. (1992) *J. Med. Chem.* 35:3774–3783, all three of which are incorporated herein by reference. See also Gellman et al., U.S. Pat. No. 6,060,585, issued May 9, 2000, also incorporated herein by reference.

In particular, the cyclohexyl-containing β-amino acids can be synthesized via Reaction 2:

REACTION 2

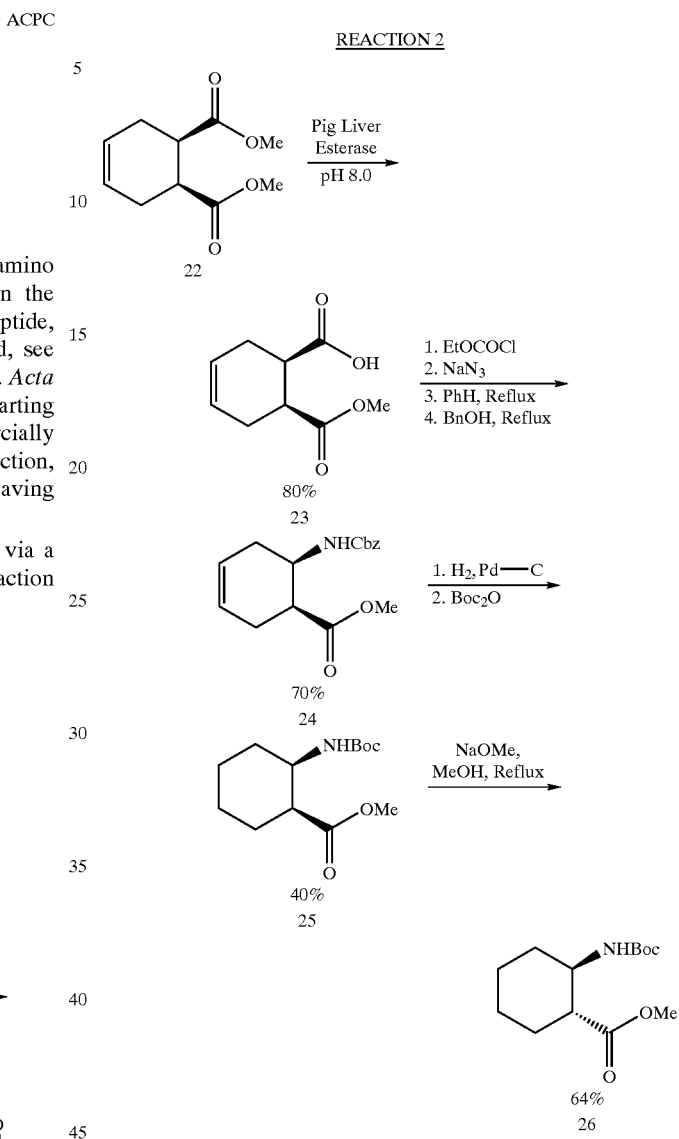

(1R,6S)-6-Methoxycarbonyl-3-cyclohexene-1-carboxylic acid (23): 4600 u of PLE was suspended in pH 8.01 aqueous buffer solution (0.17 M $KH_2PO_4$). The diester 22 (10.1 g, 0.05 mol) was dissolved in 30 mL of acetone and added to the buffer solution. Reaction was allowed to stir at rt overnight. The enzyme was filtered off through a well-packed celite pad, the solution was then acidified to pH 1 with 1M HCl and the product was extracted with ethyl acetate (5×400 mL). The combined organic extracts were dried over anhydrous magnesium sulfate and concentrated to yield 9.00 g yellow oil. Product taken on without further purification.

Methyl (1S,6R)-6-benzyloxycarbonylaminocyclohex-3-ene carboxylate (24): Ethylchloroforamate (4 mL, 0.042 mol) was added to a mixture of 23 (5.14 g, 0.028 mol) and triethylamine (6 mL, 0.043 mol) in acetone (100 mL) at 0° C. and vigorously stirred for 10 min. An aqueous solution of $NaN_3$ (3.04 g, 0.047 mol, in 25 mL water) was added in one portion. The resulting mixture was stirred for 30 min at 0° C. The reaction mixture was diluted with water and extracted with diethyl ether. The organic extracts were dried over anhydrous magnesium sulfate and concentrated without heat to yield a viscous yellow liquid. The liquid was dissolved in 100 mL of benzene and refluxed under nitrogen atmosphere for 30 min. Benzyl alcohol (12 mL, 0.116 mol) was added and solution was refluxed for an additional 16 h. The reaction was cooled to rt and concentrated to yield 17.12 g of a yellow liquid (mixture of benzyl alcohol and desired product in a 5.4:1 ratio, respectively by $^1$H NMR, ~5.67 g product). Mixture taken on without further purification.

Methyl (1S,6R)-6-tert-butoxycarbonylaminocyclohexane carboxylate (25): The yellow oil from the previous reaction, which contains compound 24 (5.6 g, 0.020 mol) and benzyl alcohol, was dissolved in methanol. 0.525 g of 10% Pd on carbon was added to the methanol solution, and the heterogenous mixture was placed under 50 psi $H_2$ and shaken at rt for 24 h. The mixture was filtered through celite, and the filtrate was concentrated to yield 13.74 g of dark golden yellow liquid. 25 mL of 1M HCl was added to the filtrate, and the benzyl alcohol was extracted with diethyl ether (3×25 mL). The pH of the aqueous solution was adjusted to 9 using $K_2CO_3$. 25 mL of dioxane and $Boc_2O$ (5 g, 0.023 mol) were added to the solution, and the reaction was stirred at rt for 20 h. 15 mL of water was added and the solution was extracted with ethyl acetate (3×50 mL). The combined organic extracts were dried over anhydrous magnesium sulfate and concentrated. Residue was purified via column chromatography ($SiO_2$, eluting with 6:1 Hex:EtOAc), to yield 2.00 g viscous clear oil.

Methyl (1R,6R)-6-tert-butoxycarbonylaminocyclohexane carboxylate (26): Sodium metal (0.14 g, 6.1 mmol) was placed into a flame dried flask under nitrogen atmosphere and cooled to 0° C. 10 mL of freshly distilled methanol was added and the mixture stirred until all the sodium dissolved. An amount of 25 (2.00 g, 7.7 mmol) was dissolved in 10 mL of freshly distilled methanol and transferred to NaOMe solution via cannula. The solution was refluxed under nitrogen for 5.5 h, cooled to rt and acidified with 0.5 M aqueous 0.5 M ammonium chloride (18 mL, 9 mmol). The methanol was removed under reduced pressure, and the resulting solid collected by filtration to yield 1.27 g of desired product.

β-Amino acids containing a substituted cycloalkyl moiety were synthesized using the following illustrative protocol, the first four steps of which are described in Kobayashi et al. (1990) *Chem. Pharm. Bull.* (1990) 38:350. The remaining steps to yield a cyclohexyl ring having two differentially protected amino substituents were developed in furtherance of the present invention and have not heretofore been described in the literature and are shown in Reaction 3:

As depicted in Reaction 3, the 4-position amino substituent is protected by a Boc group and the 1-position amino substituent is protected by a Cbz group. The starting material is available commercially (Aldrich Chemical Co., Milwaukee, Wis.).

Synthesis of β-amino acids containing a heterocylic ring moiety encompassing the α and β carbons were synthesized using Reactions 4 and 5, below. Reaction 4 details an illustrative synthesis of a β-proline wherein the exocyclic amino substituent is in the 3-position relative to the ring nitrogen.

Compound 42: Tap water (200 ml) and baker's yeast (25 g) were mixed, and were shaken on an orbital shaker for 1 hour. Compound 41 (1.0 g) was then added. The mixture was shaken at room temperature for 24 hours. The mixture was filtered through a bed of Celite. The Celite was washed with water (20 ml). The filtrate was extracted with diethyl ether (5×100 ml). The extracts were washed with water (2×50 ml), dried over $MgSO_4$, and concentrated to yield a slightly yellow oil. The crude product was purified by column chromatography with ethyl acetate/hexane (1/1, v/v) as eluent to give a colorless oil (0.5 g) in 50% yield.

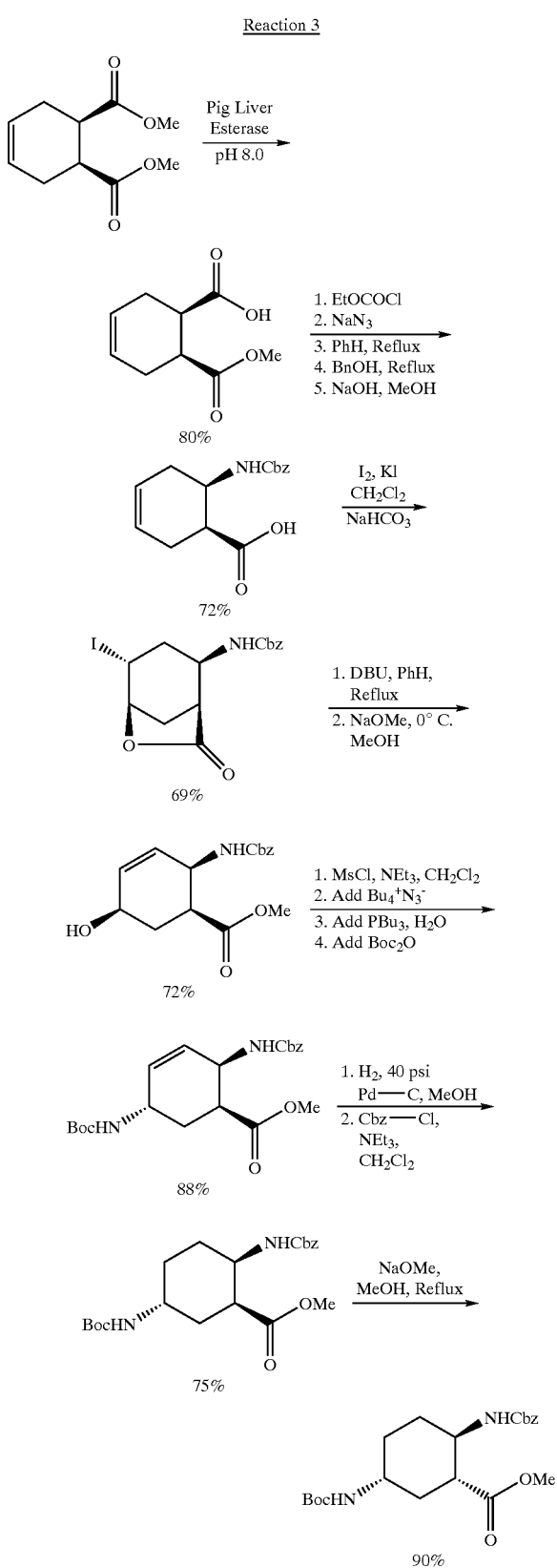

Reaction 3

Reaction 4

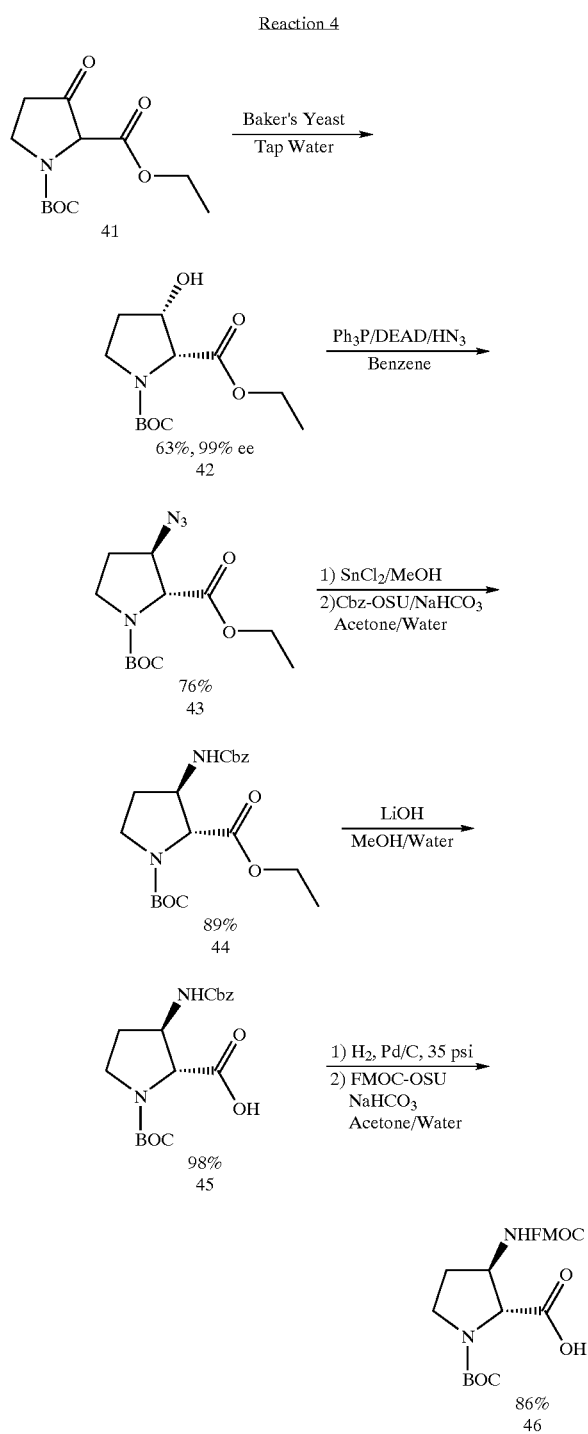

DEAD=Diethyl azodicarboxylate
Cbz-OSU=N-(Benzyloxycarbonyloxy)succinimide
Fmoc-OSU=9-Fluorenylmethyloxycarbonyl-N-hydroxysuccinimide Starting material: Blake, J. et al *J. Am. Chem. Soc.* 1964, 86 5293.

Yeast reduction: Cooper, J. et al *J. Chem. Soc. Perkin Trans.* 1 1993, 1313.

Compound 43: Compound 42 (228 mg) and $Ph_3P$ (346 mg) were dissolved in benzene (anhydrous, 4 ml) under nitrogen. $HN_3$ (1.64 M in benzene, 0.8 ml) was then added. A solution of diethyl azodicarboxylate (0.18 ml) in benzene (1.0 ml) was subsequently introduced via syringe over 5 minutes. The reaction mixture turned cloudy towards the end of the addition. The reaction mixture was stirred under nitrogen at room temperature for 3.0 hours. The reaction mixture was then taken up in ethyl acetate (50 ml), washed with 1N NaOH (10 ml), saturated $NaHCO_3$ (10 ml), and finally dilute brine (5 ml). The organic extract was dried over $MgSO_4$, and concentrated to give a slightly yellow oil. The crude oil was purified by column chromatography with ethyl acetate/hexane (1/1, v/v) as eluent to afford a colorless oil (190 mg) in 76% yield.

Compound 44: Compound 43 (1.1 g) was dissolved in methanol (50 ml). $SnCl_2$ (2.2 g) was then added. The mixture was stirred at room temperature for 30 hours. The methanol was then removed under reduced pressure. The residue was dissolved in methylene chloride (50 ml). The resulting cloudy solution was filtered through Celite. The methylene chloride was then removed under reduced pressure. The residual white solid was dissolved in acetone/water (2/1, v/v, 50 ml). $NaHCO_3$ (3.3 g) was added, followed by Cbz-OSU (1.16 g). The reaction mixture was stirred at room temperature for 24 hours. Water (50 ml) was added. The acetone was removed under reduced pressure. The aqueous mixture was extracted with ethyl acetate (3×100 ml). The extracts were washed with dilute brine (30 ml), dried over $MgSO_4$, and concentrated to give a colorless oil. The crude product was purified by column chromatography with ethyl acetate/hexane (3/7, v/v) as eluent to give the clean product as a colorless oil (1.35 g) in 89% yield.

Compound 45: Compound 44 (1.35 g) was dissolved in methanol/water (3/1, v/v, 80 ml), cooled to 0° C. $LiOH.H_2O$ (1.68 g) was added. The mixture was stirred at 0° C. for 24 hours, by which time TLC indicated that the hydrolysis was complete. Saturated ammonium hydroxide (20 ml) was added. The methanol was removed under reduced pressure. The aqueous was washed with diethyl ether (50 ml), acidified with 1N HCl to pH 3, extracted with methylene chloride (3×150 ml). The extracts were washed with dilute brine (50 ml), dried over $MgSO_4$, concentrated to give a sticky colorless residue (1.25 g, 99%), which was used directly without further purification.

Compound 46: Compound 45 (1.25 g) was dissolved in methanol (50 ml) in a hydrogenation flask. 5% Palladium on activated carbon (190 mg) was added. The flask was pressurized with hydrogen to 35 psi, rocked at room temperature for 7 hours, by which time TLC indicated that the hydrogenolysis was complete. The Pd/C was removed by filtration. The filtrate was concentrated to give a white solid. The white solid was dissolved in acetone/water (2/1, v/v, 70 ml), cooled to 0° C. $NaHCO_3$ (1.7 g) was added, followed by FMOC-OSU (1.39 g). The reaction mixture was stirred at room temperature for 16 hours. Water (50 ml) was added. The acetone was removed under reduced pressure. The aqueous was washed with diethyl ether (50 ml), acidified with 1N HCl to pH 3, extracted with methylene chloride (3×150 ml). The extracts were washed with dilute brine (50 ml), dried over $MgSO_4$, concentrated to give a foamy white solid. The crude white solid was purified by column chromatography with methanol/ethyl acetate (3/7, v/v) as eluent to give the clean product as a white solid (1.3 g) in 86% yield.

Reaction 5 illustrates the synthesis of a β-amino acid wherein the exocyclic amino substituent the nitrogen heteroatom is in the 4-position relative to the ring nitrogen.

Reaction 5

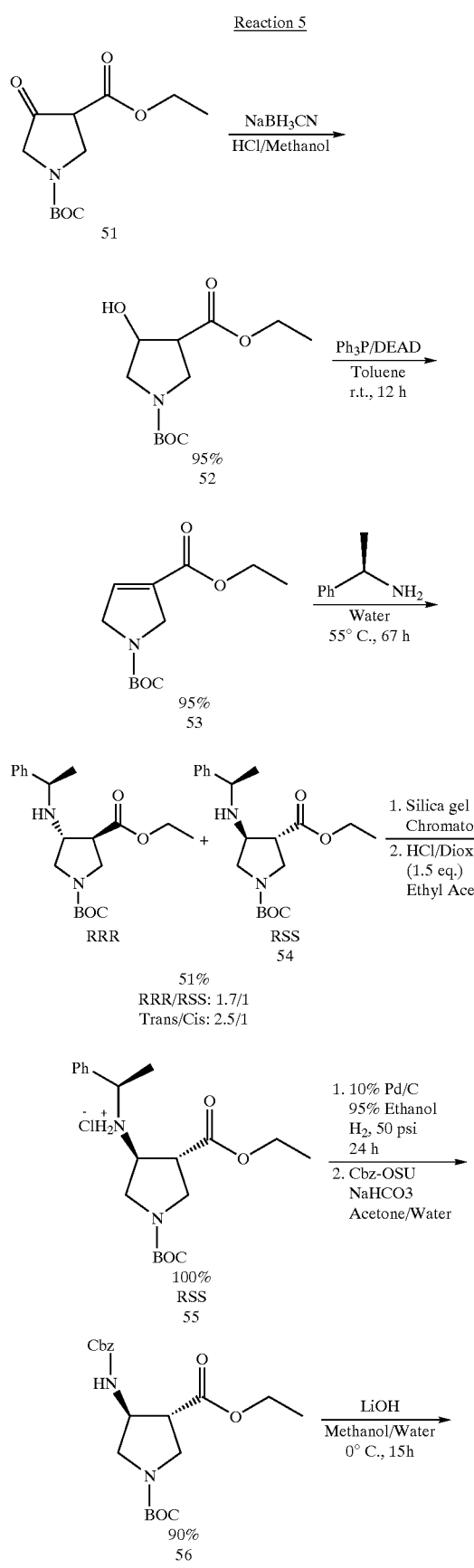

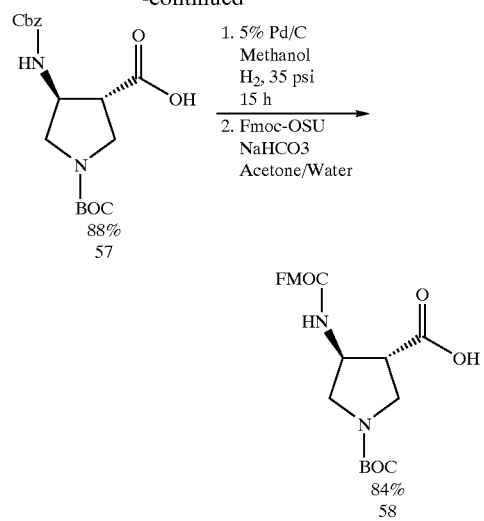

(Starting material: Blake et al. (1964), *JACS* 86:5293)

Compound 52: Compound 51 (2.0 g) and NaBH$_3$CN (0.54 g) were dissolved in methanol (40 ml), 1N HCl (aqueous) was added dropwise to maintain pH 3–4. After 15–20 minutes, pH change slowed. The mixture was stirred for an additional 1.0 hour, while 1N HCl was added occasionally to keep pH 3–4. Water (100 ml) was added. The mixture was extracted diethyl ether (3×150 ml). The extracts were washed with 1N NaHCO$_3$ (100 ml) and dilute brine (100 ml), dried over MgSO$_4$, and concentrated to give a colorless oil (1.9 g) in 95% yield. The product was used directly without further purification.

Compound 53: Compound 52 (1.9 g) and Ph$_3$P (2.8 g) were dissolved in toluene (anhydrous, 30 ml) under nitrogen. A solution of diethyl azodicarboxylate (1.5 ml) in toluene (10 ml) was subsequently introduced via syringe over 15 minutes. The reaction mixture was stirred under nitrogen at room temperature for 12 hours. The toluene was removed under reduced pressure. The residue was purified by column chromatography with ethyl acetate/hexane (3/7, v/v) as eluent to afford a colorless oil (1.6 g) in 91% yield.

Compound 54: Compound 53 (1.0 g) and R-(+)-α-methylbenzylamine (1.1 ml) were mixed with water (15 ml). The mixture was stirred at 55° C. for 67 hours. The mixture was taken up in diethyl ether (300 ml), and the aqueous layer was separated. The ether solution was washed with water (3×50 ml), dried over MgSO$_4$, and concentrated to give a slight yellow oil. The diastereometric isomers were separated by column chromatography with ethyl acetate/hexane (2/8, v/v) as eluent to give RSS (0.2 g) and RRR (0.34 g) in 51% overall yield.

Compound 55: Compound 54 (4.2 g) was dissolved in ethyl acetate (200 ml). 4N HCl in dioxane (4.35 ml) was added dropwise while stirring. A white precipitate resulted. The ethyl acetate was removed under reduced pressure, and the resulting white solid (4.6 g, 100%) was dried in vacuo.

Compound 56: Compound 55 (4.6 g) was dissolved in 95% ethanol (150 ml) in a hydrogenation flask. 10% Palladium on activated carbon (0.5 g) was added. The flask was pressurized with hydrogen to 50 psi, rocked at room temperature for 22 hours, by which time NMR spectroscopy indicated that the hydrogenolysis was complete. The Pd/C was removed by filtration. The filtrate was concentrated to give a white solid. The white solid was dissolved in acetone/water (2/1, v/v, 150 ml). NaHCO$_3$ (9.7 g) was added, followed by Cbz-OSU (3.4 g). The reaction mixture was stirred at room temperature for 14 hours. Water (100 ml) was added. The acetone was removed under reduced pressure. The aqueous mixture was extracted with ethyl acetate (3×200 ml). The extracts were washed with 1N HCl (3×100 ml) and saturated NaHCO$_3$ (aqueous), dried over MgSO$_4$, and concentrated to give a colorless oil. The crude product was purified by column chromatography with ethyl acetate/hexane (3/7, v/v) as eluent to give the clean product as a colorless sticky oil (4.0 g) in 90% yield.

Compound 57: Compound 56 (2.0 g) was dissolved in methanol/water (3/1, v/v, 115 ml), cooled to 0° C., LiOH.H$_2$O (2.4 g) was added. The mixture was stirred at 0° C. for 15 hours, by which time TLC indicated that the hydrolysis was complete. Saturated ammonium hydroxide (aqueous, 100 ml) was added. The methanol was removed under reduced pressure. The aqueous was acidified with 1N HCl to pH 3, extracted with ethyl acetate (3×200 ml). The extracts were washed with dilute brine (100 ml), dried over MgSO$_4$, concentrated to give a foamy solid (1.63 g, 88%), which was used directly without further purification).

Compound 58: Compound 57 (1.63 g) was dissolved in methanol (70 ml) in a hydrogenation flask. 5% Palladium on activated carbon (250 mg) was added. The flask was pressurized with hydrogen to 35 psi, rocked at room temperature for 15 hours, by which time NMR spectroscopy indicated that the hydrogenolysis was complete. The Pd/C was removed by filtration. The filtrate was concentrated to give a white solid. The white solid was dissolved in acetone/water (2/1, v/v, 90 ml), cooled to 0° C. NaHCO$_3$ (2.27 g) was added, followed by FMOC-OSU (1.83 g). The reaction mixture was stirred at 0° C. for 2 hours, then at room temperature for 28 hours. Water (50 ml) was added. The acetone was removed under reduced pressure. The aqueous was acidified with 1N HCl to pH 3, extracted with ethyl acetate (3×200 ml). The extracts were washed with dilute brine (100 ml), dried over MgSO$_4$, concentrated to give a foamy white solid. The crude white solid was purified by column chromatography with methanol/ethyl acetate (3/7, v/v) as eluent to give the clean product as a white solid (1.68 g) in 84% yield.

Solution-phase synthesis of a β-peptide chain containing alternating residues of unsubstituted cyclohexane rings and amino-substituted cyclohexane rings proceeds in conventional fashion as outlined in Reaction 6:

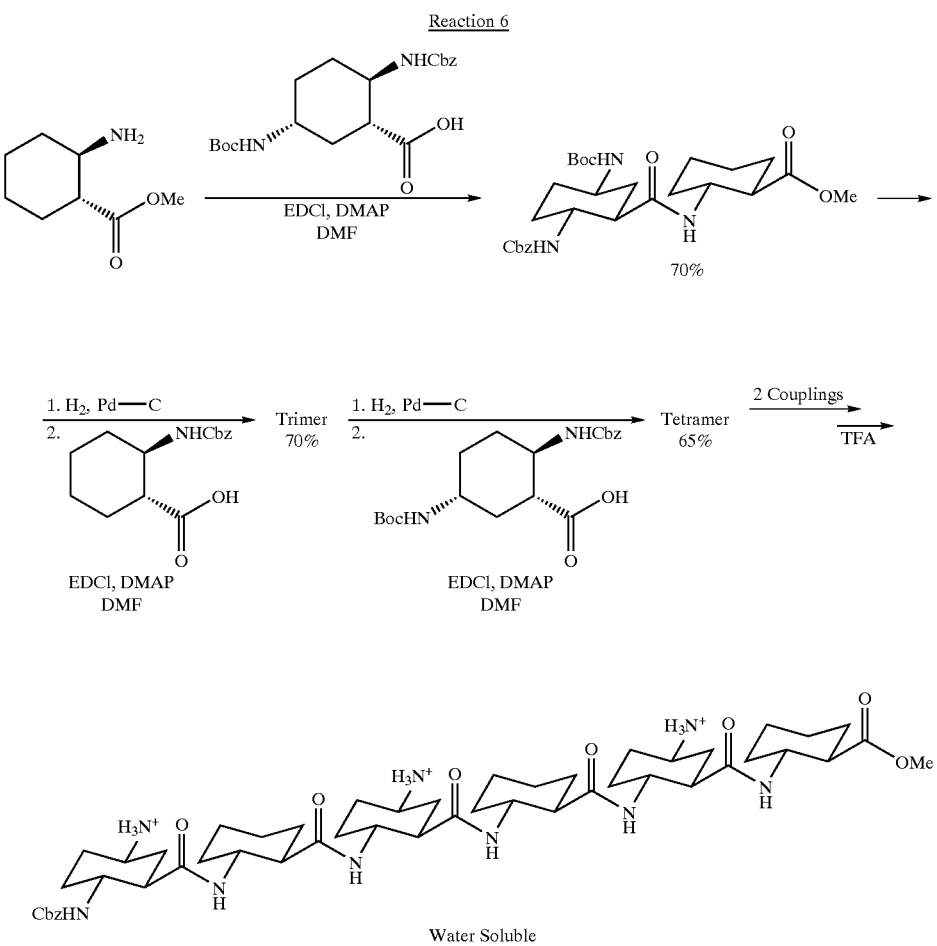

Reaction 6 works with equal success to build peptides wherein the residues are the same or different.

Reaction 7 is an illustration of a homologation reaction combined with conventional solution-phase peptide synthesis, to yield a β-peptide having acyclic-substituted residues alternating with cyclically-constrained residues:

Reaction 7

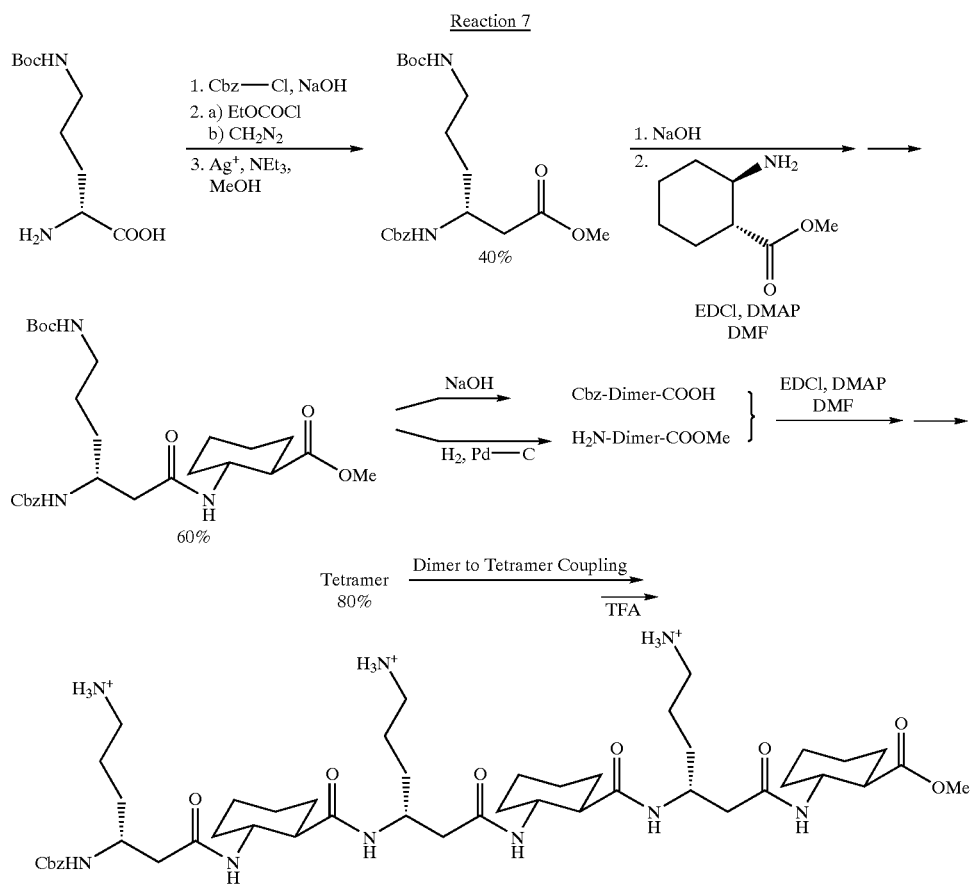

As noted above, the β-peptides of the present invention can be substituted with any number of substituents, including hydroxy, linear or branched $C_1$–$C_6$-alkyl, alkenyl, alkynyl; hydroxy-$C_1$–$C_6$-alkyl, amino-$C_1$–$C_6$-alkyl, $C_1$–$C_6$-alkyloxy, $C_1$–$C_6$-alkyloxy-$C_1$–$C_6$-alkyl, amino, mono- or di-$C_1$–$C_6$-alkylamino, carboxamido, carboxamido-$C_1$–$C_6$-alkyl, sulfonamido, sulfonamido-$C_1$–$C_6$-alkyl, urea, cyano, fluoro, thio, $C_1$–$C_6$-alkylthio, mono- or bicyclic aryl, mono- or bicyclic heteraryl having up to 5 heteroatoms selected from N, O, and S; mono- or bicyclic aryl-$C_1$–$C_6$-alkyl, heteroaryl-$C_1$–$C_6$-alkyl, and combinations thereof. Effecting such substitutions is well within the set of skills possessed by a synthetic peptide chemist.

For example, appending a sulfonamido moiety to the cylic backbone substituent can be accomplished in conventional fashion using Reaction 8.

Compound 63: Compound 61 (90 mg) was dissolved in 4 NHCl in dioxane (2.0 ml). The reaction mixture was stirred for 1.5 hours. The dioxane was then removed in vacuo. The residue was dissolved in pyridine (2.0 ml), then cooled to 0° C. in an ice-bath.

Methanesulfonylchloride (71 µl) was added dropwise. After the addition, the reaction mixture was stirred at room temperature for 12 hours. The pyridine was then removed in vacuo. The residue was taken up in ethyl acetate (50 ml). The mixture was washed with dilute brine (2×10 ml), dried over $MgSO_4$, and concentrated to give the clean product as a colorless oil (70 mg) in 82% yield.

Compound 64: Compound 62 (30 mg) was dissolved in 4 N HCl in dioxane (2.0 ml). The reaction mixture was stirred for 1.5 hours. The dioxane was then removed in vacuo. The residue was dissolved in pyridine (1.0 ml), then cooled to 0° C. in an ice-bath. Toluenesulfonylchloride (63 mg) was added in portions. After the addition, the reaction mixture was stirred at room temperature for 12 tours. The pyridine was then removed in vacuo. The residue was taken up in methylene chloride/dithyl ether (1/1, v/v, 100 ml). The mixture was washed with dilute brine (3×20 ml), dried over $MgSO_4$, and concentrated to give a liquid residue. The crude product was purified by column chromatography with ethyl acetate/hexane (4/6, v/v) as eluent to give the clean

Reaction 8

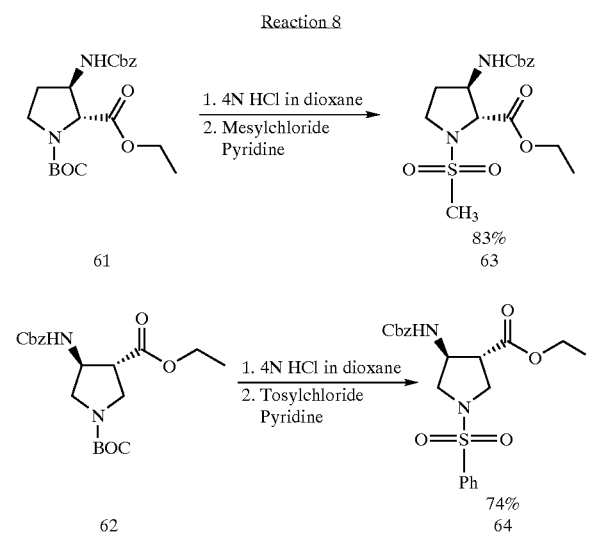

product as a colorless oil (25 g) in 74% yield. Analogous reactions will append a carboxyamido group.

Cyclic Imino Carboxylic Acids: Cyclic imino carboxylic acids are a class of β-amino acid residues wherein the amino functionality itself is part of a ring structure. These β-amino acids can also be used as residues in the present invention.

General Experimental Procedure A. Peptide Couplings Using Bop-Cl as the Coupling Reagent. Boc-Xxx-OBn (1.0 eq.) was dissolved in 4 N HCl/dioxane (2.5 eq.). The solution was stirred for 2 h, the solvent was removed under a stream of N$_2$, and the residue was dried under vacuum to give a white solid (Xxx-OBn-HCl). This material was dissolved in methylene chloride (0.1 M). Boc-Xxx-OH (1.0 eq.) was added and the reaction mixture was cooled to 0 C. BopCl (1.0 eq.) was added, followed by DIEA (2.0 eq.). The reaction mixture was stirred for 48 h at 5 C in the cold room. The reaction mixture was removed from the cold room and poured into a solution of diethyl ether (3× reaction volume) and H$_2$O (2× reaction volume). The organic layer was isolated and washed with saturated KHSO4, saturated NaHCO$_3$, and brine. The organic layer was dried over MgSO$_4$ and concentrated. The crude product was then purified by column chromatography to give Boc-(Xxx)$_2$-OBn.

General Experimental Procedure B. Peptide Couplings Using Bop-Cl as the Coupling Reagent. Boc-Xxx-OBn (1.0 eq.) was dissolved in 4 N HCl/dioxane (2.5 eq.). The solution was stirred for 2 h, the solvent was removed under a stream of N$_2$, and the residue was dried under vacuum to give a white solid (Xxx-OBn-HCl). This material was dissolved in methylene chloride (0.2 M). Boc-Xxx-OH (1.0 eq.) was added and the reaction mixture was cooled to 0 C. BopCl (1.0 eq.) was added, followed by DIEA (2.5 eq.). The reaction mixture was stirred for 48 h at room temperature. The reaction mixture was poured into a solution of diethyl ether (3×reaction volume) and H$_2$O (2× reaction volume). The organic layer was isolated and washed with saturated KHSO4, saturated NaHCO$_3$, and brine. The organic layer was dried over MgSO$_4$ and concentrated. The crude product was then purified by column chromatography to give Boc-(Xxx)2-OBn.

Nipecotic Acid Oligomers

1. Synthesis of the Protected Monomer

Boc-(S)-Nip-OBn or Boc-(R)-Nip-OBn is the building block for the synthesis of nipecotic acid oligomers. The protected monomer was synthesized in three steps beginning with a resolution via co-crystallization with (+) or (−) CSA. The amino group was then protected as the tert-butyl carbamate, and the carboxyl group was protected as the benzyl ester.

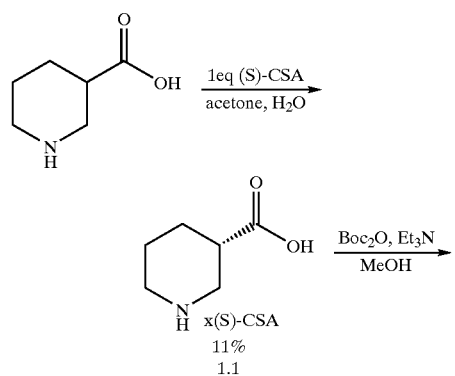

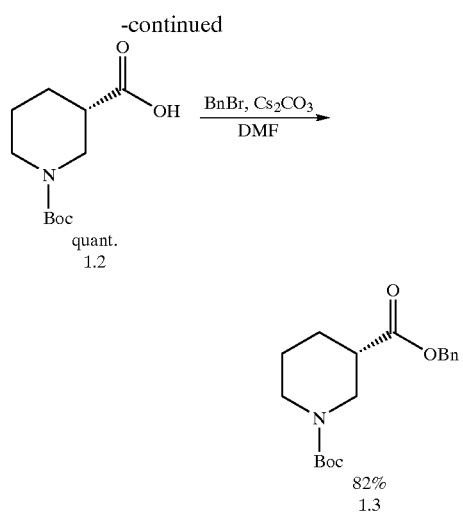

(S)-Nip-(S)-CSA 1.1. (1S)-(+)-10-Camphorsulfonic acid (11.62 g, 0.05 mol) was added to a stirred solution of racemic nipecotic acid (6.46 g, 0.05 mol) in acetone (100 mL). The solution was heated to reflux, and H$_2$O (15 mL) was added until all solids dissolved. The solution was cooled to room temperature and allowed to stir overnight. The precipitate that formed was isolated by filtration and recrystallized three times with acetone/H$_2$O (6/1, v/v) to afford 1.99 g (11% yield) of the desired product as a white solid: m.p. 221–223° C.; {a}D+25.30 (c 1.0, MeOH).

Boc-(S)-Nip-OH 1.2. (S)-Nip-(S)-CSA (1.90 g, 5.3 mmol) was dissolved in methanol (12 mL). Triethylamine (2.2 mL, 15.8 mmol) and di-tert-butyl dicarbonate (1.38 g, 6.3 mmol) were added and the solution was stirred at 50 C for 12 h. The solution was then concentrated, and the residue was dissolved in H$_2$O. The aqueous solution was washed with diethyl ether, and the organic layer was discarded. The aqueous layer was acidified to pH 3 with 1 M HCl and extracted with CH$_2$Cl$_2$. The organic layer was dried over MgSO$_4$ and concentrated to afford 1.24 g (quantitative yield) of the desired product as a white solid: m.p. 166–168° C.; FAB-MS m/z (M$^+$Na$^+$) calcd for C11H19NO4Na 252.3, obsd 252.5.

Boc-(S)-Nip-OBn 1.3. Boc-(S)-Nip-OH (0.70 g, 3.1 mmol) was dissolved in N,N-dimethylformamide (DMF) (14 mL). Cs$_2$CO$_3$ (1.0 g, 3.1 mmol) and benzyl bromide (0.41 mL, 3.5 mmol) were added, and the solution was stirred at room temperature for 24 h. The solution was then concentrated, and the residue was dissolved in H$_2$O. The aqueous solution was then extracted with CH$_2$Cl$_2$. The organic solution was dried over MgSO$_4$ and concentrated to give an oil. The crude product was purified by column chromatography eluting with ethyl acetate/hexanes (1/3, v/v) to afford 0.81 g (82% yield) of the desired product as a white solid.

2. Oligomer Synthesis

Oligomers of nipecotic acid were synthesized in a step-wise fashion using standard coupling procedures:

The reaction scheme is as follows:

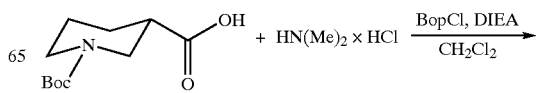

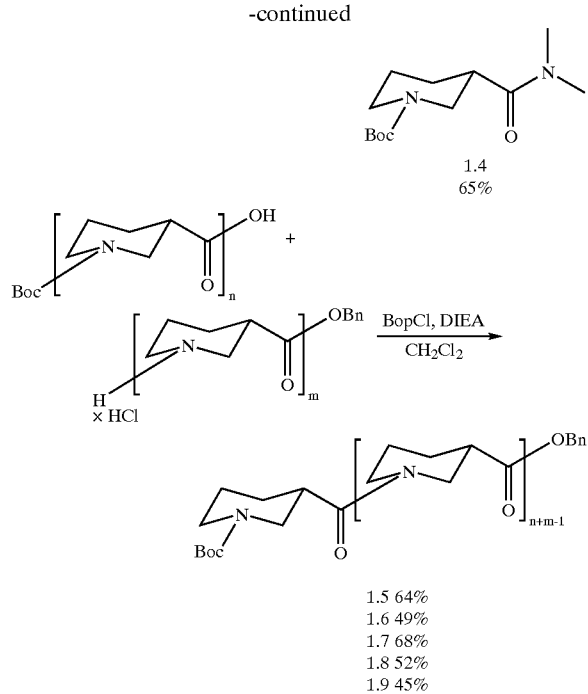

1.4 65%

1.5 64%
1.6 49%
1.7 68%
1.8 52%
1.9 45%

Boc-(S)-Nip-N(Me)$_2$ 1.4. Via general procedure A, HCl-N(Me)$_2$ (0.29 g, 3.5 mmol) was coupled with Boc-(S)-Nip-OH (0.4 g, 1.7 mmol). After workup, the crude product was purified by column chromatography eluting with ethyl acetate/hexanes (1/1, v/v) to afford 0.29 g (65% yield) of the desired product as a colorless oil; FAB-MS m/z (M$^+$Na$^+$) calcd for C$_{11}$H$_{19}$NO$_4$Na+279.3, obsd 279.1.

Boc-{(S)-Nip}$_2$-OBn 1.5. Via general procedure A, Boc (S)-Nip-OBn (0.80 g, 2.5 mmol) was Boc-deprotected and coupled with Boc-(S)-Nip-OH (0.64 g, 2.5 mmol). After workup, the crude product was purified by column chromatography eluting with ethyl acetate/hexanes (1/1, v/v) to afford 0.69 g (64% yield) of the desired product as a colorless oil; MALDI-TOF-MS m/z (M$^+$Na$^+$) calcd for C$_{24}$H$_{34}$N$_2$O$_5$Na$^+$ 453.5, obsd 453.3.

Boc-{(S)-Nip}$_3$-OBn 1.6. Via general procedure A, Boc {(S)-Nip-}2OBn (0.37 g, 0.85 mmol) was Boc-deprotected and coupled with Boc-(S)-Nip-OH (0.19 g, 0.85 mmol). After workup, the crude product was purified by column chromatography eluting with ethyl acetate/methanol (10/1, v/v) to afford 0.22 g (49% yield) of the desired product as a white foam; MALDI-TOF-MS m/z (M$^+$ Na$^+$) calcd for C$_{30}$H$_{43}$N$_3$O$_6$Na$^+$ 564.3, obsd 564.3.

Boc-{(S)-Nip}$_4$-OBn 1.7. Via general procedure A, Boc {(S)-Nip-}$_2$OBn (0.29 g, 0.62 mmol) was Boc-deprotected and coupled with Boc-{(S)-Nip}$_2$-OH (0.29 g, 0.85 mmol). After workup, the crude product was purified by column chromatography eluting with ethyl acetate/methanol (10/1, v/v) to afford 0.27 g (68% yield) of the desired product as a white foam; MALDI-TOF-MS m/z (M$^+$ Na$^+$) calcd for C$_{36}$H$_{52}$N$_4$O$_7$Na+675.4, obsd 675.4.

Boc-{(S)-Nip}$_5$-OBn 1.8. Via general procedure A, Boc-(S)-Nip-OBn (88.4 mg, 0.28 mmol) was Boc-deprotected and coupled with Boc-{(S)-Nip}$_4$-OH (0.14 g, 0.28 mmol). After workup, the crude product was purified by column chromatography eluting with ethyl acetate/methanol (10/1, v/v) to afford 0.11 g (52% yield) of the desired product as a white foam; MALDI-TOF-MS m/z (M$^+$ Na$^+$) calcd for C$_{42}$H$_{61}$N$_5$O$_8$Na$^+$ 786.4, obsd 786.5.

Boc-{(S)-Nip}$_6$-OBn 1.9. Via general procedure A, Boc {(S)-Nip-}$_2$OBn (0.46 g, 1.1 mmol) was Boc-deprotected and coupled with Boc-{(S)-Nip}$_4$-OH (0.16 g, 0.3 mmol). After workup, the crude product was purified by column chromatography eluting with ethyl acetate/methanol (10/1, v/v) to afford 0.12 g (45% yield) of the desired product as a white foam; MALDI-TOF-MS m/z (M$^+$ N$^+$) calcd for C$_{48}$H$_{70}$N$_6$O$_9$Na$^+$ 897.5, obsd 897.6.

Circular dichroism data for 0.5 mM Nip pentamer in isopropanol as a function of temperature indicate that the Nip oligomers are thermally stable, and that only at 75° C. does the stability of the oligomer decrease (data not shown). Circular dichroism data for 0.5 mM Nip hexamer (25° C.) protected in methanol and deprotected in H$_2$O, pH=7.6 suggest that the same secondary structure is adopted in H$_2$O, with there being a small decrease in the stability of the structure (data not shown).

Pyrrolidine-3-Carboxylic Acid (PCA)
1. Synthesis of the Protected Monomer

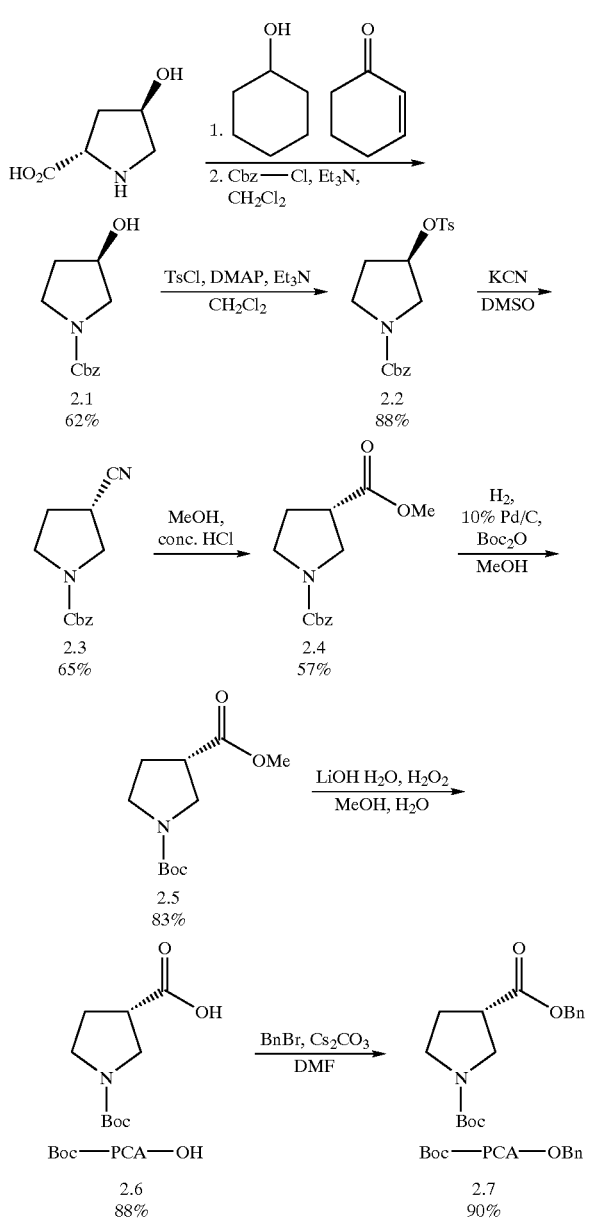

2.1 62%
2.2 88%
2.3 65%
2.4 57%
2.5 83%
2.6 88%
2.7 90%

The synthesis of this monomer is an extension of that given in Klein et al. (1997), Bio. & Med. Chem. Let. 7:1773.

3-Hydroxy-(R)-Pyrrolidine. trans-4-Hydroxy-L-proline (13.11 g, 0.1 mol) was added to cyclohexanol (65 mL), followed by the addition of 2-cyclohexene-1-one (0.65 mL). The reaction mixture was heated at 180° C. until all solids were dissolved. The solution was cooled to room temperature and concentrated by vacuum rotary evaporation. The crude product was carried on to the next synthetic step without further purification.

3-Hydroxy-Cbz-(R)-Pyrrolidine 2.1. 3-Hydroxy-(R)-pyrrolidine (8.71 g, 0.1 mol) was dissolved in CH$_2$Cl$_2$ (260 mL) and cooled to 0° C. Triethylamine (33.5 mL, 0.24 mol) and benzyl chloroformate (14.9 mL, 0.11 mol) were added, and the resulting solution was stirred for 2 h at 0° C. The solution was gradually warmed to room temperature and allowed to stir overnight. The solution was washed with 1 M HCl, saturated NaHCO$_3$, and brine. The organic solution was dried over MgSO$_4$ and concentrated. The crude product was purified by column chromatography eluting with ethyl acetate to afford 13.7 g (62% yield, 2 steps) of the desired product as a purple oil.

3-Tosyl-Cbz-(R)-Pyrrolidine 2.2. 3-Hydroxy-Cbz-(R)-pyrrolidine (13.7 g, 0.06 mol) was dissolved in CH$_2$Cl$_2$ (250 mL) and cooled to 0° C. p-Toluenesulfonyl chloride (14.16 g, 0.07 mol), and triethylamine (20.7 mL, 0.15 mol) were added and the resulting solution was stirred for 4 h at 0° C. The solution was washed with 1 M HCl, saturated NaHCO$_3$, and brine. The organic solution was dried over MgSO$_4$ and concentrated. The crude product was purified by column chromatography eluting with ethyl acetate/hexanes (3/1, v/v) to afford 20.4 g (88% yield) of the desired product as an oil.

3-Cyano-Cbz-(S)-Pyrrolidine 2.3. 3-Tosyl-Cbz-(R)-pyrrolidine (20.4 g, 0.05 mol) was dissolved in DMSO (54 mL), followed by the addition of KCN (5.3 g, 0.08 mol). The reaction mixture was stirred for 5 h at 80° C. The solution was cooled to room temperature and brine/H$_2$O (90 mL) (1/1, v/v) was added. The aqueous solution was extracted with ethyl acetate. The organic extracts were dried over MgSO$_4$, and concentrated. The crude product was purified by column chromatography eluting with ethyl acetate/hexanes (1/1, v/v) to afford 8.13 g (65% yield) of the desired product as an oil.

Cbz-(S)-PCA-OMe 2.4. 3-Cyano-Cbz-(S)-pyrrolidine (8.13 g, 35.3 mmol) was dissolved in methanol (35 mL), followed by the addition of concentrated HCl (35 mL). The solution was stirred for 3 days at room temperature. The solution was neutralized by NaHCO$_3$. The methanol was removed and the solution was diluted with H$_2$O (100 mL). The aqueous solution was extracted with CH$_2$Cl$_2$. The organic extracts were dried over MgSO$_4$ and concentrated. The crude product was purified by column chromatography eluting with ethyl acetate/hexanes (1/1, v/v) to afford 5.26 g (57% yield) of the desired product as a colorless oil.

Boc-(S)-PCA-OMe 2.5. Cbz-(S)-PCA-OMe (5.26 g, 20.0 mmol) was dissolved in methanol (0.1 M), 10% Pd/C (12% vol), and Boc$_2$O (5.67 g, 25.9 mmol) were added, and the solution was shaken on a Parr appartus for 12 h under pressurized H$_2$. The solution was filtered through a plug of glass wool, and the filtrate was concentrated. The crude product was purified by column chromatography eluting with ethyl acetate/hexanes (1/1, v/v) to afford 3.79 g (83% yield) of the desired product as an colorless oil.

Boc-(S)-PCA-OH 2.6. Boc-(S)-PCA-OMe (2.52 g, 11.0 mmol) was dissolved in methanol (155 mL) and H$_2$O (54 mL) and the solution was cooled to 0° C. LiOH.H$_2$O (4.6 g, 0.11 mol) was added, followed by H$_2$O$_2$ (6.23 mL, 0.05 mol) and the solution was stirred for 15 h in the cold room at 5° C. While still cold, Na$_2$SO$_3$ (21 g, 0.17 mol) in H$_2$O (93 mL) was added. The methanol was removed and the solution was brought to pH 2 with 1 M HCl. The aqueous solution was extracted with methylene chloride. The organic extracts were dried over MgSO$_4$ and concentrated to afford 2.36 g (88% yield) of the desired product as a white solid.

Boc-(S)-PCA-OBn 2.7. Boc-(S)-PCA-OH (1.07 g, 4.9 mmol) was dissolved in DMF (50 mL). Cs$_2$CO$_3$ (1.62 g, 4.9 mmol) and benzyl bromide (0.63 mL, 5.2 mmol) were added, and the solution was stirred for 24 h at room temperature. The solution was then concentrated, and the residue was dissolved in H$_2$O. The aqueous solution was then extracted with ethyl acetate. The organic solution was dried over MgSO$_4$ and concentrated. The crude product was purified by column chromatography eluting with ethyl acetate/hexanes (1/3, v/v) to afford 1.52 g (90% yield) of the desired product as a white solid.

2. Oligomer Synthesis

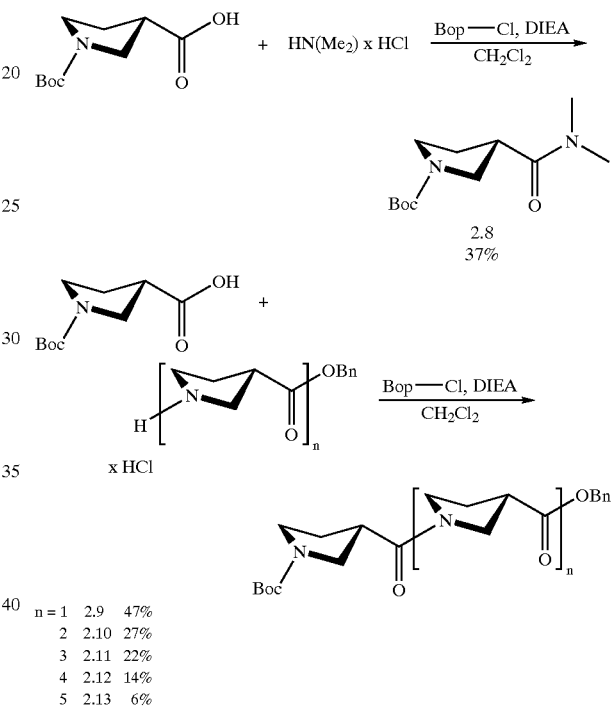

n = 1   2.9   47%
2   2.10   27%
3   2.11   22%
4   2.12   14%
5   2.13   6%

Boc-(S)-PCA-N(Me)$_2$ 2.8. Via general procedure A, HCl-N(Me)$_2$ (31.7 mg, 0.5 mmol) was coupled with Boc-(S)-PCA-OH (93.5 mg, 0.4 mmol). After workup, the crude product was purified by column chromatography eluting with ethyl acetate/hexanes (1/1, v/v) to afford 39.1 mg (37% yield) of the desired product as a colorless oil.

Boc-{(S)-PCA}$_2$-OBn 2.9. Via general procedure A, Boc-(S)-PCA-OBn (0.46 g, 1.5 mmol) was Boc-deprotected and coupled with Boc-(S)-PCA-OH (0.32 g, 1.5 mmol). After workup, the crude product was purified by column chromatography eluting with ethyl acetate/hexanes (3/1, v/v) to afford 0.28 g (47% yield) of the desired product as a colorless oil.

Boc-{(S)-PCA}$_3$-OBn 2.10. Via general procedure A, Boc-{(S)-PCA}$_2$-OBn (90 mg, 0.2 mmol) was Boc-deprotected and coupled with Boc-(S)-PCA-OH (48 mg, 0.2 mmol). After workup, the crude product was purified by column chromatography eluting with ethyl acetate/methanol (20/1, v/v) to afford 29.8 mg (27% yield) of the desired product as an colorless oil.

Boc-{(S)-PCA}$_4$-OBn 2.11. Via general procedure A, Boc-{(S)-PCA}$_2$-OBn (0.21 g, 0.5 mmol) was Boc-deprotected and coupled with Boc-{(S)-PCA}$_2$-OH (0.16 g, 0.5 mmol). After workup, the crude product was purified by column chromatography eluting with ethyl acetate/methanol (20/1, v/v) to afford 67.9 mg (27% yield) of the desired product as a white foam; MALDI-TOF-MS m/z (M+) calcd for $C_{32}H_{44}N_4O_7Na$ 620.724, obsd 620.5.

Boc-{(S)-PCA}$_5$-OBn 2.12. Via general procedure A, Boc-{(S)-PCA}$_3$-OBn (0.10 g, 0.2 mmol) was Boc-deprotected and coupled with Boc-(S)-PCA-OH (36 mg, 0.2 mmol). After workup, the crude product was purified by column chromatography eluting with methylene chloride/methanol (20/1, v/v) to afford 16.3 mg (14% yield) of the desired product as a clear, glassy solid; MALDI-TOF-MS m/z (M+) calcd for $C_{37}H_{51}N_5O_8Na$ 716.841, obsd 716.5.

Boc-{(S)-PCA}$_6$-OBn 2.13. Via general procedure A, Boc-{(S)-PCA}$_4$-OBn (0.10 g, 0.2 mmol) was Boc-deprotected and coupled with Boc-{(S)-PCA}$_2$-OH (52 mg, 0.2 mmol). After workup, the crude product was purified by column chromatography eluting with methylene chloride/methanol (20/1, v/v) to afford 7.0 mg (6% yield) of the desired product as a clear, glassy solid; MALDI-TOF-MS m/z (M+) calcd for $C_{42}H_{58}N_6O_9Na$ 813.957, obsd 813.5.

Piperazine Carboxylic Acid (PiCA)
1. Synthesis of the protected monomer
The synthesis of this monomer is an extension of that given in Patel et al. (1997), J. Org. Chem. 62:6439:

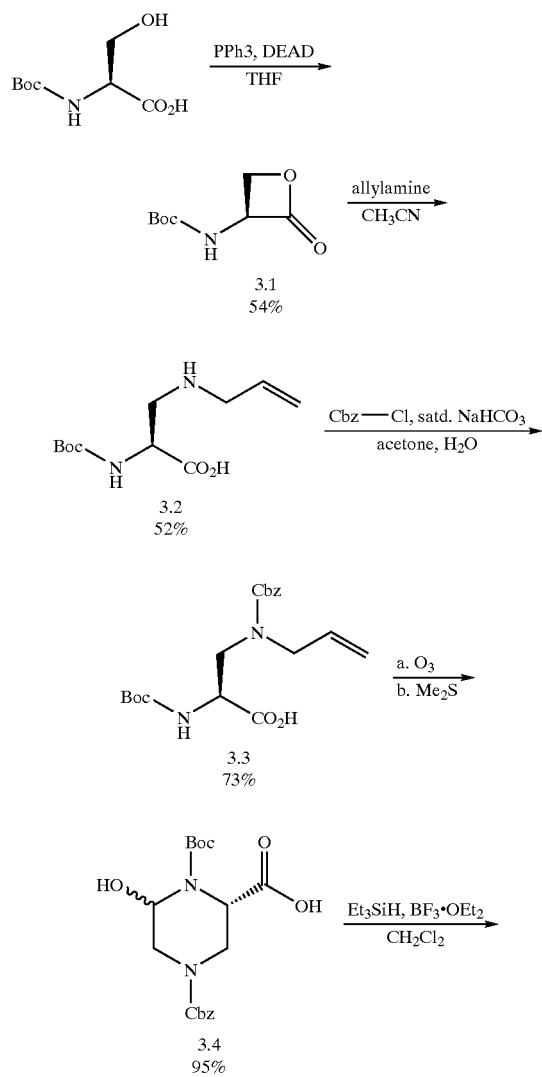

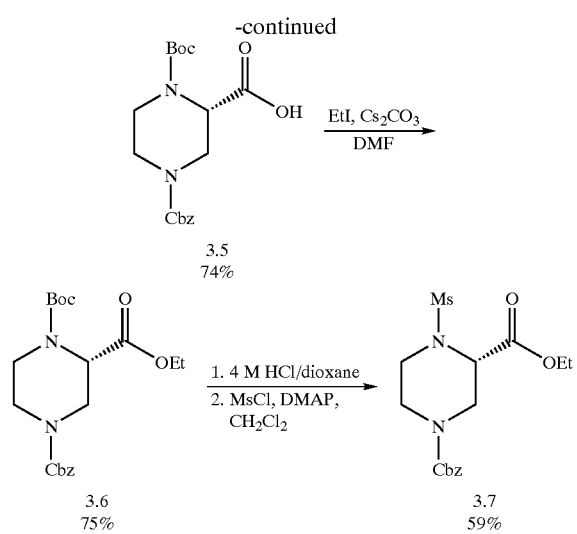

N-tert-Butoxycarbonyl-L-Serine-β-Lactone 3.1. A solution of triphenylphosphine (7.48 g, 28.5 mmol) in anhydrous THF (110 mL) was stirred under $N_2$, cooled to 78° C., and dimethylazodicarboxylate (4.83 mL, 30.7 mmol) was added dropwise. The mixture was stirred for 10 min, and a solution of Boc-serine (4.5 g, 21.9 mmol) in THF (110 mL) was added dropwise. After the addition, stirring was continued at 78° C. for 30 min, and for an additional 3 h after the cooling bath had been removed. The solution was concentrated, and the residue was purified by column chromatography eluting with hexanes/ethyl acetate (2/1, v/v) to afford 2.21 g (54% yield) of the desired product as a white solid.

(S)-N2-(tert-Butoxycarbonyl)-N3-(2-propenyl)-2,3-diaminopropanoic acid 3.2. A N-tert-Butoxycarbonyl-L-serine-β-lactone (2.21 g, 11.8 mmol) in acetonitrile (224 mL) was added dropwise to a stirred solution of allylamine (21.9 mL, 0.29 mmol) in acetonitrile (448 mL). The solution was stirred for 2 h at room temperature and then concentrated. The solid residue was slurried with acetonitrile and filtered to afford 1.51 g (52% yield) of the desired product as a white solid.

(S)-N2-(tert-Butoxycarbonyl)-N3-(benzyloxycarbonyl)-N3-(2-propenyl)-2,3-diaminopropanoic acid 3.3. A solution of (S)-N2-(tert-Butoxycarbonyl)-N3-(2-propenyl)-2,3-diaminopropanoic acid (2.80 g, 11.4 mmol) in saturated $NaHCO_3$ (36 mL) and $H_2O$ (5 mL) was treated dropwise with a solution of benzyl chloroformate (1.84 mL, 12.8 mmol) in acetone (2.5 mL). The cloudy reaction mixture was stirred for 2 h. The resulting solution was partitioned between diethyl ether (130 mL) and $H_2O$ (65 mL). The aqueous layer was cooled in an ice bath, brought to pH 2 with 1 M HCl, and extracted with ethyl acetate. The organic extracts were dried over $MgSO_4$ and concentrated to afford 3.15 g (73% yield) of the desired product as a colorless oil.

(S)-N1-(tert-butoxycarbonyl)-N4-(benzyloxycarbonyl)-Piperazine Carboxylic Acid 3.5. A solution of (S)-N2-(tert-Butoxycarbonyl)-N3-(benzyloxycarbonyl)-N3-(2-propenyl)-2,3-diaminopropanoic acid (3.15 g, 8.3 mmol) in methylene chloride (110 mL) and methanol (11 mL) was cooled to −78° C. under $N_2$. Ozone was passed through the solution until a pale blue color persisted (6 psi $O_2$, 90 V, 20 min). The excess ozone was purged by bubbling $N_2$ through the solution for 15 min. Dimethyl sulfide (11 mL) was added, and the solution was allowed to warm gradually to room temperature overnight. After 20 h, the reaction mixture was diluted with methylene chloride (200 mL) and washed with brine. The organic layer was dried over MgSO₄ and concentrated to afford 3.02 g (95% yield) of the desired product as a yellow foam.

The crude material and triethylsilane (1.4 mL, 8.8 mmol) in methylene chloride (200 mL) under N₂ were cooled to −78° C. and treated dropwise with boron trifluoride diethyl etherate (1.11 mL, 8.8 mmol). After 30 min, more triethylsilane (1.4 mL, 8.8 mmol) and boron trifluoride diethyl etherate (1.11 mL, 8.8 mmol) were added in a similar fashion. The reaction mixture was stirred for 2 h at −78° C., brine was added, and the cold mixture was extracted with methylene chloride. The organic extracts were dried over MgSO₄ and concentrated. The crude product was purified by column chromatography eluting with methylene chloride/ethyl acetate/acetic acid (2/1/0.03, v/v/v) to afford 2.13 g (74% yield) of the desired product as a white solid.

(S)-N1-(tert-butoxycarbonyl)-N4-(benzyloxycarbonyl)-Piperazine Ethyl Ester 3.6. (S)-N1-(tert-butoxycarbonyl)-N4-(benzyloxycarbonyl)-piperazine carboxylic acid (4.66 g, 12.8 mmol) was dissolved in DMF (128 mL). Cs₂CO₃ (4.37 g, 13.4 mmol) and ethyl iodide (1.23 mL, 15.3 mmol) were added and the reaction mixture was stirred for 24 h at room temperature. The reaction mixture was concentrated, and the residue was dissolved in H₂O. The aqueous solution was extracted with ethyl acetate. The organic layer was dried over MgSO₄ and concentrated. The crude product was purified by column chromatography eluting with ethyl acetate/hexanes (1/1, v/v) to afford 3.77 g (75% yield) of the desired product as an oil.

(S)-N1-(mesyl)-N4-(benzyloxycarbonyl)-Piperazine Ethyl Ester 3.7. (S)-N1-(tert-butoxycarbonyl)-N4-(benzyloxycarbonyl)-Piperazine ethyl ester (3.77 g, 9.6 mmol) was dissolved in 4 N HCl/dioxane and stirred for 2 h at room temperature. The reaction mixture was concentrated under a stream of N2, then on the vacuum line. The residue was dissolved in methylene chloride and cooled to 0° C. Triethylamine (6.7 mL, 50 mmol) and DMAP (0.12 g, 1.0 mmol) were added, followed by methanesulfonyl chloride (1.5 mL, 19.2 mmol). The reaction solution was stirred for 24 h at room temperature. The reaction solution was then washed with brine, and the organic layer was dried over MgSO₄ and concentrated. The crude product was purified by column chromatography eluting with ethyl acetate/hexanes (1/1, v/v) to afford 2.1 g (59% yield) of the desired product as an oil.

2. Oligomer Synthesis

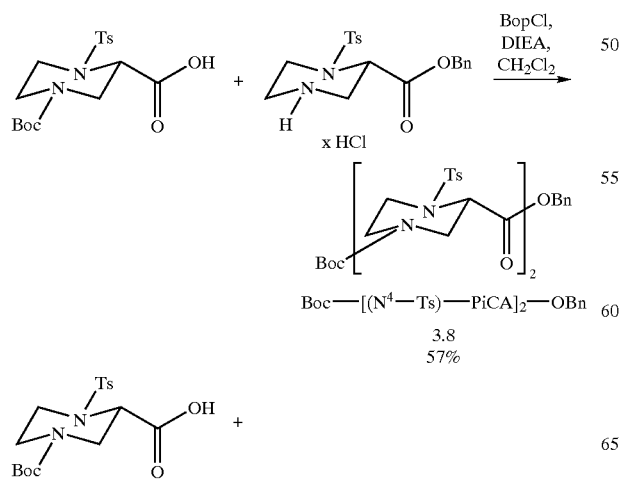

Boc-{(N4-Ts)-PiCA}₂-OBn 3.8. Via general procedure A, Boc-{(N4-Ts)-PiCA}-OBn (0.15 g, 0.3 mmol) was Boc-deprotected and coupled with Boc-{(N4-Ts)-PiCA}-OH (0.12 g, 0.3 mmol). After workup, the crude product was purified by column chromatography eluting with ethyl acetate/hexanes (1/1, v/v) to afford 0.13 g (57% yield) of the desired product as a colorless oil.

Boc-{(N4-Ts)-PiCA}₃-OBn 3.9. Via general procedure A, Boc-{(N4-Ts)-PiCA}₂-OBn (0.11 g, 0.2 mmol) was Boc-deprotected and coupled with Boc-{(N4-Ts)-PiCA}-OH (58.3 mg, 0.2 mmol). After workup, the crude product was purified by column chromatography eluting with ethyl acetate/hexanes (1/1, v/v) to afford 78 mg (51% yield) of the desired product as a white foam.

Boc-{(N4-Ts)-PiCA}₄-OBn 3.10. Via general procedure A, Boc-{(N4-Ts)-PiCA}₃-OBn (65.2 mg, 0.1 mmol) was Boc-deprotected and coupled with Boc-{(N4-Ts)-PiCA}-OH (24.9 mg, 0.1 mmol). After workup, the crude product was purified by column chromatography eluting with ethyl acetate/hexanes (1/1, v/v) to afford 25 mg (33% yield) of the desired product as a white foam.

Circular dichroism data for (N4-Ts)-PiCA oligomers in methanol (25° C.) suggest that the tetramer adopts a distinct secondary structure, which is different from the structure adopted by the dimer and trimer.

cis-5-Methoxymethyl-3-Pyrrolidine Carboxylic Acid (cis-5-MOM-PCA)

1. Synthesis of Protected Monomer

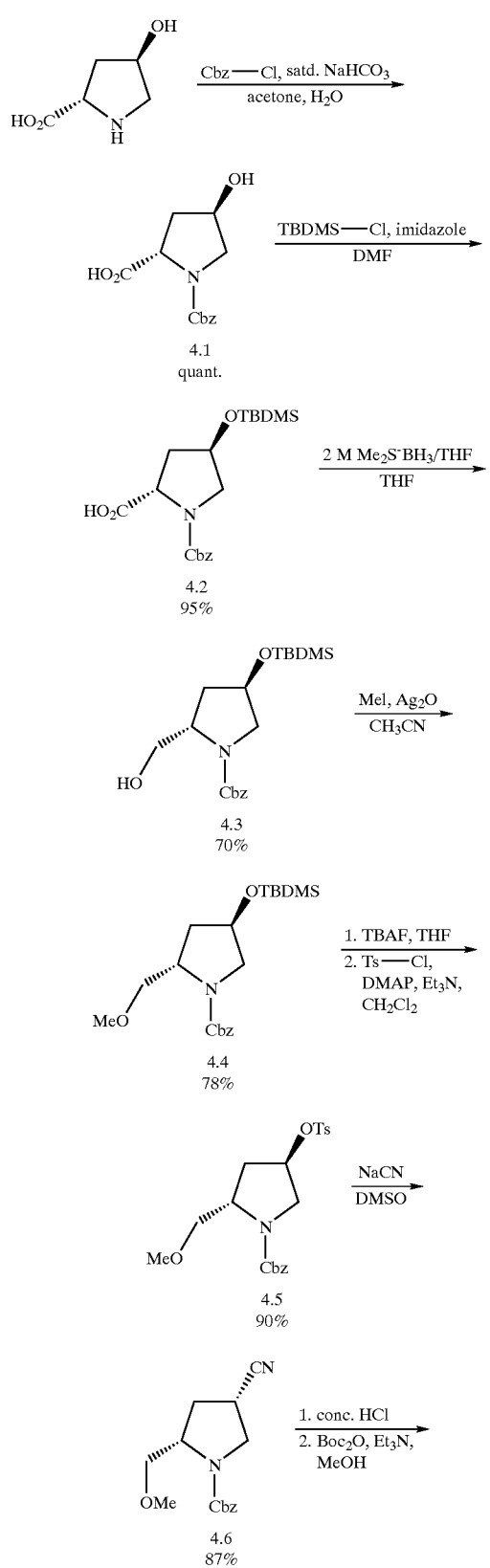

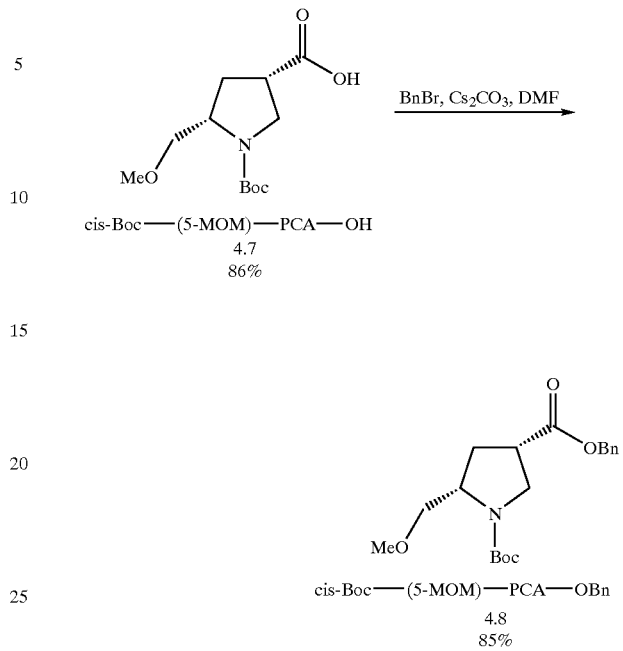

trans-4-Hydroxy-Cbz-L-Proline4.1. Benzyl chloroformate (8.6 mL, 0.06 mol) was dissolved in acetone (12 mL), and this solution was added dropwise to a stirred solution of trans-4-hydroxy-L-proline (6.56 g, 0.05 mol) in satd. NaHCO$_3$ (160 mL) and H$_2$O (24 mL). The resulting solution was stirred for 6 h at room temperature. The solution was washed with diethyl ether, and the organic layer was discarded. The aqueous layer was acidified with to pH 3 with 1 M HCl and extracted with ethyl acetate. The organic layer was dried over MgSO$_4$ and concentrated to afford 13.5 g (quantitative yield) of the desired product as an oil.

trans-4-TBDMSO-Cbz-L-Proline 4.2. trans-4-Hydroxy-Cbz-L-proline (13.5 g, 0.05 mol) was dissolved in DMF (190 mL), followed by the addition of imidazole (17.0 g, 0.25 mol) and TBDMS-Cl (22.6 g, 0.15 mol). The resulting solution was stirred for 12 h at room temperature. Methanol (150 mL) was added and the solution was stirred for 2 h. The solution was concentrated, the residue was dissolved in ethyl acetate and washed with 1 M HCl. The organic layer was dried over MgSO$_4$ and concentrated. The crude product was purified by column chromatography eluting with methylene chloride/ethyl acetate/acetic acid (2/1/0.03, v/v/v) to afford 18.01 g (95% yield) of the desired product as an oil.

trans-5-Hydroxylmethyl-3-TBDMSO-Cbz-Pyrrolidine 4.3. trans-4-TBDMSO-Cbz-L-proline (14.31 g, 0.04 mol) was dissolved in THF and added via cannula to a stirred solution of 2 M Me2S.BH3 in THF (48.0 mL, 0.09 mol). The resulting solution was stirred for 16 h at reflux. The reaction was then quenched with methanol (50 mL) and concentrated. The residue was dissolved in ethyl acetate and washed with brine. The organic layer was dried over MgSO$_4$ and concentrated. The crude product was purified by column chromatography eluting with hexanes/ethyl acetate (3/1, v/v) to afford 9.73 g (70% yield) of the desired product as an oil.

trans-5-Methoxymethyl-3-TBDMSO-Cbz-Pyrrolidine 4.4. trans-2-Hydroxylmethyl-4-TBDMSO-Cbz-pyrrolidine (5.02 g, 13.7 mmol) was dissolved in acetonitrile (13.7 mL), followed by the addition of iodomethane (8.55 mL, 0.14 mol) and Ag₂O (6.36 g, 27.5 mmol). The resulting reaction mixture was stirred for 12 h at reflux in the dark. The reaction mixture was then filtered through celite and the celite was washed with acetonitrile. The filtrate was concentrated. The crude product was purified by column chromatography eluting with hexanes/ethyl acetate (3/1, v/v) to afford 4.05 g (78% yield) of the desired product as an oil.

trans-5-Methoxymethyl-3-Tosyl-Cbz-Pyrrolidine 4.5. trans-2-Methoxymethyl-4-TBDMSO-Cbz-pyrrolidine (8.99 g, 23.6 mmol) was dissolved in TUF (237 mL), followed by the addition of 1 M TBAF in THF (23.7 mL, 23.7 mmol). The resulting solution was stirred for 3 h at room temperature. The reaction was quenched with satd. NH₄Cl. The solution was concentrated, the residue dissolved in ethyl acetate and washed with brine. The organic layer was dried over MgSO₄ and concentrated. The residue was dissolved in methylene chloride (230 mL) and cooled to 0° C. DMAP (3.37 g, 27.6 mmol) and triethylamine (7.7 mL, 66.2 mmol) were added, followed by p-toluenesulfonyl chloride (5.26 g, 27.6 mmol). The reaction solution was stirred for 12 h at room temperature. The solution was washed with brine and the organic layer was dried over MgSO₄ and concentrated. The crude product was purified by column chromatography eluting with hexanes/ethyl acetate (2/1, v/v) to afford 8.67 g (90% yield) of the desired product as an oil.

cis-5-Methoxymethyl-3-Cyano-Cbz-Pyrrolidine 4.6. trans-5-Methoxymethyl-3-tosyl-Cbz-pyrrolidine (3.55 g, 8.8 mmol) was dissolved in DMSO (8.8 mL). Finely ground NaCN(0.65 g, 13.2 mmol) was added, and the resulting reaction mixture was stirred 4 h at 80° C. The solution was cooled to room temperature, diluted with H₂O (9 mL) and brine (9 mL), and extracted with ethyl acetate. The organic extracts were dried over MgSO₄ and concentrated. The crude product was purified by column chromatography eluting with hexanes/ethyl acetate (2/1, v/v) to afford 2.09 g (87% yield) of the desired product as an oil.

cis-5-Methoxymethyl-Boc-3-Pyrrolidine Carboxylic Acid {cis-Boc-(5-MOM)-PCA-OH} 4.7. cis-5-Methoxymethyl-3-cyano-Cbz-pyrrolidine (1.71 g, 6.2 mmol) was dissolved in concentrated HCl and stirred for 12 h at 50° C. The solution was cooled to room temperature and neutralized with NaHCO₃. The solution was concentrated, and the residue was dissolved in methanol (62 mL). Triethylamine (2.6 mL, 18.7 mmol) and Boc₂O (1.63 g, 7.5 mmol) were added, and the solution was stirred 12 h at 50° C. The solution was concentrated and the residue was dissolved in H₂O. The aqueous solution was washed with diethyl ether, and the organic layer was discarded. The aqueous layer was acidified with to pH 3 with 1 M HCl, and extracted with ethyl acetate. The organic layer was dried over MgSO₄ and concentrated to afford 1.40 g (86% yield) of the desired product as an oil.

cis-5-Methoxymethyl-Boc-3-Pyrrolidine Benzyl Ester Acid {cis-Boc-(5-MOM)-PCA-OBn} 4.8. cis-5-Methoxymethyl-Boc-3-pyrrolidine carboxylic acid (1.4 g, 5.3 mmol) was dissolved in DMF,(26.5 mL). CS₂CO₃ (1.73 g, 5.3 mmol) and benzyl bromide (0.76 mL, 6.4 mmol) were added, and the reaction mixture was stirred 24 h at room temperature. The reaction mixture was concentrated, and the residue was dissolved in H₂O. The aqueous solution was extracted with ethyl acetate. The organic layer was dried over MgSO₄ and concentrated. The crude product was purified by column chromatography eluting with ethyl acetate/hexanes (1/1, v/v) to afford 1.88 g (85% yield) of the desired product as an oil.

2. Oligomer Synthesis

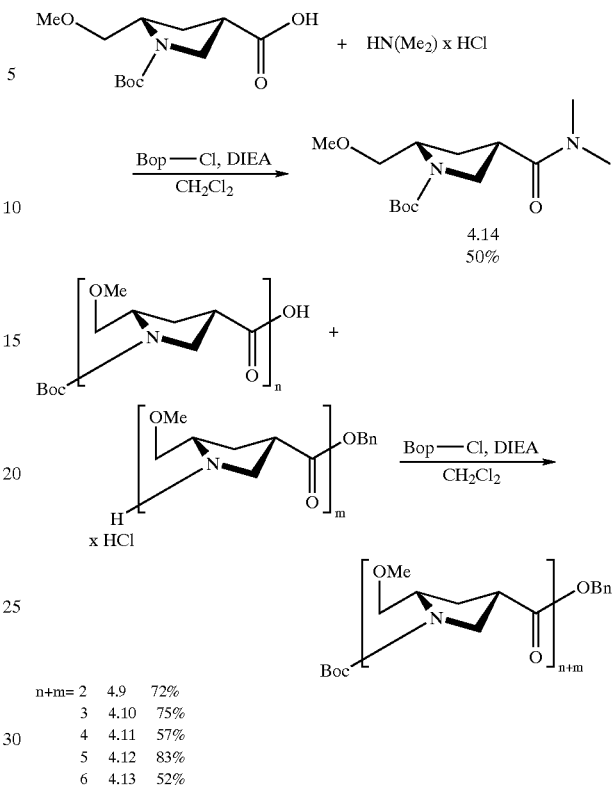

| n+m= | 2 | 4.9 | 72% |
| | 3 | 4.10 | 75% |
| | 4 | 4.11 | 57% |
| | 5 | 4.12 | 83% |
| | 6 | 4.13 | 52% |

Boc-{(cis-5-MOM)-PCA}₂-OBn 4.9. Via general procedure B, cis-Boc-(5-MOM)-PCA-OBn (1.88 g, 5.38 mmol) was Boc-deprotected and coupled with cis-Boc-(5-MOM)-PCA-OH (1.40 g, 5.38 mmol). After workup, the crude product was purified by column chromatography eluting with ethyl acetate/hexanes (3/1, v/v) to afford 1.90 g (72% yield) of the desired product as an oil.

Boc-{(cis-5-MOM)-PCA}₃-OBn 4.10. Via general procedure B, cis-Boc-{(5-MOM)-PCA}₂-OBn (0.26 g, 0.54 mmol) was Boc-deprotected and coupled with cis-Boc-(5-MOM)-PCA-OH (0.13 g, 0.54 mmol). After workup, the crude product was purified by column chromatography eluting with ethyl acetate/methanol (20/1, v/v) to afford 0.25 g (75% yield) of the desired product as a white foam.

Boc-{(cis-5-MOM)-PCA}₄-OBn 4.11. Via general procedure B, cis-Boc-{(5-MOM)-PCA}2-OBn (0.26 g, 0.54 mmol) was Boc-deprotected and coupled with cis-Boc-{(5-MOM)-PCA}2-OH (0.20 g, 0.54 mmol). After workup, the crude product was purified by column chromatography eluting with ethyl acetate/methanol (15/1, v/v) to afford 0.24 g (57% yield) of the desired product as a white foam.

Boc-{(cis-5-MOM)-PCA}₅-OBn 4.12. Via general procedure B, cis-Boc-{(5-MOM)-PCA}₃-OBn (0.12 g, 0.18 mmol) was Boc-deprotected and coupled with cis-Boc-{(5-MOM)-PCA}₂-OH (0.09 g, 0.20 mmol). After workup, the crude product was purified by column chromatography eluting with methylene chloride/methanol (10/1, v/v) to afford 0.12 g (83% yield) of the desired product as a white foam.

Boc-{(cis-5-MOM)-PCA}₆-OBn 4.13. Via general procedure B, cis-Boc-{(5-MOM)-PCA}₄-OBn (0.13 g, 0.17 mmol) was Boc-deprotected and coupled with cis-Boc-{(5-MOM)-PCA}₂-OH (0.07 g, 0.17 mmol). After workup, the crude product was purified by column chromatography eluting with methylene chloride/methanol (10/1, v/v) to afford 70 mg (52% yield) of the desired product as a glassy solid.

Boc-(cis-5-MOM)-PCA-NMe₂ 4.14. Via general procedure B, Boc-cis-(5-MOM)-PCA-OBn (0.11 g, 0.41 mmol) was Boc-deprotected and coupled with dimethylamine hydrochloride (0.04 g, 0.49 mmol). After workup, the crude product was purified by column chromatography eluting with ethyl acetate/hexanes (3/1, v/v) to afford 57 mg (50% yield) of the desired product as an oil.

Di-Substituted Carboxylic Acids
1. Synthesis of the Protected Monomer

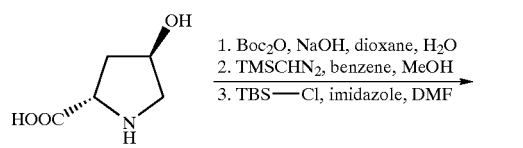

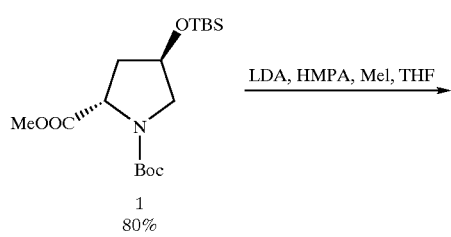

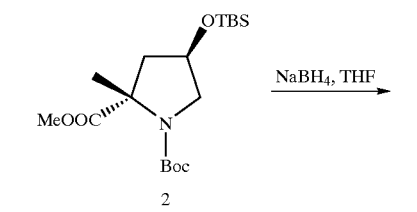

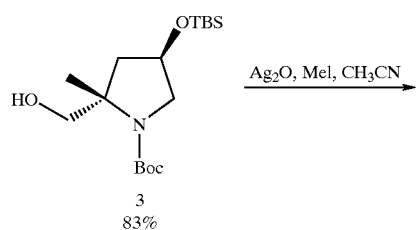

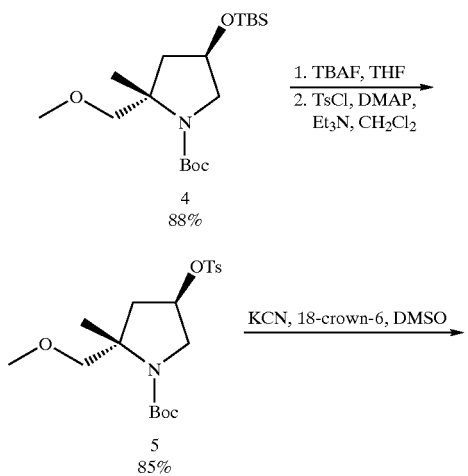

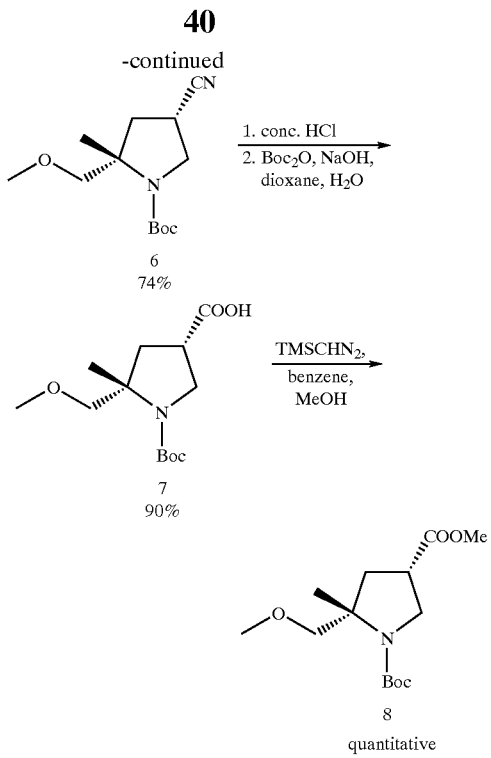

The following monomers have also been synthesized via a similar reaction scheme:

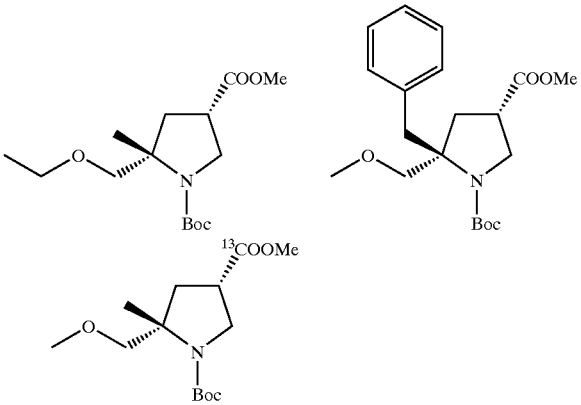

Compound 1. trans-4-Hydroxy-L-proline (13.11 g, 0.1 mol) was dissolved in 1M NaOH (120 mL) and cooled to 0° C. Boc₂O (24.0 g, 0.11 mol) dissolved in dioxane (120 mL) was added and the solution was stirred for 4 h at room temperature. Dioxane was removed via rotary evaporation and the resulting aqueous solution was washed with ether. The aqueous solution was then brought to pH 2 with 1 M HCl and extracted with ethyl acetate. The organic extracts were dried over MgSO₄ and concentrated to afford 21.3 g (92% yield) of the desired product as a white foam.

Boc-trans-4-hydroxy-L-proline (9.27 g, 0.04 mol) was dissolved in a 1M benzene/methanol (5/1, v/v) solution. 2M TMSCHN₂/hexanes was added dropwise and the resulting solution was stirred at room temperature for 1 h. The reaction solution was concentrated via rotary evaporation. The crude product was carried on to the next synthetic step without further purification.

Boc-trans-4-hydroxy-L-proline methyl ester (10.35 g, 0.04 mol) was dissolved in DMF (135 mL). Imidazole (13.6 g, 0.20 mol) was added, followed by the addition of tert-butyldimethylsilyl chloride (18.1 g, 0.12 mol) and the solution was stirred overnight at room temperature. DMF was removed via vacuum rotary evaporation and the residue was dissolved in ethyl acetate. The solution was washed with 1M HCl and brine. The organic solution was dried over $MgSO_4$ and concentrated. The crude product was purified by column chromatography eluting with hexanes/ethyl acetate (4/1, v/v) to afford 12.83 g (89% yield) of the desired product 1 as a colorless oil.

Compound 2. Diisopropyl amine (16.2 mL, 0.12 mol) was dissolved in THF (215 mL) and cooled to 0° C. 2. SM n-Butyllithium/hexanes was added and the solution was stirred for 30 minutes at 0° C. The solution was then cooled to 20° C. and HMPA (60 mL, 0.34 mol) was added. After 10 minutes, a solution of 1 (27.4 g, 0.076 mol) in THF (215 mL) was added dropwise. After addition the reaction solution was stirred from 20° C. to 0° C. The solution was then cooled to 78° C. and methyl iodide (23.7 mL, 0.38 mol) was added. The reaction solution was stirred for 2 h at 78° C. and then quenched with saturated $NH_4Cl$. The resulting solution was extracted with ethyl acetate. The organic extracts were dried over $MgSO_4$ and concentrated. The crude product was purified by column chromatography eluting with hexanes/ethyl acetate (6/1, v/v) to afford 21.09 g (74% yield) of the desired product 2 as a colorless oil. See Ohtake et al. (1999), Bull. Chem. Soc. Japan 72:2737.

Compounds 3. $NaBH_4$ (6.14 g, 0.16 mol) was added to a stirred solution of 2 (24.26 g, 0.065 mol) in THF (150 mL). The resulting solution was stirred at reflux for 4 h. MeOH (50 mL) was added over 1 h, and the solution was then diluted with $H_2O$. The organic solvents were removed via rotary evaporation and the resulting aqueous solution was extracted with ethyl acetate. The organic extracts were dried over $MgSO_4$ and concentrated. The crude product was purified by column chromatography eluting with hexanes/ethyl acetate (3/1, v/v) to afford 17.76 g (83% yield) of the desired product 3 as a colorless oil.

Compound 4. 3 (15.19 g, 0.046 mol) was dissolved in $CH_3CN$. Methyl iodide (28.7 mL, 0.46 mol) was added, followed by the addition of $Ag_2O$ (25 g, 0.092 mol). The reaction mixture was stirred overnight at 55° C., and then filtered through celite. The resulting filtrate was concentrated and purified by column chromatography eluting with hexanes/ethyl acetate (4/1, v/v) to afford 13.88 g (88% yield) of the desired product 4 as a colorless oil.

Compound 5. 1M TBAF/THF (42 mL, 0.042 mol) was added dropwise to a solution of 4 (13.88 g, 0.04 mol) in THF (200 mL). The solution was stirred for 3 h at room temperature and the quenched with saturated $NH_4Cl$. The organic solvent was removed via rotary evaporation, and the resulting aqueous solution was extracted with ethyl acetate. The organic extracts were dried over $MgSO_4$ and concentrated. The crude product was carried on to the next synthetic step without further purification.

The crude product was dissolved in $CH_2Cl_2$ (200 mL) and cooled to 0° C. DMAP (5.9 g, 0.049 mol) and triethylamine (13.5 mL, 0.099 mol) were added, followed by p-toluenesulfonyl chloride (8.8 g, 0.049 mol), and the resulting solution was stirred overnight at room temperature. The solution was washed with 1M HCl, and brine. The organic solution was dried over $MgSO_4$ and concentrated. The crude product was purified by column chromatography eluting with hexanes/ethyl acetate (4/1, v/v) to afford 13.76 g (85% yield) of the desired product 5 as a colorless oil.

Compound 6. 5 (13.76 g, 0.034 mol) was dissolved in DMSO (17 mL). 18-Crown-6 (5 eq) and finely ground KCN (5 eq) were added and the reaction mixture was stirred for 6 h at 80° C. The reaction solution was diluted with $H_2O$ (17 mL) and then extracted with ethyl acetate. The organic solution was dried over $MgSO_4$ and concentrated. The crude product was purified by column chromatography eluting with hexanes/ethyl acetate (4/1, v/v) to afford 13.76 g (69% yield) of the desired product 6 as a colorless oil.

Compound 7. 6 (4.34 g, 0.017 mol) was dissolved in concentrated HCl (68 mL) and stirred 6 h at 50° C. The solution was diluted with $H_2O$, neutralized with $NaHCO_3$, and concentrated. The crude product was carried on to the next synthetic step without further purification.

Triethylamine (9.5 mL, 0.068 mol) and $Boc_2O$ (7.5 g, 0.034 mol) were added to a stirred solution of the resulting crude product in MeOH (170 mL). The reaction mixture was stirred overnight at reflux. The reaction mixture was diluted with $H_2O$, the MeOH was removed via rotary evaporation, and the resulting aqueous solution was washed with ether. The aqueous solution was then brought to pH 2 with 1 M HCl and extracted with ethyl acetate. The organic extracts were dried over $MgSO_4$ and concentrated to afford 3.55 g (76% yield) of 7 as the desired product as a white foam.

Compound 8. 7 (2.3 g, 8.4 mmol) was dissolved in a 1M benzene/methanol (5/1, v/v) solution. 2M $TMSCHN_2$/hexanes (4.4 mL, 8.8 mmol) was added dropwise and the resulting solution was stirred at room temperature for 1 h. The reaction solution was concentrated by rotary evaporation. The crude product was purified by column chromatography eluting with hexanes/ethyl acetate (1/1, v/v) to afford 2.4 g (quantitative yield) of the desired product 8 as a colorless oil.

2. Oligomer Synthesis

A. Synthesis of free amine

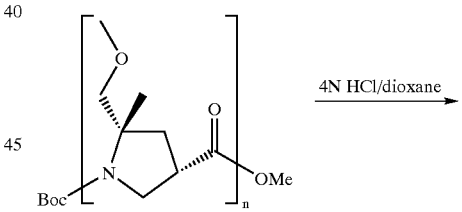

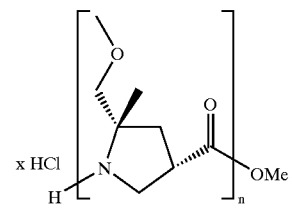

B. Synthesis of Boc protected amine

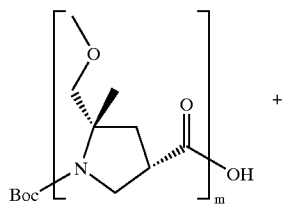

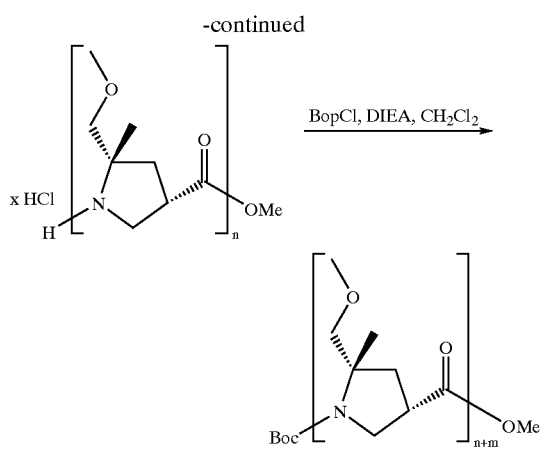

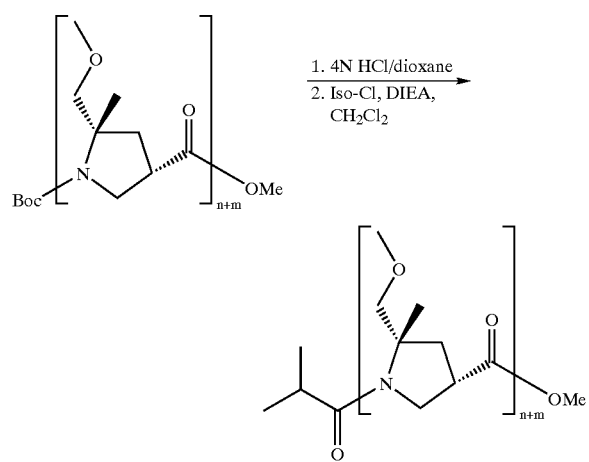

C. Synthesis of isobutyl amide

A. General procedure for synthesis of free amine. Boc-(disub PCA)$_n$-OMe was dissolved in 4N HCl/dioxane (2.5 eq.) The solution was stirred for 2 h, the solvent was removed under a stream of N$_2$, and the residue was dried under vacuum to give the desired product, HCl.H-(disub PCA)$_n$-OMe, as a white solid.

B. General procedure for synthesis of Boc protected amine. Boc-(disub PCA)$_m$-OH and HCl.H-(disub PCA)$_n$-OMe were dissolved in CH$_2$Cl$_2$ (0.1 M) and cooled to 0° C. BopCl (2.0 eq.) was added, followed by DIEA (5 eq.) The reaction mixture was stirred for 48 h at room temperature. The solution was washed with 1M HCl, saturated NaHCO$_3$, and brine. The organic solution was dried over MgSO$_4$ and concentrated. The crude product was purified by column chromatography to give the desired product, Boc-(disub PCA)$_{n+m}$-OMe.

C. General procedure for synthesis of isobutyl amide. Boc-(disub PCA)$_{n+m}$-OMe was dissolved in 4N HCl/dioxane (2.5 eq.) The solution was stirred for 2 h, the solvent was removed under a stream of N$_2$, and the residue was dried under vacuum to give the desired product, HCl.H-(disub PCA)$_{n+m}$-OMe, as a white solid. This residue was dissolved in CH$_2$Cl$_2$ and cooled to 0° C. Iso-Cl (2 eq.) was added, followed by DIEA (5 eq.) The reaction solution was stirred for 24 h at room temperature. The solution was washed with 1M HCl, saturated NaHCO$_3$, and brine. The organic solution was dried over MgSO$_4$ and concentrated. The crude product was purified by column chromatography to give the desired product, Iso-(disub PCA)$_{n+m}$-OMe.

β-Peptide Conjugates:

β-Peptide 101 is constructed from β-substituted β-amino acid residues ("β$^3$-residues"), which were made in enantiomerically pure form from the corresponding α-amino acid residues using a methodology developed by Seebach et al.[15] β-Peptides like 101 can be conveniently prepared with conventional automated solid-phase peptide synthesis equipment.

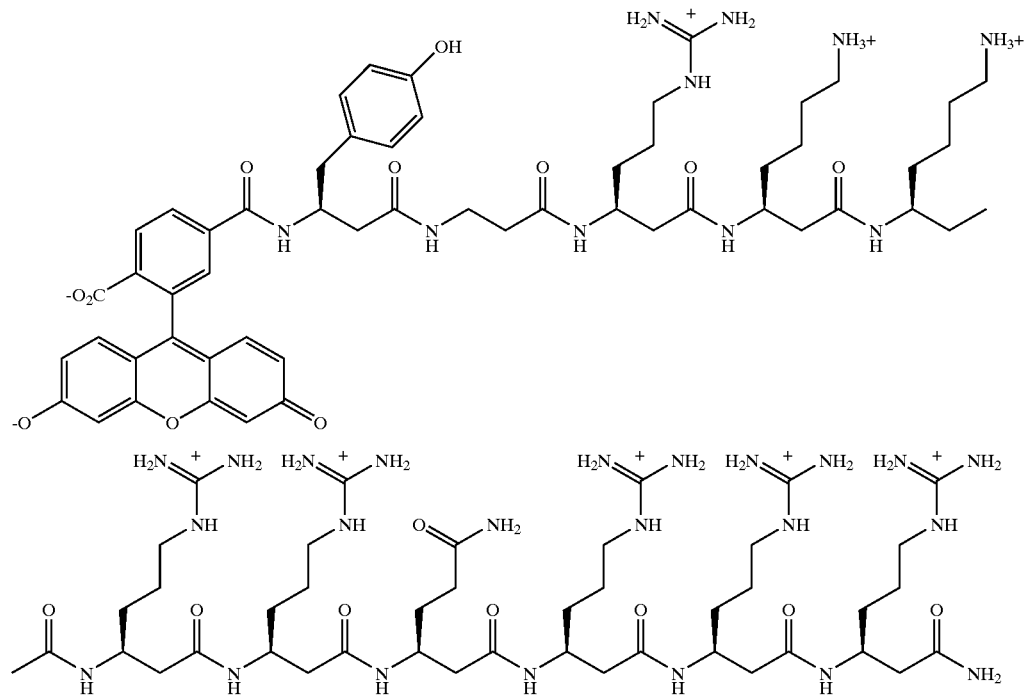

101 βTat(47–57)

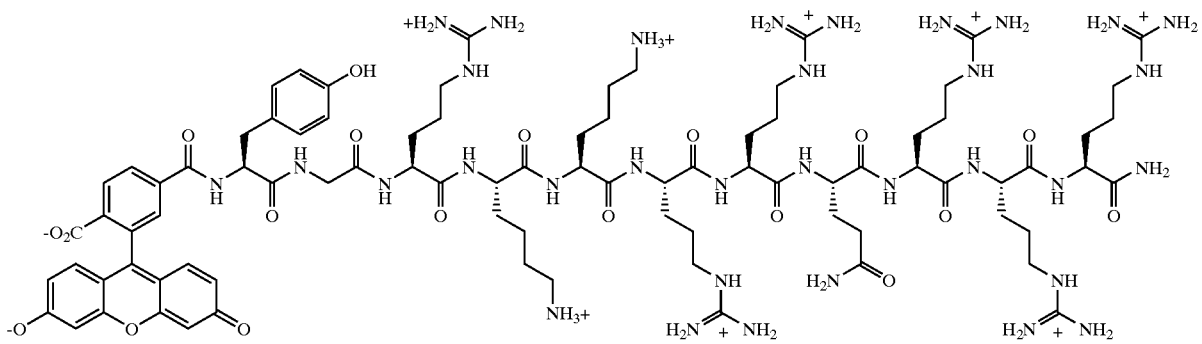

102-Tat(47-57)

Both the Tat fragment 102 and β-peptide analog 101 bear N-terminal fluorescein labels, to allow detection of cell membrane transit via fluorescence microscopy. HeLa cells were used to measure cell membrane transit. HeLa cells were obtained from the American Type Culture Collection (10801 University Boulevard, Manassas, Va. 20110-2209). HeLa cells were cultured in Dulbecco's modified Eagle's medium (DMEM) supplemented with 10% (v/v) fetal bovine serum (FBS), penicillin (100 units/mL), and streptomycin (100 μg/mL) at 37° C. in a humidified incubator containing 5% $CO_2$. All studies were performed using asynchronous log-phase cultures. Exponentially growing HeLa cells were dissociated with Trypsin, plated 40% confluent on six-well Lab-Tek coverslips (Nunc Inc., Naperville, Ill.) and cultured overnight. The culture medium was discarded, and the cells were washed once with DMEM. The peptides and fluorescein stock solutions were diluted in DMEM, and the cell monolayers were incubated at 37° C. with peptide solutions at the appropriate concentrations for 10 min. Subsequently, cells were rinsed three times with DMEM at room temperature and fixed in paraformaldehyde (4% w/v in PBS) for 5 min at room temperature. For experiments at 4° C., the protocol was the same except that all incubations were performed at 4° C. until the end of the fixation procedure. Fixed cell monolayers were permeabilized with "Triton X-100"-brand detergent (0.1% w/v) for 10 min and washed twice with PBS (pH 7.3). Cells were stained with propidium iodide (1 μg/mL in PBS) for 5 min at room temperature. Cells were then washed three times with PBS and mounted onto glass microscope slides using mounting medium for fluorescence. The distribution of the fluorescence was analyzed on a Zeiss Axiovert 100TV confocal microscope equipped with a Kr/Ar laser and 63× oil immersion objective lens (Leica). Images were captured with BioRad Laser Sharp MRC1024 and Adobe Photoshop version 4.0.1 software.

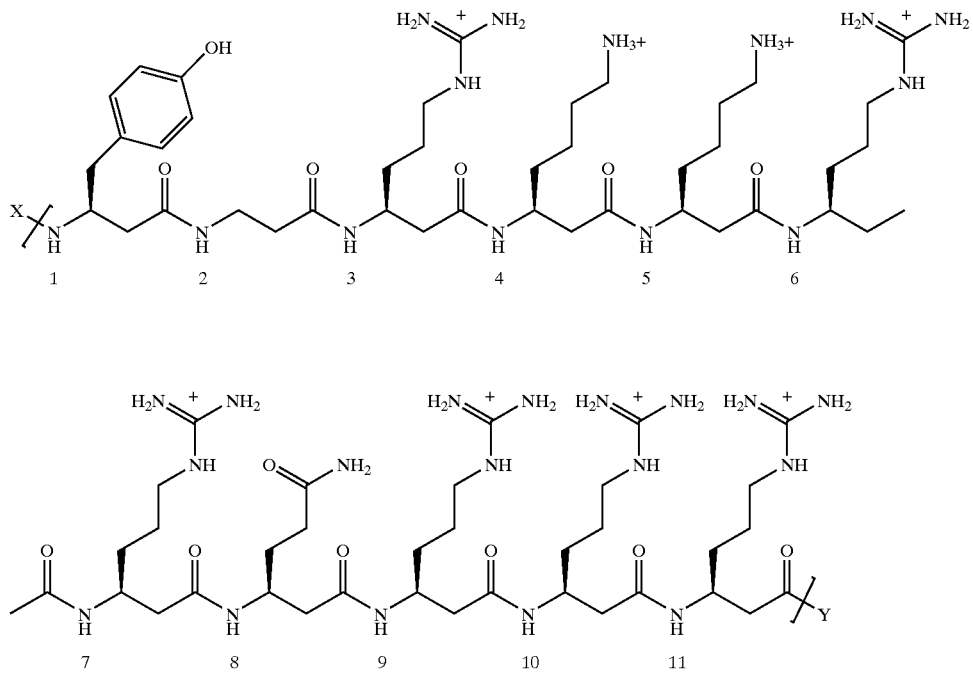

β-Peptide 101' is the same fragment as shown in 101, with the exception that the N-terminal fluorescein group is no longer present, nor is the C-terminal amino group. In 101', X is hydrogen, an amino-capping group, an amino-protecting group, or a molecule or compound of interest; Y is hydrogen, a carboxy-capping group, a carboxy-protecting group, or a molecule or compound of interest. As used herein, the term "protecting group" denotes generically any chemical moiety capable of selective addition to and removal from a reactive site to allow manipulation of a chemical entity at sites other than the protected site(s). The term "capping group" denotes generically any chemical moiety capable of selective addition to a reactive site, but not necessarily selectively removable from the site once bound (e.g., acetyl, formyl, or anisyl when used as an N-terminal capping group). A host of capping and/or protecting groups are known in the art. An illustrative, non-limiting list of protecting groups includes methyl, formyl, ethyl, acetyl, t-butyl, anisyl, benzyl, trifluoroacetyl, N-hydroxysuccinimide, t-butoxycarbonyl, benzoyl, 4-methylbenzyl, thioanisyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl, 2-chlorobenzyloxycarbonyl, 2,4,5-trichlorophenyl, 2-bromobenzyloxycarbonyl, 9-fluorenylmethyloxycarbonyl, triphenylmethyl, and 2,2,5,7,8-pentamethyl-chroman-6-sulphonyl. The substituents X and Y, may be the same or different, and may or may not be orthogonally removable.

In the present invention, compound 101' and related analogs, homologs, and peptides containing compound 101' as a portion of a larger polypetide (containing either α-amino acids, β-amino acids, or a combination thereof) are to be used as the "vehicle" portion of a conjugate to translocate a molecule across the membrane of a living cell. Thus, in the preferred embodiment of the present invention, a molecule of interest (i.e., a molecule that is to be translocated across the cell membrane) is conjugated to a vehicle comprising 101' and derivative thereof. The resulting conjugate is then contacted with the living cell. The presence of the vehicle causes the entire conjugate to pass through the cell membrane and into the interior of the target cell.

As used herein, the term "contacted," explicitly encompasses bringing the β-peptide or β-peptide conjugate into physical contact with the living cell by any means, without limitation, including (by way of illustration only), direct contact in vitro or in vivo, or bringing the β-peptide or β-peptide conjugate into physical contact with the living cell via any route of administration to a higher living organism (including mammals), including orally, topically, nasally, via inhalation, parenterally, intravenously, intra-arterially, intramuscularly, and rectally.

The nature of the molecule or compound attached to the β-peptide vehicle is not critical to the invention, so long as the entire conjugate will translocate across a living cell membrane. It is very much preferred that the molecule be conjugated to the vehicle at the vehicle's N-terminus. The molecule may be attached at an interior position. The molecule may also be attached at the C-terminus of the vehicle, but this point of attachment is not preferred. The molecule conjugated to the β-peptide vehicle need not have pharmacological activity. For example, the molecule conjugated to the β-peptide vehicle can be a dye, a fluorophore, a chromophore, a radio-label, a contrast agent, etc. As shown in the following paragraphs, such conjugates are useful for visualizing the interior of cells after exposure to the conjugates.

FIGS. 1A through 1E show representative fluorescence results with HeLa cells for 101 and 102. Neither molecule moves significantly into the cells when introduced at a concentration of 10 nM or 50 nM (FIGS. 1A and 1B), but at 100 nM, 500 nM, and 1000 nM, both compounds 101 and 102 can be detected inside the cells (FIGS. 1C, 1D and 1E).

Figure 2:
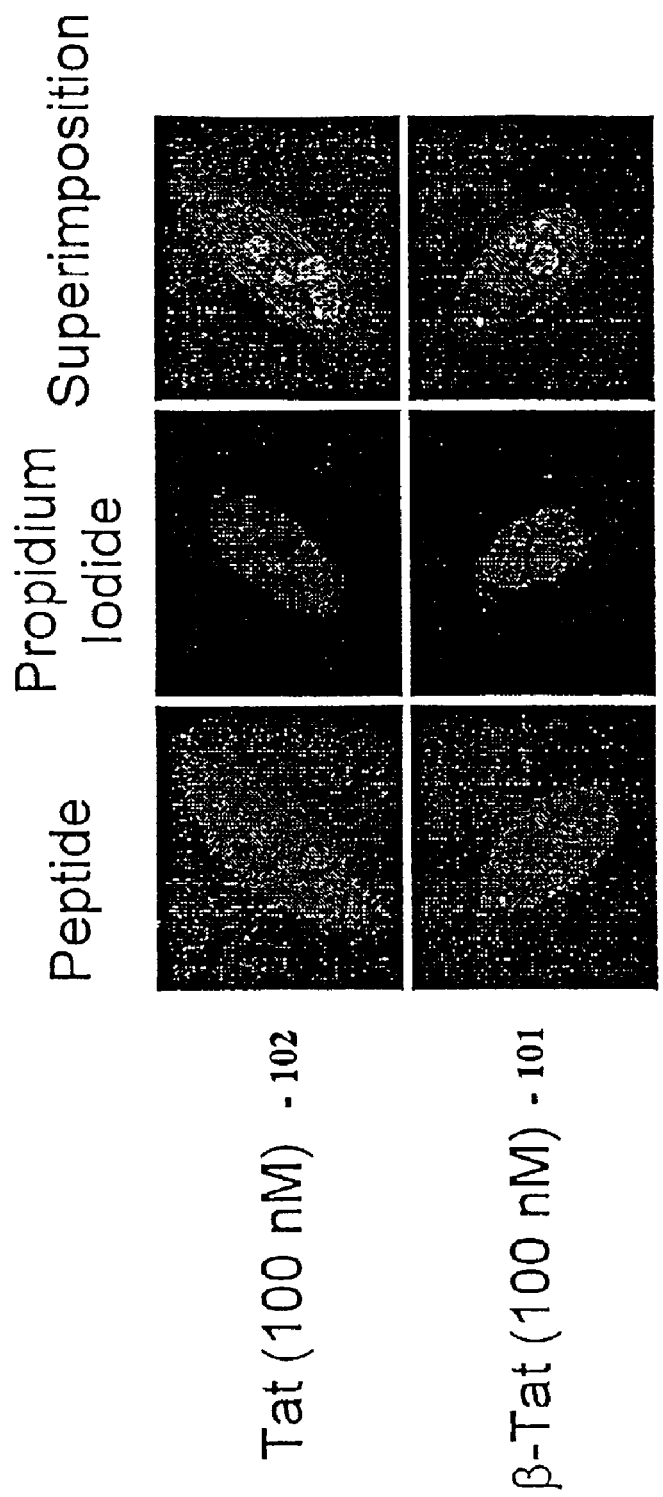
FIG. 2 is a collection of fluorescence counter-stained micrographs showing nuclear localization of the β-peptides 101 and 102. HeLa cells were incubated at 37° C. with peptide solutions in DMEM at 100 nM for 10 min, then washed with PBS and fixed in paraformaldehyde (4% w/v in PBS). Fixed cell monolayers were permeabilized with Triton X-100 (0.1% w/v) and washed with PBS. Cells were then stained with propidium iodide (1 μg/ml in PBS) and washed.

To identify the major intracellular destination of these molecules, the cells were co-stained with propidium iodide, which is selective for nucleic acids. The co-staining results with Tat fragment 102 (see FIG. 2) match previous reports that related peptides localize in the nucleus; the results for β-peptide 101 show that this unnatural analog behaves similarly to its a-peptide counterpart.

Control experiments were also conducted to determine whether all 11 β-amino acid residues were necessary for translocation by 101 and 102. Working from Tat 48–60, Vivès et al. showed that Arg-55, Arg-56 and Arg-57 were critical for translocation (in contrast, the presence or absence of Pro-58, Pro-59 and/or Gln-60 had little effect on translocation).[2b]

Figures 3A, 3B:
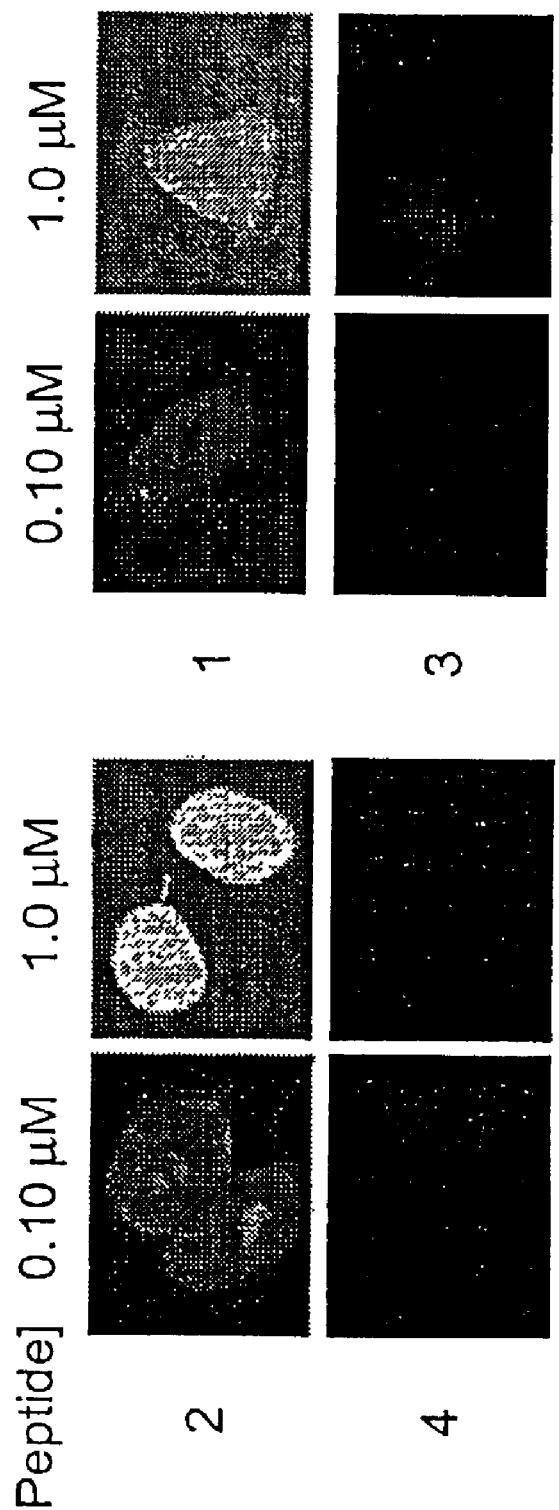
FIGS. 3A and 3B show representative fluorescence results for β-Tat 47–57 (101) with a control by β-Tat 47–54 (103) (FIG. 3B) and Tat 47–57 (102) with a control by Tat 47–54 (104) (FIG. 3A) indicating that the control compounds lacking the last three residues fail to enter HeLa cells.

Therefore, the truncated β-peptide 103, which lacks the three C-terminal β³-homoarginine residues of 101, was examined for translocation, as was the corresponding α-peptide analog 104 (See FIG. 3). No cell penetration could be detected after treatment with up to 1 μM 103 or 104, a ten-fold higher concentration than is required for detectable cell penetration by full length β-peptide 101 and its α-analog 102. In addition, fluorescein itself did not enter the cells under these conditions. These results show that a minimum β-peptide length and/or charge is required for movement across cell membranes.

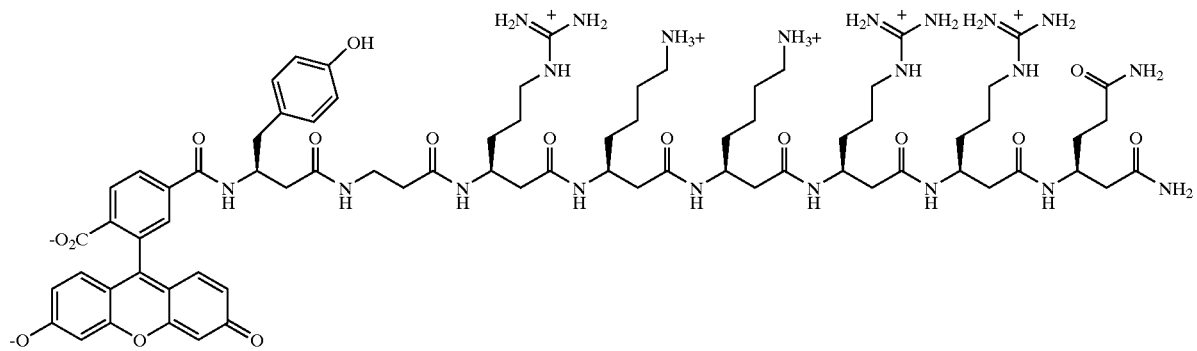

103

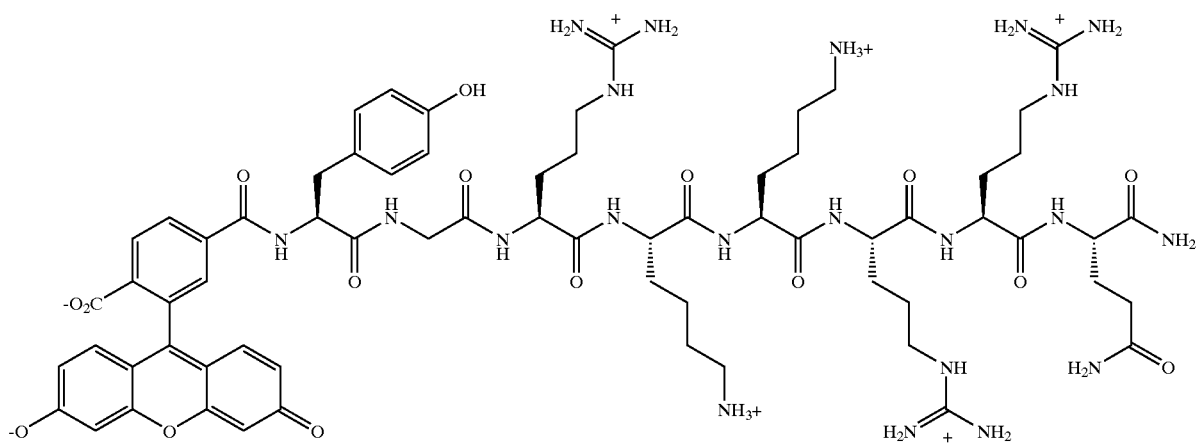

Figure 4:
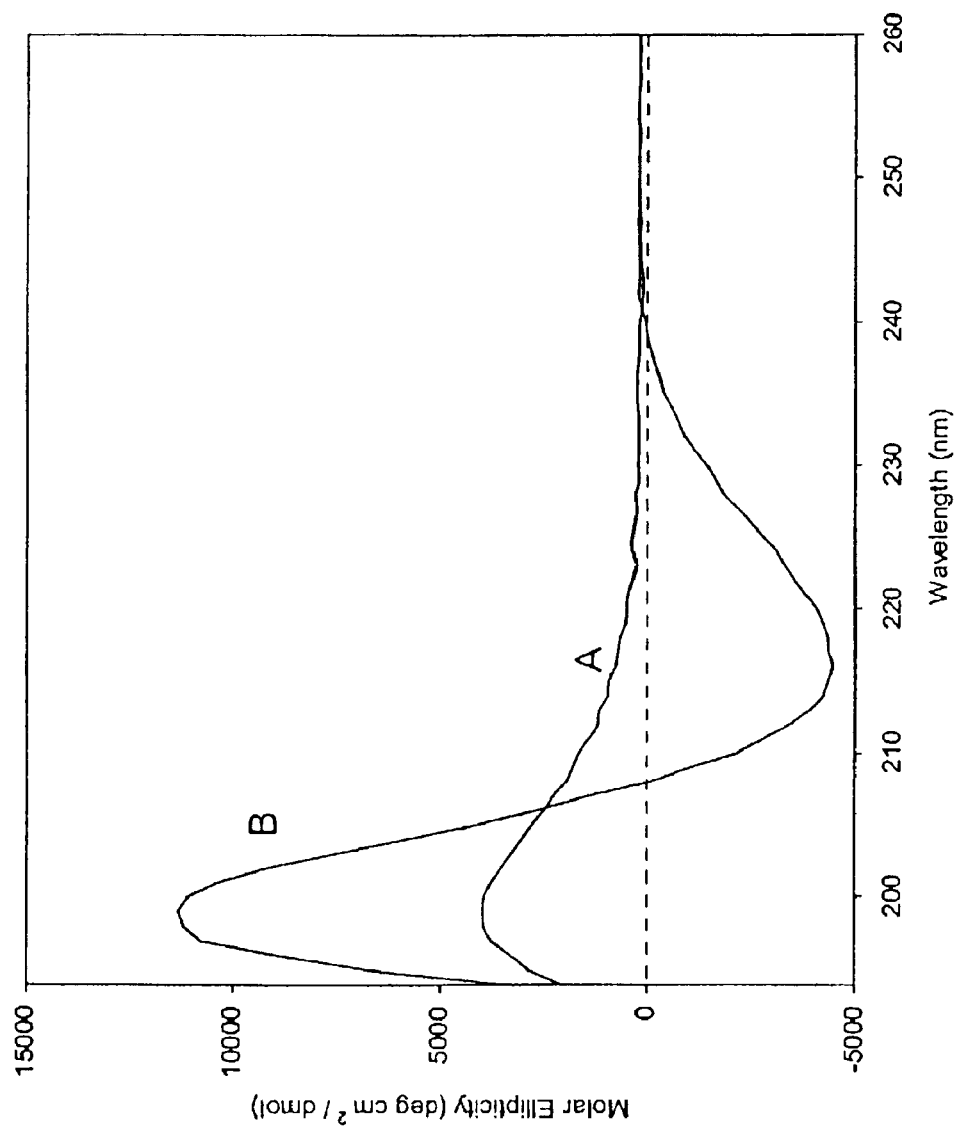
FIG. 4 depicts superimposed circular dichroism spectra of β-peptide 101' in water (trace A) and methanol (trace B).

To investigate the ability of the disclosed compounds to form helical structures, circular dichroism spectra were obtained for β-peptide 101' (see FIG. 4). These results indicate that β-peptide 101' displays the characteristic 14-helical CD signature, with a minimum at 216 and a maximum at 199 nm. Thus, β-peptide 101' has an intrinsically higher propensity than does α-peptide 102 to adopt an ordered conformation in non-aqueous environments.

The mechanism by which short Tat-derived peptides and related peptides traverse cell membranes remains unclear. Several groups have concluded that endocytosis does not play a role in this process because the transit rate is not temperature-dependent.[2a] The inventors found no difference in translocation activity for either 101 or 102 between 37° C. and 4° C. These findings are consistent with prior reports with regard to α-peptide 102 and suggest that cell penetration by β-peptide 101 does not depend upon endocytosis.

Other β-peptide conjugate fabricated according to the above protocols have also be found to translocate across cell membranes, including β-peptides wherein the backbone of the molecule is rigidified by cyclically-constrained β-amino acid residues. These are residues wherein the α and β carbons of the backbone are incorporated into a ring structure. Thus, the following compounds have also been synthesized and shown to translocate across the cell membrane of living HeLa cells:

Based on these results, it is also expected that the following compounds will likewise translocate across the cell membranes of living cells:

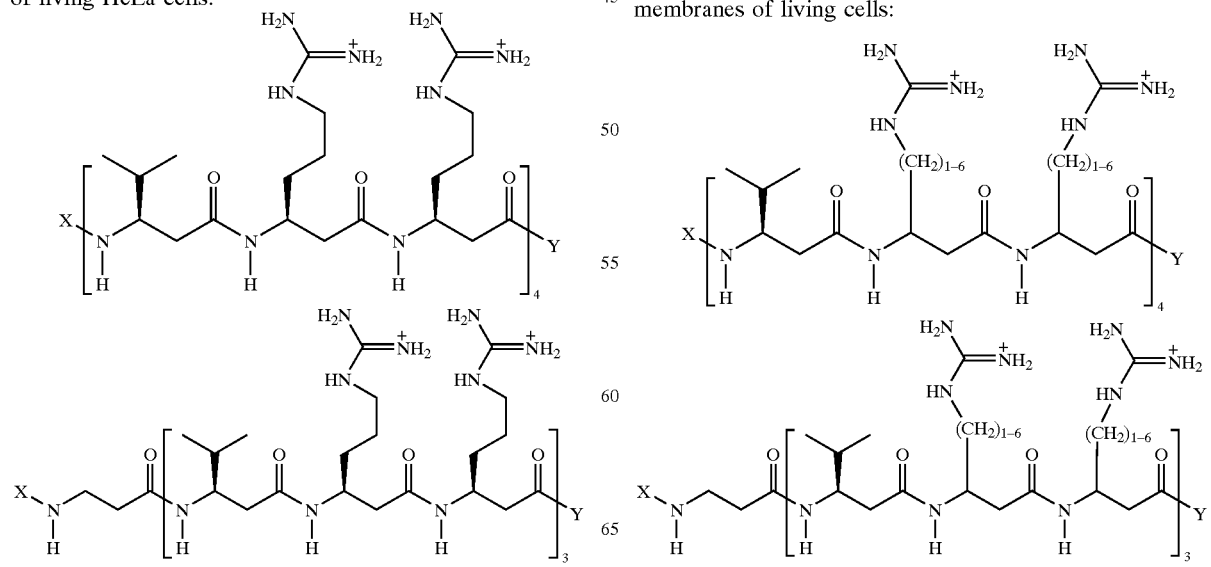

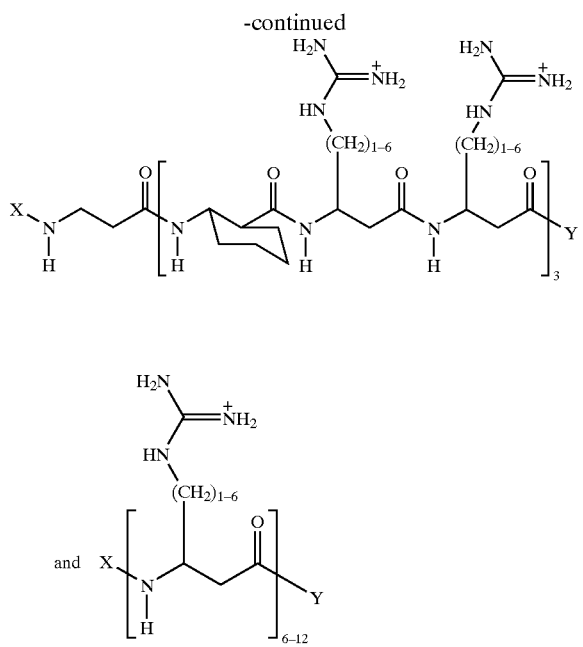

The invention is not restricted to those embodiments illustrated above, but encompasses all modifications and variations thereof as fall within the scope of the attached claims.

REFERENCES

1. Prochiantz, A. *Curr. Opin. Cell Biol.* 2000, 12, 400. Schwarze, S. R.; Hruska, K. A.; Dowdy, S. F. *Trends Cell Biol.* 2000, 10, 290. Lingren, M.; Hällbrink, M.; Prochiantz, A.; Langel, Ü. *Trends Pharmacol. Sci.* 2000, 21, 99.
2. (a) Vivàs, E.; Brodin, P.; Lebleu, B. *J. Biol. Chem.* 1997, 272, 16010. (b) Vivàs, E.; Granier, C.; Prevot, P.; Lebleu, B. *Lett. Pept. Sci.* 1997, 4, 429.
3. Derossi, D.; Joliot, A. H.; Chassaing, G.; Prochiantz, A. *J. Biol. Chem.* 1994, 269, 10444. Derossi, D.; Calvet, S.; Trembleau, A.; Brunissen, A.; Chassaing, G.; Prochiantz, A. *J. Biol. Chem.* 1996, 271, 18188.
4. (a) Zhang, L.; Torgerson, T. R.; Liu, X.-Y.; Timmons, S.; Colosia, A. D.; Hawiger, J.; Tam, J. P. *Proc. Natl. Acad. Sci. USA* 1998, 95, 9184. (b) Hawiger, J. *Curr. Opin. Chem. Biol.* 1999, 3, 89.
5. Mitchell, D. J.; Kim, D. T.; Steinman, L.; Fathman, C. G.; Rothbard, J. B. *J. Pept. Res.* 2000, 56, 318. Futaki, S.; Suzuki, T.; Ohashi, W.; Yagami, T.; Tanaka, S.; Ueda, K.; Sugiura, Y. *J. Biol. Chem.* 2001, 276, 5836.
6. Wender, P. A.; Mitchell, D. J.; Pattabiraman, K.; Pelkey, E. T.; Steinman, L.; Rothbard, J. B. *Proc. Natl. Acad. Sci. USA* 2000, 97, 13003.
7. Fawell, S.; Seery, J.; Kaikh, Y.; Moore, C.; Chen, L. L.; Pepinsky, B.; Barsoum, J. *Proc. Natl. Acad. Sci. USA* 1994, 91, 664. Schwarze, S. R.; Ho, A.; Vocero-Akbani, A.; Dowdy, S. F. *Science* 1999, 285, 1569.
8. Pooga, M.; Soomets, U.; Hällbrink, M.; Valkna, A.; Saar, K.; Rezaei, K.; Kahl, U.; Hao, J.-X.; Xu, X.-J.; Wiesenfeld-Hallin, Z.; Hökfelt, T.; Bartfai, T.; Langel, Ü. *Nat. Biotechnol.* 1998, 16, 857.
9. Rousselle, C.; Clair, P.; Lefauconnier, J.-M.; Kaczorek, M.; Scherrmann, J.-M.; Temsamani, J. *Mol. Pharmacol.* 2000, 57, 679. Rothbard, J. B.; Garlington, S.; Lin, Q.; Kirschberg, T.; Kreider, E.; McGrane, P. L.; Wender, P. A.; Khavari, P. A. *Nat. Medicine* 2000, 6, 1253.
10. Green, M.; Loewenstein, P. M. *Cell* 1988, 55, 1179. Frankel, A. D.; Pabo, C. O., *Cell* 1988, 22, 1189.
11. Rana et al. have shown that HIV Tat 47–57 and oligocarbamate and oligourea analogues bind tightly and specifically to TAR RNA: Wang, X.; Huq, I.; Rana, T. M. *J. Am. Chem. Soc.* 1997, 119, 6444; Tamilarasu, N.; Huq, I.; Rana, T. M. *J. Am. Chem. Soc.* 1999, 121, 1597.
12. Seebach, D.; Matthews, J. L. *J. Chem. Soc., Chem. Commun.* 1997, 2015. Gellman, S. H. *Acc. Chem. Res.* 1998, 31, 173. DeGrado, W. F.; Schneider, J. P.; Hamuro, Y. *J. Pept. Res.* 1999, 54, 206. Kirshenbaum, K.; Zuckermann, R. N.; Dill, K. A. *Curr. Opin. Struct. Biol.* 1999, 9, 530. Stigers, K. D.; Soth, M. J.; Nowick, J. S. *Curr. Opin. Chem. Biol.* 1999, 3, 714. Barron, A. E.; Zuckermann, R. N. *Curr. Opin. Chem. Biol.* 1999, 3, 681. Gademann, K.; Hintermann, T.; Schreiber, J. V. *Curr. Med. Chem.* 1999, 6, 905.
13. Werder, M.; Hausre, H.; Abele, S.; Seebach, D. *Helv. Chim. Acta* 1999, 82, 1774. Hamuro, Y.; Schneider, J. P.; DeGrado, W. F. *J. Am. Chem. Soc.* 1999, 121, 12200. Porter, E. A.; Wang, X.; Lee, H.-S.; Weisblum, B.; Gellman, S. H. *Nature* 2000, 404, 565.
14. Seebach, D.; Abele, S.; Schreiber, J. V.; Martinoni, B.; Nussbaum, A. K.; Schild, H.; Schulz, H.; Hennecke, H.; Woessner, R.; Bitsch, F. *Chimia* 1998, 52, 734.
15. Guichard, G.; Abele, S.; Seebach, D. *Helv. Chim. Acta* 1998, 81, 187, and references therein.

What is claimed is:

1. A method of translocating a molecule across a membrane of a living cell, the method comprising:

conjugating the molecule to an oligopeptide, the oligopeptide comprising at least 6 β-amino acid residues, at least 6 of which residues are substituted at their β-position carbon with a substituent selected from the group consisting of —$C_1$–$C_6$—NH—C(=$NH_2^+$)—$NH_2$, to thereby yield a conjugate; and then contacting the conjugate with the living cell.

2. The method of claim 1, wherein the oligopeptide comprises at least 6 β³-homoarginine residues.

3. The method of claim 1, wherein the oligopeptide comprises at least 11 β-amino acid residues.

4. A method of translocating a molecule across a membrane of a living cell, the method comprising:

conjugating the molecule to an oligopeptide, the oligopeptide comprising at least 6 β-amino acid residues, at least 6 of which residues are substituted at their β-position carbon with a subatiment selected from the group consisting of —$C_1$–$C_6$—NH—C(=$NH_2^{+)-NH}{}_2$, to thereby yield a conjugate, and further wherein the oligopeptide comprises at least one cyclically-constrained β-amino acid residue; and then contacting the conjugate with the living cell.

5. The method of claim 4, wherein the at least one cyclically-constrained β-amino acid residue is selected from the group consisting of:

$$\begin{array}{c} \text{H} \quad \text{V-----W} \quad \text{O} \\ | \quad\quad | \quad\quad | \quad\quad \| \\ \text{—N—CH—CH—C—} \end{array}$$

wherein V and W are combined, together with the carbon atoms to which they are bonded, and independently define a substituted or unsubsituted, monocyclic or bicyclic $C_3$–$C_{10}$cycloalkyl, cycloalkenyl or heterocyclic ring having one or more N, O or S atom(s) as the heteroatom(s);

the substituents on carbon atoms of the rings being independently selected from the group consisting of hydroxy, linear, branched, or cyclic $C_1$–$C_6$-alkyl, alkenyl, alkynyl; hydroxy-$C_1$–$C_6$-alkyl, amino-$C_1$–$C_6$-alkyl, $C_1$–$C_6$-alkyloxy, $C_1$–$C_6$-alkyloxy-$C_1$–$C_6$-alkyl, amino, mono- or di-$C_1$–$C_6$-alkylamino, carboxamido, carboxamido-$C_1$–$C_6$-alkyl, sulfonamido, sulfonamido-$C_1$–$C_6$-alkyl, urea, cyano, fluoro, thio, $C_1$–$C_6$-alkylthio, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, the substituents on nitrogen heteroatoms of the rings being independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl-$S(=O)_2$—$R^1$, —$C(=O)$—$R^1$, —$S(=O)_2$—$(CH_2)_{n+1}$—$R^2$, and —$C(=O)$—$(CH_2)_n$—$R^2$, where n=1 to 6;

wherein $R^1$ is independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^2$ is independently selected from the group consisting of hydroxy, linear, branched, or cyclic $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residue is further selected from the group consisting of:

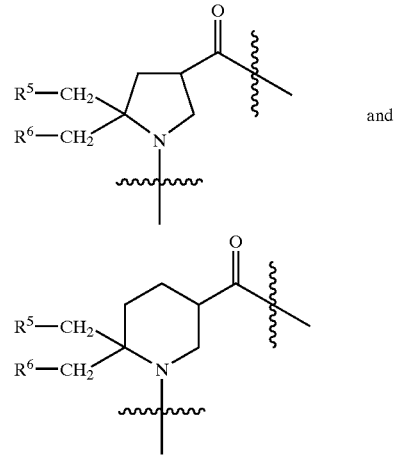

and wherein $R^5$ and $R^6$ are independently selected from the group consisting of hydrogen, hydroxy, linear, branched, or cyclic $C_1$–$C_{16}$-alkyl, alkenyl, or alkynyl; mono- or di-$C_1$–$C_{16}$ alkylamino; mono- or bicyclic aryl; mono- or bicyclic heteroaryl having up to 5 heteroatoms selected from N, O, and S; mono- or bicyclic aryl-$C_1$–$C_{16}$-alkyl; mono- or bicyclic heteroaryl-$C_1$–$C_{16}$-alkyl; —$(CH_2)_{0-6}$—$OR^7$, —$(CH_2)_{0-6}$—$SR^7$, —$(CH_2)_{0-6}$—$S(=O)$—$CH_2$—$R^7$, —$(CH_2)_{0-6}$—$S(=O)_2$—$CH_2$—$R^7$, —$(CH_2)_{0-6}$—$NR^7R^7$, —$(CH_2)_{0-6}$—$NHC(=O)R^7$, —$(CH_2)_{0-6}$—$NHS(=O)_2$—$CH_2$—$R^7$, —$(CH_2)_{0-6}$—$C(=O)$—$OH$, —$(CH_2)_{0-6}$—$C(=O)$—$OR^7$, —$(CH_2)_{0-6}$—$C(=O)$—$NH_2$, —$(CH_2)_{0-6}$—$C(=O)$—$NHR^7$, —$(CH_2)_{0-6}$—$C(=O)$—$N(R^7)_2$, —$(CH_2)_{0-6}$—$O$—$(CH_2)_{2-6}$—$R^8$, —$CH_2)_{0-6}$—$S$—$(CH_2)_{2-6}$—$R^8$, —$(CH_2)_{0-6}$—$S(=O)$—$(CH_2)_{2-6}$—$R^8$, —$(CH_2)_{0-6}$—$S(=O)_2$—$(CH_2)_{2-6}$—$R^8$, —$(CH_2)_{0-6}$—$NH$—$(CH_2)_{2-6}$—$R^8$, —$(CH_2)_{0-6}$—$N\{(CH_2)_{2-6}$—$R^8\}_2$, —$(CH_2)_{0-6}$—$NHC(=O)$—$(CH_2)_{2-6}$—$R^8$, and —$(CH_2)_{0-6}$—$NHS(=O)_2$—$(CH_2)_{2-6}$—$R^8$; wherein $R^7$ is independently selected from the group consisting of hydrogen, $C_1$–$C_6$-alkyl, alkenyl, or alkynyl; mono- or bicycic aryl, mono- or bicyclic heteroaryl having up to 5 heteroatoms selected from N, O, and S; mono- or bicyclic aryl-$C_1$–$C_6$-alkyl, and mono- or bicyclic heteroaryl-$C_1$–$C_6$—alkyl; and $R^8$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residues is further selected from the group consisting of:

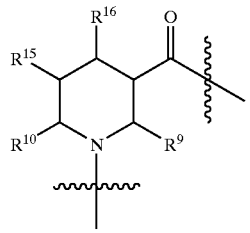 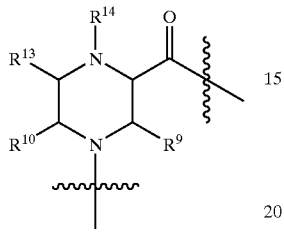

and

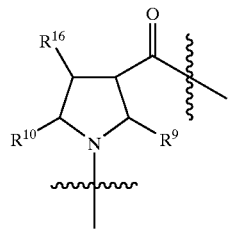

wherein $R^9$, $R^{10}$, and $R^{13}$ are independently selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{1-6}$—$OR^{11}$, —$(CH_2)_{1-6}$—$SR^{11}$, —$(CH_2)_{1-6}$—$S(=O)$—$CH_2$—$R^{11}$, —$(CH_2)_{1-6}$—$S(=O)_2$—$CH_2$—$R^{11}$, —$(CH_2)_{1-6}$—$NR^{11}R^{11}$, —$(CH_2)_{1-6}$—$NHC(=O)R^{11}$, —$(CH_2)_{1-6}$—$NHS(=O)_2$—$CH_2$—$R^{11}$, —$(CH_2)_{0-6}$—$C(=O)$—$OH$, —$(CH_2)_{0-6}$—$C(=O)$—$OR^{11}$, —$(CH_2)_{0-6}$—$C(=O)$—$NH_2$, —$(CH_2)_{0-6}$—$C(=O)$—$NHR^{11}$, —$(CH_2)_{0-6}$—$C(=O)$—$N(R^{11})_2$, —$(CH_2)_{1-6}$—$O$—$(CH_2)_{2-6}$—$R^{12}$, —$(CH_2)_{1-6}$—$S$—$(CH_2)_{2-6}$—$R^{12}$, —$(CH_2)_{1-6}$—$S(=O)$—$(CH_2)_{2-6}$—$R^{12}$, —$(CH_2)_{1-6}$—$S(=O)_2$—$(CH_2)_{2-6}$—$R^{12}$, —$(CH_2)_{1-6}$—$NH$—$(CH_2)_{2-6}$—$R^{12}$, —$(CH_2)_{1-6}$—$N$—$\{(CH_2)_{2-6}$—$R^{12}\}_2$, —$(CH_2)_{1-6}$—$NHC(=O)$—$(CH_2)_{2-6}$—$R^{12}$, and —$(CH_2)_{1-6}$—$NHS(=O)_2$—$(CH_2)_{2-6}$—$R^{12}$; wherein $R^{11}$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^{12}$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane;

$R^{14}$ is selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$S(=O)_2$—$(CH_2)_{1-6}$—$R^{11}$, —$C(=O)R^{11}$, —$S(=O)_2$—$(CH_2)_{2-6}R^{12}$, and —$C(=O)$—$(CH_2)_{2-6}$—$R^{12}$; wherein $R^{11}$ and $R^{12}$ are as defined above;

$R^{15}$ and $R^{16}$ are selected from the group listed above for $R^9$, $R^{10}$, and $R^{13}$, and are further selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane.

6. The method of claim 1, wherein the oligopeptide is selected from the group consisting of:

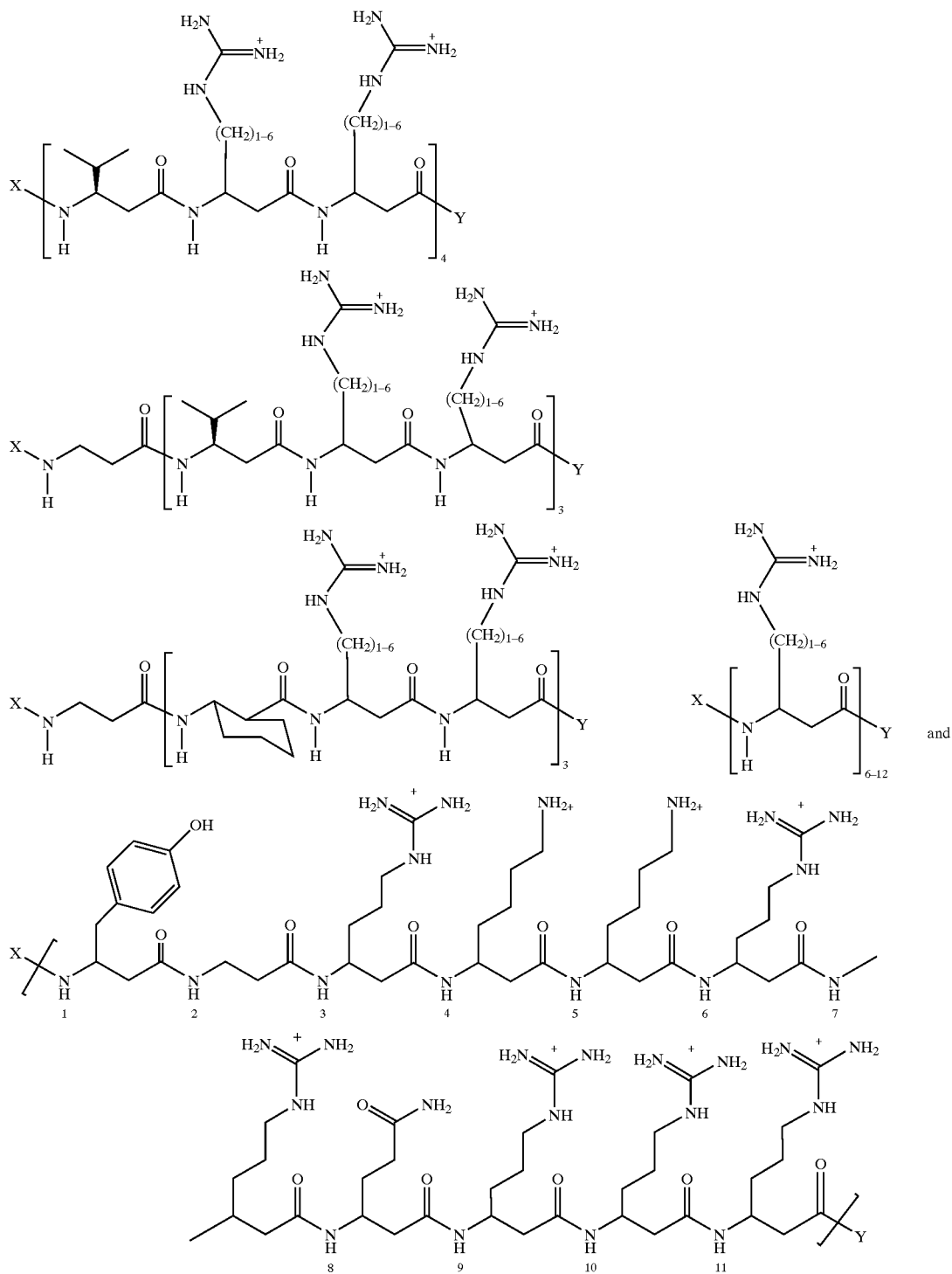

wherein X is hydrogen, an amino-capping group, an amino-protecting group, or a compound of interest; and Y is hydrogen, a carboxy-capping group, a carboxy-protecting group, or a compound of interest.

7. A method of translocating a molecule across a membrane of a living cell, the method comprising contacting a conjugate with the living cell, the conjugate comprising the molecule conjugated to an oligopeptide comprising at least 6 β-amino acid residues, at least 6 of which residues are substituted at their β-position carbon with a substituent selected from the group consisting of —$C_1$-$C_6$—NH—C(=$NH_2^+$)—$NH_2$.

8. The method of claim 7, wherein the oligopeptide comprises at least 6 β-homoarginine residues.

9. The method of claim 7, wherein the oligopeptide comprises at least 11 β-amino acid residues.

10. A method of translocating a molecule across a membrane of a living ccli, the method comprising contacting a conjugate with the living cell, the conjugate comprising the molecule conjugated to an oligopeptide comprising at least 6 β-amino acid residues, at least 6 of which residues are substituted at their β-position carbon with a substituent selected from the group consisting of —C$_1$–C$_6$—NH—C(=NH$_2^+$)—NH$_2$, and further wherein the oligopeptide comprises at least one cyclically-constrained β-amino acid residue.

11. The method of claim 10, wherein the at least one cyclically-constrained β-amino acid residue is selected from the group consisting of:

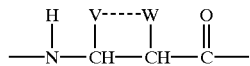

wherein V and W are combined, together with the carbon atoms to which they are bonded, and independently define a substituted or unsubstituted, monocyclic or bicyclic C$_3$–C$_{10}$ cycloalkyl, cycloalkenyl or heterocyclic ring having one or more N, O or S atom(s) as the heteroatom(s);

the substituents on carbon atoms of the rings being independently selected from the group consisting of hydroxy, linear, branched, or cyclic C$_1$–C$_6$-alkyl, alkenyl, alkynyl; hydroxy-C$_1$–C$_6$-alkyl, amino-C$_1$–C$_6$-alkyl, C$_1$–C$_6$-alkyloxy, C$_1$–C$_6$-alkyloxy-C$_1$–C$_6$-alkyl, amino, mono- or di-C$_1$–C$_6$-alkylamino, carboxamido, carboxamido-C$_1$–C$_6$-alkyl, sulfonamido, sulfonamido-C$_1$–C$_6$-alkyl, urea, cyano, fluoro, thio, C$_1$–C$_6$-alkylthio, mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl, the substituents on nitrogen heteroatoms of the rings being independently selected from the group consisting of hydrogen, monocyclic or bicyclic C$_1$–C$_{10}$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl-S(=O)$_2$—R$^1$, —C(=O)—R$^1$, —S(=O)$_2$—(CH$_2$)$_{n+1}$—R$^2$, and —C(=O)—(CH$_2$)$_n$—R$^2$, where n=1 to 6;

wherein R$^1$ is independently selected from the group consisting of hydrogen, monocyclic or bicyclic C$_1$–C$_{10}$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl; and wherein R$^2$ is independently selected from the group consisting of hydroxy, linear, branched, or cyclic C$_1$–C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl; mono- or bicyclic heteroaryl-C$_1$–C$_6$-alkyl; C$_1$–C$_6$-alkyloxy, aryloxy, heteroaryloxy, thio, C$_1$–C$_6$-alkylthio, C$_1$–C$_6$-alkylsulfinyl, C$_1$–C$_6$-alkylsulfonyl, arylthio, arylsulfinyl, arylsulfonyl, heteroarylthio, heteroarylsulfinyl, heteroarylsulfonyl, amino, mono- or di-C$_1$–C$_6$-alkylamino, mono- or diarylamino, mono- or diheteroarylamino, N-alkyl-N-arylamino, N-alkyl-N-heteroarylamino, N-aryl-N-heteroarylamino, aryl-C$_1$–C$_6$-alkylamino, carboxylic acid, carboxamide, mono- or di-C$_1$–C$_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, C$_1$–C$_6$-alkyl ester, aryl ester, heteroaryl ester, sulfonic acid, sulfonamide, mono- or di-C$_1$–C$_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of C$_1$–C$_6$-alkyl, aryl, and heteroaryl; O-alkylurethane, O-arylurethane, and O-heteroarylurethane; and wherein each cyclically-constrained β-amino acid residue is further selected from the group consisting of:

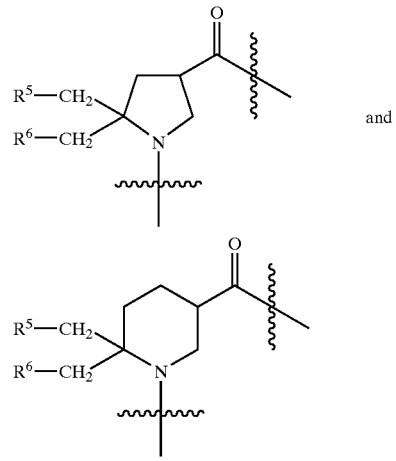

and wherein R$^5$ and R$^6$ are independently selected from the group consisting of hydrogen, hydroxy, linear, branched, or cyclic C$_1$–C$_{16}$-alkyl, alkenyl, or alkynyl; mono- or di-C$_1$–C$_{16}$ alkylamino; mono- or bicyclic aryl; mono- or bicyclic heteroaryl having up to 5 heteroatoms selected from N, O, and S; mono- or bicyclic aryl-C$_1$–C$_{16}$-alkyl; mono- or bicyclic heteroaryl-C$_1$–C$_{16}$-alkyl; —(CH$_2$)$_{0-6}$—OR$^7$, —(CH$_2$)$_{0-6}$—SR$^7$, —(CH$_2$)$_{0-6}$—S(=O)—CH$_2$—R$^7$, —(CH$_2$)$_{0-6}$—S(=O)$_2$—CH$_2$—R$^7$, —(CH$_2$)$_{0-6}$—NR$^7$R$^7$, —(CH$_2$)$_{0-6}$—NHC(=O)R$^7$, —(CH$_2$)$_{0-6}$NHS(=O)$_2$—CH$_2$—R$^7$, —(CH$_2$)$_{0-6}$—C(=O)—OH, —(CH$_2$)$_{0-6}$—C(=O)—OR$^7$, —(CH$_2$)$_{0-6}$—C(=O)—NH$_2$, —(CH$_2$)$_{0-6}$—C(=O)—NHR$^7$, —(CH$_2$)$_{0-6}$—C(=O)—N(R$^7$)$_2$, —(CH$_2$)$_{0-6}$—O—(CH$_2$)$_{2-6}$—R$^8$, —(CH$_2$)$_{0-6}$—S—(CH$_2$)$_{2-6}$—R$^8$, —(CH$_2$)$_{0-6}$—S(=O)—(CH$_2$)$_{2-6}$—R$^8$, —(CH$_2$)$_{0-6}$—S(=O)$_2$—(CH$_2$)$_{2-6}$—R$^8$, —(CH$_2$)$_{0-6}$—NH—(CH$_2$)$_{2-6}$—R$^8$, —(CH$_2$)$_{0-6}$—N—{(CH$_2$)$_{2-6}$—R$^8$}$_2$, —(CH$_2$)$_{0-6}$—NHC(=O)—(CH$_2$)$_{2-6}$—R$^8$, and —(CH$_2$)$_{0-6}$—NHS(=O)$_2$—(CH$_2$)$_{2-6}$—R$^8$; wherein R$^7$ is independently selected from the group consisting of hydrogen, C$_1$–C$_6$-alkyl, alkenyl, or alkynyl; mono- or bicyclic aryl, mono- or bicyclic heteroaryl having up to 5 heteroatoms selected from N, O, and S; mono- or bicyclic aryl-C$_1$–C$_6$-alkyl, mono- or bicyclic heteroaryl-C$_1$–C$_6$-alkyl; and R$^8$ is selected from the group consisting of hydroxy, C$_1$–C$_6$-alkyloxy, aryloxy, heteroaryloxy, thio, C$_1$–C$_6$-alkylthio, C$_1$–C$_6$-alkylsulfinyl, C$_1$–C$_6$- alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residues is further selected from the group consisting of:

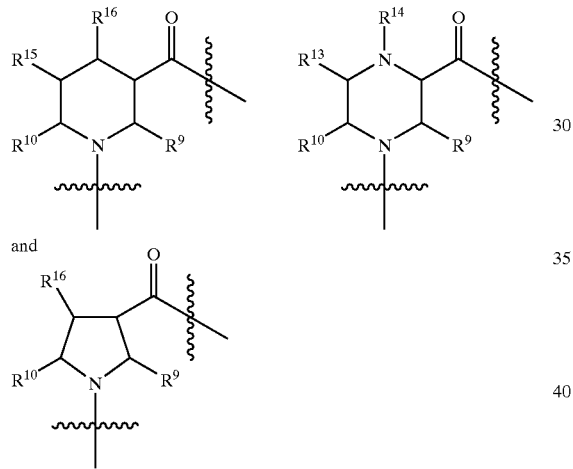

and wherein $R^9$, $R^{10}$, and $R^{13}$ are independently selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{1-6}$—$OR^{11}$, —$(CH_2)_{1-6}$—$SR^{11}$, —$(CH_2)_{1-6}$—$S(=O)$—$CH_2$—$R^{11}$, —$(CH_2)_{1-6}$-$S(=O)_2$—$CH_2$—$R^{11}$, —$(CH_2)_{1-6}$—$NR^{11}R^{11}$, —$(CH_2)_{1-6}$—$NHC(=O)R^{11}$, —$(CH_2)_{1-6}$—$NHS(=O)_2$—$CH_2$—$R^{11}$, —$(CH_2)_{0-6}$—$C(=O)$—$OH$, —$(CH_2)_{0-6}$—$C(=O)$—$OR^{11}$, —$(CH_2)_{0-6}$—$C(=O)$—$NH_2$, —$(CH_2)_{0-6}$—$C(=O)$—$NHR^{11}$, —$(CH_2)_{0-6}$—$C(=O)$—$N(R^{11})_2$, —$(CH_2)_{1-6}$—$O$—$(CH_2)_{2-6}$—$R^{12}$, —$(CH_2)_{1-6}$—$S$—$(CH_2)_{2-6}$—$R^{12}$, —$(CH_2)_{1-6}$—$S(=O)$—$(CH_2)_{2-6}$—$R^{12}$, —$(CH_2)_{1-6}$—$S(=O)_2$—$(CH_2)_{2-6}$—$R^{12}$, —$(CH_2)_{1-6}$—$NH$—$(CH_2)_{2-6}$—$R^{12}$, —$(CH_2)_{1-6}$—$N$—$\{(CH_2)_{2-6}$—$R^{12}\}_2$, —$(CH_2)_{1-6}$—$NHC(=O)$—$(CH_2)_{2-6}$—$R^{12}$, and —$(CH_2)_{1-6}$—$NHS(=O)_2$—$(CH_2)_{2-6}$—$R^{12}$; wherein $R^{11}$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^{12}$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane;

$R^{14}$ is selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$S(=O)_2$—$(CH_2)_{1-6}$—$R^{11}$, —$C(=O)R^{11}$, —$S(=O)_2$—$(CH_2)_{2-6}R^{12}$, and —$C(=O)$—$(CH_2)_{1-6}$—$R^{12}$; wherein $R^{11}$ and $R^{12}$ are as defined above;

$R^{15}$ and $R^{16}$ are selected from the group listed above for $R^9$, $R^{10}$, and $R^{13}$, and are further selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane.

12. The method of claim 7, wherein the oligopeptide is selected from the group consisting of:

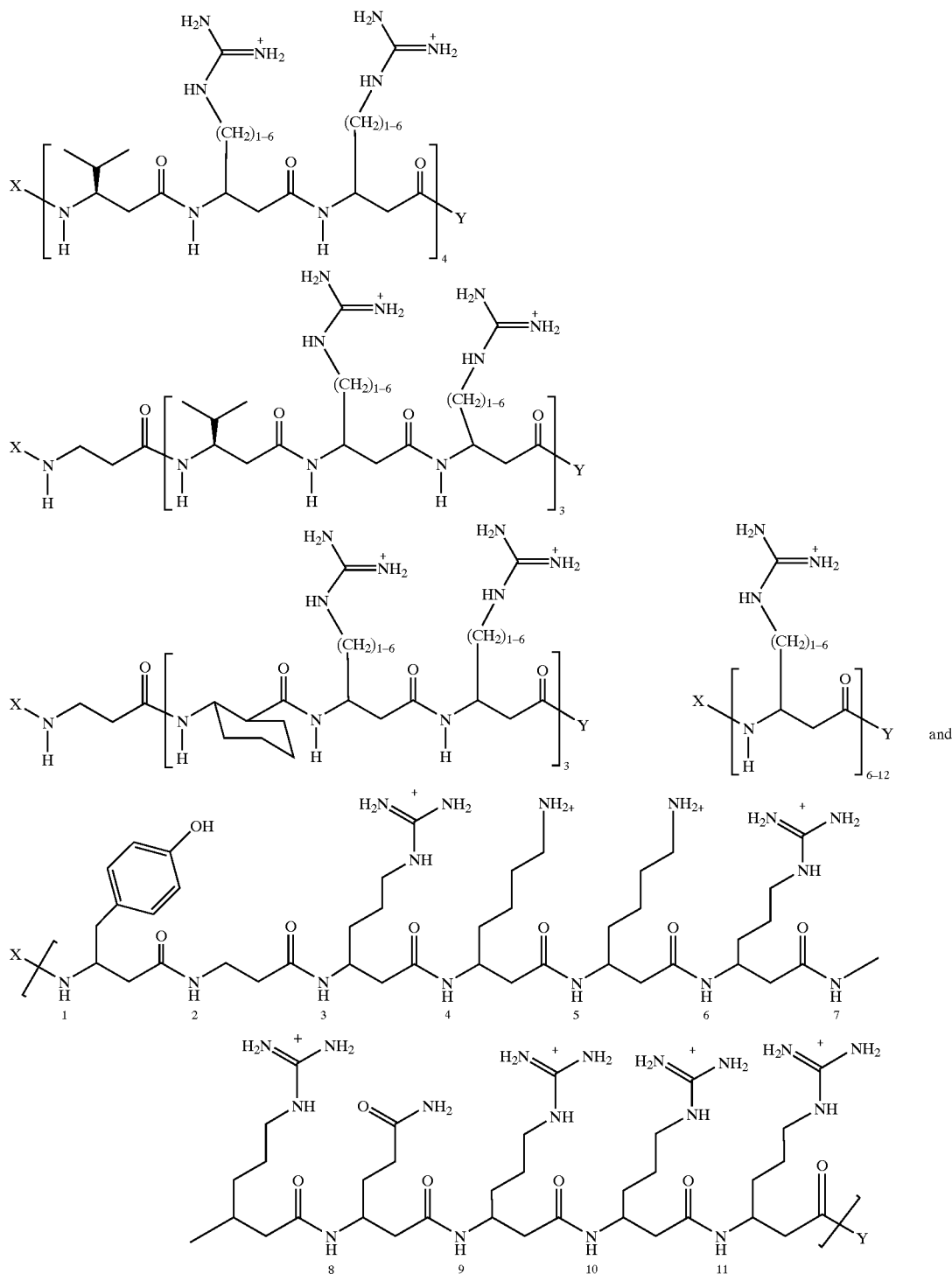

wherein X is hydrogen, an amino-capping group, an amino-protecting group, or a compound of interest; and Y is hydrogen, a carboxy-capping group, a carboxy-protecting group, or a compound of interest.

13. A β-peptide comprising at least 6 β-amino acid residues, at least 6 of which residues are substituted at their β-position carbon with a substituent selected from the group consisting of —$C_1$–$C_6$—NH—C(=$NH_2^+$)—$NH_2$, the β-peptide being capable of translocating across a membrane of a living cell.

14. The β-peptide of claim 13, wherein the β-peptide comprises at least 6 $β^3$-homoarginine residues.

15. The β-peptide of claim 13, wherein the β-peptide comprises at least 11 β-amino acid residues.

16. The β-peptide of claim 13, wherein the β-peptide comprises at least one cyclically-constrained β-amino acid residue.

17. The β-peptide of claim 16, wherein the at least one cyclically-constrained β-amino acid residue is selected from the group consisting of:

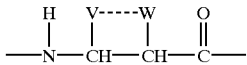

wherein V and W are combined, together with the carbon atoms to which they are bonded, and independently define a substituted or unsubstituted, monocyclic or bicyclic $C_3$–$C_{10}$ cycloalkyl, cycloalkenyl or heterocyclic ring having one or more N, O or S atom(s) as the heteroatom(s);

the substituents on carbon atoms of the rings being independently selected from the group consisting of hydroxy, linear, branched, or cyclic $C_1$–$C_6$-alkyl, alkenyl, alkynyl; hydroxy-$C_1$–$C_6$-alkyl, amino-$C_1$–$C_6$-alkyl, $C_1$–$C_6$-alkyloxy, $C_1$–$C_6$-alkyloxy-$C_1$–$C_6$-alkyl, amino, mono- or di-$C_1$–$C_6$-alkylamino, carboxamido, carboxamido-$C_1$–$C_6$-alkyl, sulfonamido, sulfonamido-$C_1$–$C_6$-alkyl, urea, cyano, fluoro, thio, $C_1$–$C_6$-alkylthio, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, the substituents on nitrogen heteroatoms of the rings being independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl-S(=O)$_2$—$R^1$, —C(=O)—$R^1$, —S(=O)$_2$—(CH$_2$)$_n$+, —$R^2$, and —C(=O)—(CH$_2$)$_n$—$R^2$, where n=1 to 6;

wherein $R^1$ is independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^2$ is independently selected from the group consisting of hydroxy, linear, branched, or cyclic $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsituent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residue is further selected from the group consisting of:

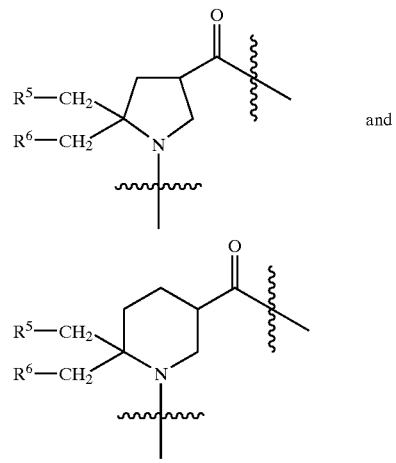

wherein $R^5$ and $R^6$ are independently selected from the group consisting of hydrogen, hydroxy, linear, branched, or cyclic $C_1$–$C_{16}$-alkyl, alkenyl, or alkynyl; mono- or di-$C_1$–$C_{16}$ alkylamino; mono- or bicyclic aryl; mono- or bicyclic heteroaryl having up to 5 heteroatoms selected from N, O, and S; mono- or bicyclic aryl-$C_1$–$C_{16}$-alkyl; mono- or bicyclic heteroaryl-$C_1$–$C_{16}$-alkyl; —(CH$_2$)$_{0-6}$—OR$^7$, —(CH$_2$)$_{0-6}$—SR$^7$, —(CH$_2$)$_{0-6}$—S(=O)—CH$_2$—R$^7$, —(CH$_2$)$_{0-6}$—S(=O)$_2$—CH$_2$—R$^7$, —(CH$_2$)$_{0-6}$—NR$^7$R$^7$, —(CH$_2$)$_{1-6}$—NHC(=O)R$^7$, —(CH$_2$)$_{0-6}$—NHS(=O)$_2$—CH$_2$—R$^7$, —(CH$_2$)$_{0-6}$—C(=O)—OH, —(CH$_2$)$_{0-6}$—C(=O)—OR$^7$, —(CH$_2$)$_{0-6}$—C(=O)—NH$_2$, —(CH$_2$)$_{0-6}$—C(=O)—NHR$^7$, —(CH$_2$)$_{0-6}$—C(=O)—N(R$^7$)$_2$, —(CH$_2$)$_{0-6}$—O—(CH$_2$)$_{2-6}$—R$^8$, —(CH$_2$)$_{0-6}$—S—(CH$_2$)$_{2-6}$—R$^8$, —(CH$_2$)$_{0-6}$—S(=O)—(CH$_2$)$_{2-6}$—R$^8$, —(CH$_2$)$_{0-6}$—S(=O)$_2$—(CH$_2$)$_{2-6}$—R$^8$, —(CH$_2$)$_{0-6}$—NH—(CH$_2$)$_{2-6}$—R$^8$, —(CH$_2$)$_{0-6}$—N—{(CH$_2$)$_{2-6}$—R$^8$}$_2$, —(CH$_2$)$_{0-6}$—NHC(=O)—(CH$_2$)$_{2-6}$—R$^8$, and —(CH$_2$)$_{0-6}$—NHS(=O)$_2$—(CH$_2$)$_{2-6}$—R$^8$; wherein $R^7$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^8$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N- heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residues is further selected from the group consisting of:

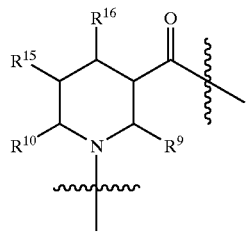 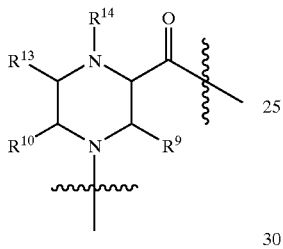

and

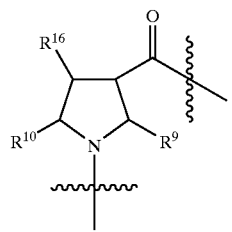

wherein $R^9$, $R^{10}$, and $R^{13}$ are independently selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{1-6}$-$OR^{11}$, —$(CH_2)_{1-6}$—$SR^{11}$, —$(CH_2)_{1-6}$—$S(=O)$—$CH_2$—$R^{11}$, —$(CH_2)_{1-6}$—$S(=O)_2$—$CH_2$—$R^{11}$, —$(CH_2)_{1-6}$—$NR^{11}R^{11}$, —$(CH_2)_{1-6}$—$NHC(=O)R^{11}$, —$(CH_2)_{1-6}$—$NHS(=O)_2$—$CH_2$—$R^{11}$, —$(CH_2)_{0-6}$—$C(=O)$—$OH$, —$(CH_2)_{0-6}$—$C(=O)$—$OR^{11}$, —$(CH_2)_{0-6}$—$C(=O)$—$NH_2$, —$(CH_2)_{0-6}$—$C(=O)$—$NHR^{11}$, —$(CH_2)_{0-6}$—$C(=O)$—$N(R^{11})_2$, —$(CH_2)_{1-6}$—$O$—$(CH_2)_{2-6}$—$R^{12}$, —$(CH_2)_{1-6}$—$S$—$(CH_2)_{2-6}$—$R^{12}$, —$(CH_2)_{1-6}$—$S(=O)$—$(CH_2)_{2-6}$—$R^{12}$, —$(CH_2)_{1-6}$—$S(=O)_2$—$(CH_2)_{2-6}$—$R^{12}$, —$(CH_2)_{1-6}$—$NH$—$(CH_2)_{2-6}$—$R^{12}$, —$(CH_2)_{1-6}$—$N$—$\{(CH_2)_{2-6}$—$R^{12}\}_2$, —$(CH_2)_{1-6}$—$NHC(=O)$—$(CH_2)_{2-6}$—$R^{12}$, and —$(CH_2)_{1-6}$—$NHS(=O)_2$—$(CH_2)_{2-6}$—$R^{12}$; wherein $R^{11}$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^{12}$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane;

$R^{14}$ is selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$S(=O)_2$—$(CH_2)_{1-6}$—$R^{11}$, —$C(=O)R^{11}$, —$S(=O)_2$—$(CH_2)_{2-6}R^{12}$, and —$C(=O)$—$(CH_2)_{1-6}$—$R^{12}$; wherein $R^{11}$ and $R^{12}$ are as defined above;

$R^{15}$ and $R^{16}$ are selected from the group listed above for $R^9$, $R^{10}$, and $R^{13}$, and are further selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane.

18. The β-peptide of claim 13, wherein the β-peptide is selected from the group consisting of:

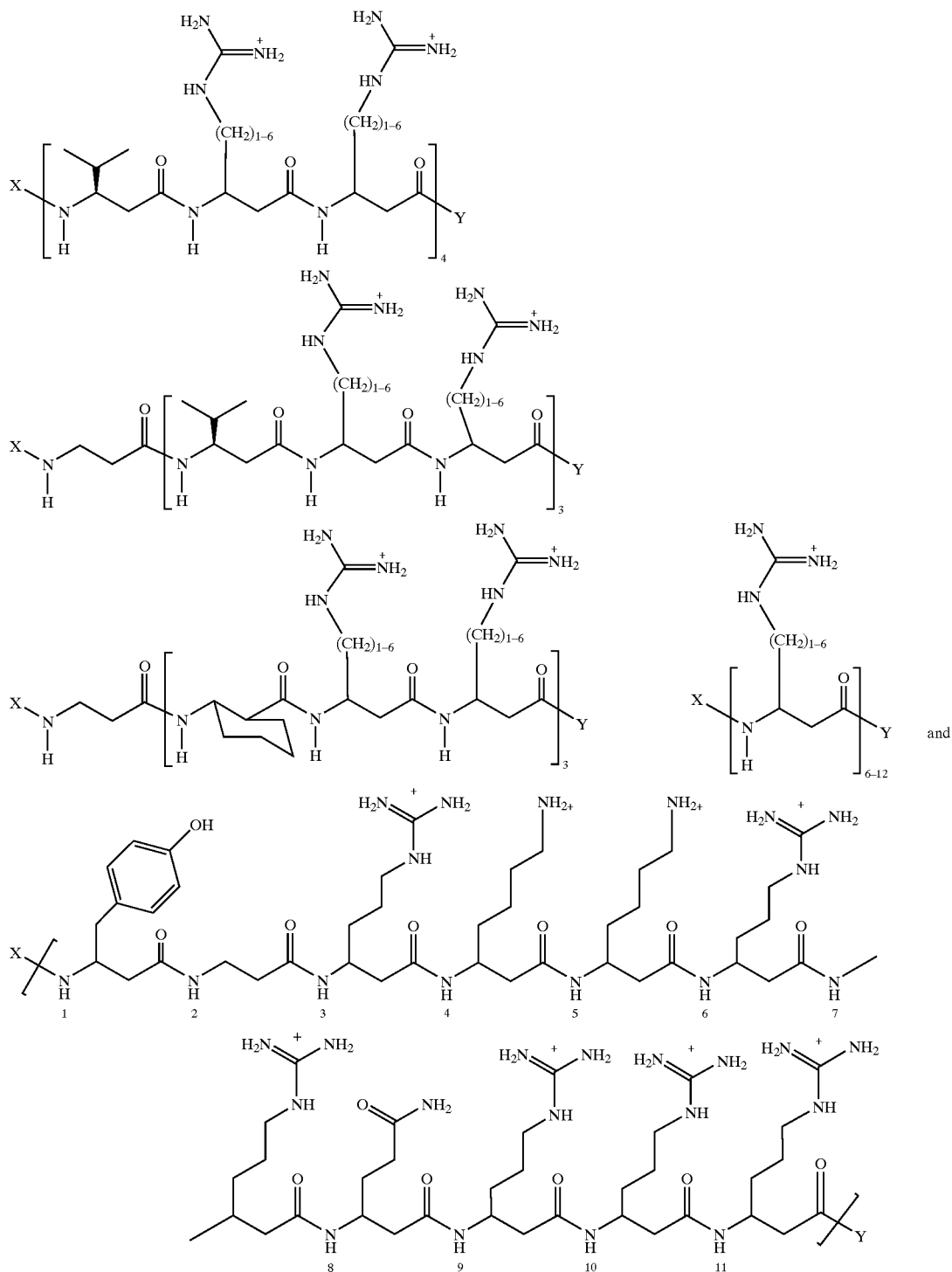

wherein X is hydrogen, an amino-capping group, an amino-protecting group, or a compound of interest; and Y is hydrogen, a carboxy-capping group, a carboxy-protecting group, or a compound of interest.

19. The β-peptide of claim 13, having conjugated thereto a pharmacologically-active molecule.

20. The β-peptide of claim 19, wherein the pharmacologically-active molecule is conjugated to a terminus of the β-peptide.

21. A conjugate comprising:
a β-peptide vehicle, the β-peptide vehicle comprising at least 6 β-amino acid residues, at least 6 of which residues are substituted at their β-position carbon with a substituent selected from the group consisting of —$C_1$–$C_6$—NH—C(=$NH_2^+$)—$NH_2$; and
a molecule of interest conjugated to the β-peptide vehicle.

22. The conjugate of claim 21, wherein the β-peptide vehicle comprises at least 6 $β^3$-homoarginine residues.

23. The conjugate of claim 21, wherein the β-peptide vehicle comprises at least 11 β-amino acid residues.

24. The conjugate of claim 21, wherein the β-peptide vehicle comprises at least one cyclically-constrained β-amino acid residue.

25. The conjugate of claim 24, wherein the at least one cyclically-constrained β-amino acid residue is independently selected from the group consisting of:

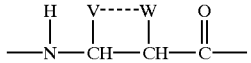

wherein V and W are combined, together with the carbon atoms to which they are bonded, and independently define a substituted or unsubsituted, monocyclic or bicyclic $C_3$–$C_{10}$ cycloalkyl, cycloalkenyl or heterocyclic ring having one or more N, O or S atom(s) as the heteroatom(s);

the substituents on carbon atoms of the rings being independently selected from the group consisting of hydroxy, linear, branched, or cyclic $C_1$–$C_6$-alkyl, alkenyl, alkynyl; hydroxy-$C_1$–$C_6$-alkyl, amino-$C_1$–$C_6$-alkyl, $C_1$–$C_6$-alkyloxy, $C_1$–$C_6$-alkyloxy-$C_1$–$C_6$-alkyl, amino, mono- or di-$C_1$–$C_6$-alkylamino, carboxamido, carboxamido-$C_1$–$C_6$-alkyl, sulfonamido, sulfonamido-$C_1$–$C_6$-alkyl, urea, cyano, fluoro, thio, $C_1$–$C_6$-alkylthio, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, the substituents on nitrogen heteroatoms of the rings being independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl-S($=$O)$_2$—$R^1$, —C($=$O)—$R^1$, —S($=$O)$_2$—(CH$_2$)$_{n+1}$—$R^2$, and —C($=$O)—(CH$_2$)$_n$—$R^2$, where n=1 to 6;

wherein $R^1$ is independently selected from the group consisting of hydrogen, monocyclic or bicyclic $C_1$–$C_{10}$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and wherein $R^2$ is independently selected from the group consisting of hydroxy, linear, branched, or cyclic $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl; mono- or bicyclic heteroaryl-$C_1$–$C_6$-alkyl; $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residue is further selected from the group consisting of:

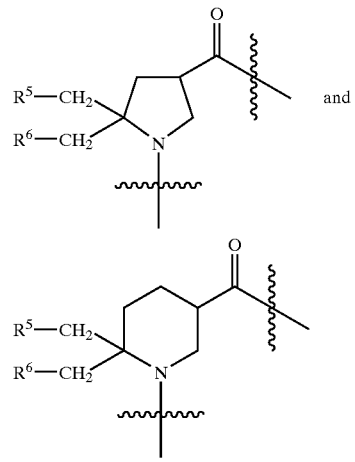

wherein $R^5$ and $R^6$ are independently selected from the group consisting of hydrogen, hydroxy, linear, branched, or cyclic $C_1$–$C_{16}$-alkyl, alkenyl, or alkynyl; mono- or di-$C_1$–$C_{16}$ alkylamino; mono- or bicyclic aryl; mono- or bicyclic heteroaryl having up to 5 heteroatoms selected from N, O, and S; mono- or bicyclic aryl-$C_1$–$C_{16}$-alkyl; mono- or bicyclic heteroaryl-$C_1$–$C_{16}$-alkyl; —(CH$_2$)$_{0-6}$—OR$^7$, —(CH$_2$)$_{0-6}$—SR$^7$, —(CH$_2$)$_{0-6}$—S($=$O)—CH$_2$—R$^7$, —(CH$_2$)$_{0-6}$—S($=$O)$_2$—CH$_2$—R$^7$, —(CH$_2$)$_{0-6}$—NR$^7$R$^7$, —(CH$_2$)$_{0-6}$—NHC($=$O)R$^7$, —(CH$_2$)$_{0-6}$—NHS($=$O)$_2$—CH$_2$—R$^7$, —(CH$_2$)$_{0-6}$—C($=$O)—OH, —(CH$_2$)$_{0-6}$—C($=$O)—OR$^7$, —(CH$_2$)$_{0-6}$—C($=$O)—NH$_2$, —(CH$_2$)$_{0-6}$—C($=$O)—NHR$^7$, —(CH$_2$)$_{0-6}$—C($=$O)—N(R$^7$)$_2$, —(CH$_2$)$_{0-6}$—O—(CH$_2$)$_{2-6}$—R$^8$, —CH$_2$)$_{0-6}$—S—(CH$_2$)$_{2-6}$—R$^8$, —(CH$_2$)$_{0-6}$—S($=$O)—(CH$_2$)$_{2-6}$—R$^8$, —(CH$_2$)$_{0-6}$—S($=$O)$_2$—(CH$_2$)$_{2-6}$—R$^8$, —(CH$_2$)$_{0-6}$—NH—(CH$_2$)$_{2-6}$—R$^8$, —(CH$_2$)$_{0-6}$—N—{(CH$_2$)$_{2-6}$—R$^8$}$_2$, —(CH$_2$)$_{0-6}$—NHC($=$O)—(CH$_2$)$_{2-6}$—R$^8$, and —(CH$_2$)$_{0-6}$—NHS($=$O)$_2$—(CH$_2$)$_{2-6}$—R$^8$; wherein $R^7$ is independently selected from the group consisting of hydrogen, $C_1$–$C_6$-alkyl, alkenyl, or alkynyl; mono- or bicycic aryl, mono- or bicyclic heteroaryl having up to 5 heteroatoms selected from N, O, and S; mono- or bicyclic aryl-$C_1$–$C_6$-alkyl, and mono- or bicyclic heteroaryl-$C_1$–$C_6$—alkyl; and $R^8$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane; and wherein each cyclically-constrained β-amino acid residues is further selected from the group consisting of:

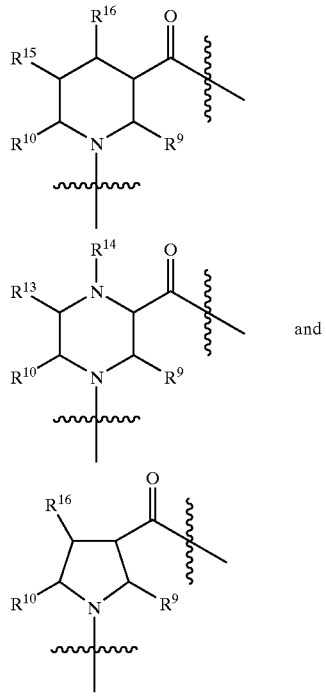

and wherein $R^9$, $R^{10}$, and $R^{13}$ are independently selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$(CH_2)_{1-6}$—$OR^{11}$, —$(CH_2)_{1-6}$—$SR^{11}$, —$(CH_2)_{1-6}$—$S(=O)$—$CH_2$—$R^{11}$, —$(CH_2)_{1-6}$—$S(=O)_2$—$CH_2$—$R^{11}$, —$(CH_2)_{1-6}$—$NR^{11}R^{11}$, —$(CH_2)_{1-6}$—$NHC(=O)R^{11}$, —$(CH_2)_{1-6}$—$NHS(=O)_2$—$CH_2$—$R^{11}$, —$(CH_2)_{0-6}$—$C(=O)$—$OH$, —$(CH_2)_{0-6}$—$C(=O)$—$OR^{11}$, —$(CH_2)_{0-6}$—$C(=O)$—$NH_2$, —$(CH_2)_{0-6}$—$C(=O)$—$NHR^{11}$, —$(CH_2)_{0-6}$—$C(=O)$—$N(R^{11})_2$, —$(CH_2)_{1-6}$—$O$—$(CH_2)_{2-6}$—$R^{12}$, —$(CH_2)_{1-6}$—$S$—$(CH_2)_{2-6}$—$R^{12}$, —$(CH_2)_{1-6}$—$S(=O)$—$(CH_2)_{2-6}$—$R^{12}$, —$(CH_2)_{1-6}$—$S(=O)_2$—$(CH_2)_{2-6}$—$R^{12}$, —$(CH_2)_{1-6}$—$NH$—$(CH_2)_{2-6}$—$R^{12}$, —$(CH_2)_{1-6}$—$N$—$\{(CH_2)_{2-6}$—$R^{12}\}_2$, —$(CH_2)_{1-6}$—$NHC(=O)$—$(CH_2)_{2-6}$—$R^{12}$, and —$(CH_2)_{1-6}$—$NHS(=O)_2$—$(CH_2)_{2-6}$—$R^{12}$; wherein $R^{11}$ is independently selected from the group consisting of hydrogen, $C_1$–$C_6$-alkyl, alkenyl, or alkynyl; mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl; and $R^{12}$ is selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane;

$R^{14}$ is selected from the group consisting of hydrogen, linear, branched, or cyclic $C_1$–$C_6$-alkyl, alkenyl, or alkynyl; mono- or di-$C_1$–$C_6$ alkylamino, mono- or bicyclic aryl, mono- or bicyclic heteroaryl having up to 5 heteroatoms selected from N, O, and S; mono- or bicyclic aryl-$C_1$–$C_6$-alkyl, mono- or bicyclic heteroaryl-$C_1$–$C_6$-alkyl, —$S(=O)_2$—$(CH_2)_{1-6}$—$R^{11}$, —$C(=O)R^{11}$, —$S(=O)_2$—$(CH_2)_{2-6}R^{12}$, and —$C(=O)$—$(CH_2)_{1-6}$—$R^{12}$; wherein $R^{11}$ and $R^{12}$ are as defined above;

$R^{15}$ and $R^{16}$ are selected from the group listed above for $R^9$, $R^{10}$, and $R^{13}$, and are further selected from the group consisting of hydroxy, $C_1$–$C_6$-alkyloxy, aryloxy, heteroaryloxy, thio, $C_1$–$C_6$-alkylthio, $C_1$–$C_6$-alkylsulfinyl, $C_1$–$C_6$-alkylsulfonyl, arylthio, arylsulfinyl, arylsulfonyl, heteroarylthio, heteroarylsulfinyl, heteroarylsulfonyl, amino, mono- or di-$C_1$–$C_6$-alkylamino, mono- or diarylamino, mono- or diheteroarylamino, N-alkyl-N-arylamino, N-alkyl-N-heteroarylamino, N-aryl-N-heteroarylamino, aryl-$C_1$–$C_6$-alkylamino, carboxylic acid, carboxamide, mono- or di-$C_1$–$C_6$-alkylcarboxamide, mono- or diarylcarboxamide, mono- or diheteroarylcarboxamide, N-alkyl-N-arylcarboxamide, N-alkyl-N-heteroarylcarboxamide, N-aryl-N-heteroarylcarboxamide, $C_1$–$C_6$-alkyl ester, aryl ester, heteroaryl ester, sulfonic acid, sulfonamide, mono- or di-$C_1$–$C_6$-alkylsulfonamide, mono- or diarylsulfonamide, mono- or diheteroarylsulfonamide, N-alkyl-N-arylsulfonamide, N-alkyl-N-heteroarylsulfonamide, N-aryl-N-heteroarylsulfonamide, urea; mono- di- or tri-substituted urea, wherein the subsitutent(s) is selected from the group consisting of $C_1$–$C_6$-alkyl, aryl, and heteroaryl; O-alkylurethane, O-arylurethane, and O-heteroarylurethane.

26. The conjugate of claim 21, wherein the β-peptide vehicle is selected from the group consisting of:

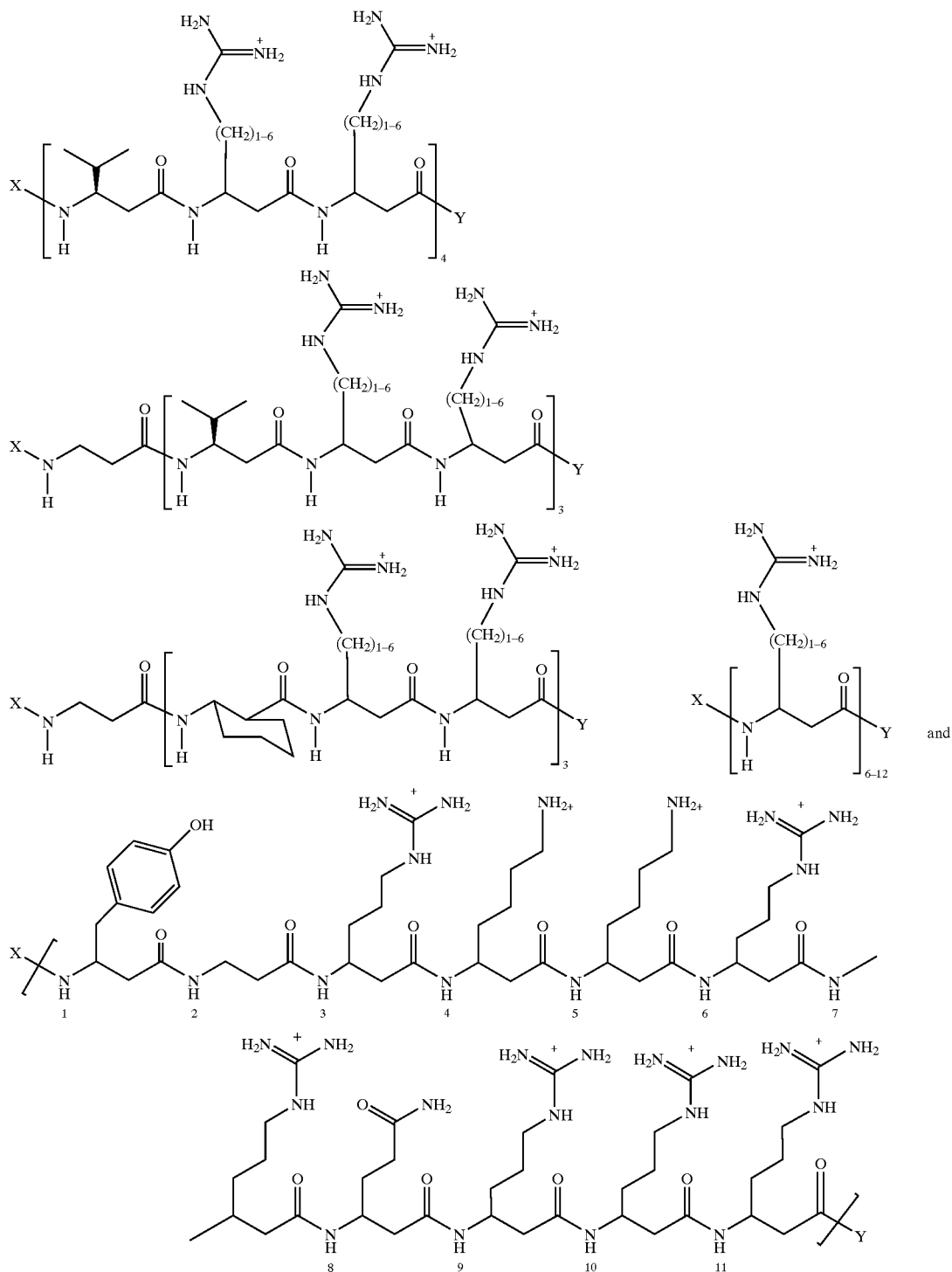
wherein X is hydrogen, an amino-capping group, an amino-protecting group, or the molecule of interest; and Y is hydrogen, a carboxy-capping group, a carboxy-protecting group, or the molecule of interest, provided that one or both of X and/or Y is the molecule of interest.
* * * * *